United States Patent
Payne et al.

(10) Patent No.: US 7,834,155 B2
(45) Date of Patent: Nov. 16, 2010

(54) CA6 ANTIGEN-SPECIFIC CYTOTOXIC CONJUGATE AND METHODS OF USING THE SAME

(75) Inventors: Gillian Payne, Waban, MA (US); Philip Chun, Malden, MA (US); Daniel J. Tavares, Natick, MA (US)

(73) Assignee: Immunogen Inc., Waltham, MA (US)

( * ) Notice: Subject to any disclaimer, the term of this patent is extended or adjusted under 35 U.S.C. 154(b) by 0 days.

(21) Appl. No.: 11/213,046

(22) Filed: Aug. 29, 2005
(Under 37 CFR 1.47)

(65) Prior Publication Data

US 2007/0041980 A1    Feb. 22, 2007

Related U.S. Application Data

(63) Continuation-in-part of application No. 10/895,135, filed on Jul. 21, 2004, now abandoned.

(60) Provisional application No. 60/488,447, filed on Jul. 21, 2003.

(51) Int. Cl.
*C12P 21/08* (2006.01)
*C07K 16/00* (2006.01)
*A61K 39/395* (2006.01)
*C12P 21/04* (2006.01)
*C07H 21/04* (2006.01)

(52) U.S. Cl. .............. 530/387.3; 530/388.1; 530/388.8; 530/388.85; 530/391.7; 424/133.1; 424/141.1; 424/155.1; 424/156.1; 435/69.6; 435/70.21

(58) Field of Classification Search .................... None
See application file for complete search history.

(56) References Cited

U.S. PATENT DOCUMENTS

| | | | |
|---|---|---|---|
| 5,416,064 | A | 5/1995 | Chari et al. |
| 5,618,920 | A * | 4/1997 | Robinson et al. |
| 5,639,641 | A | 6/1997 | Pedersen et al. |
| 5,776,456 | A | 7/1998 | Anderson et al. |
| 6,333,410 | B1 | 12/2001 | Chari et al. |
| 6,340,701 | B1 | 1/2002 | Chari et al. |
| 6,596,503 | B1 | 7/2003 | Wennerberg et al. |
| 7,507,410 | B2 | 3/2009 | Kellogg et al. |
| 2003/0215895 | A1 | 11/2003 | Wennerberg et al. |
| 2004/0241174 | A1 | 12/2004 | Godfrey et al. |

FOREIGN PATENT DOCUMENTS

| | | |
|---|---|---|
| JP | 4-502408 | 5/1992 |
| WO | 9007861 | 7/1990 |
| WO | WO 91/09967 | 7/1991 |
| WO | WO 02/16401 | 2/2002 |
| WO | WO 03/050260 | 3/2003 |

OTHER PUBLICATIONS

Fundamental Immunology, William E. Paul, ed., 3rd Ed., pp. 292-295, 1993.*
Rudikoff et al. Proc. Natl. Acad. Sci. USA, 79(6):1979-1983, Mar. 1982.*
Colman P. M. Research in Immunology, 145:33-36, 1994.*
Bendig M. M. Methods: A Companion to Methods in Enzymology, 8:83-93, 1995.*
MacCallum et al. J. Mol. Biol., 262, 732-745, 1996.*
Casset et al. Biochemical and Biophysical Research Communications, 307:198-205, 2003.*
Raag et al. FASEB J., 9(1):73-80, 1995.*
Smith et al, *International J. of Gynecological Pathology*, 20:260-266 (2001).
Smith et al, *Applied Immunohistochemistry & Molecular Morphology*, 10(2):152-158 (2002).
Kearse et al, *Int. J. Cancer*, 88:866-872 (2000).
Smith et al, *Human Antibodies*, 9:61-65 (1999).
Chun et al, "Potent Anti-Cancer Activity of DS6-DM1, an Antibody-drug Conjugate Targeting a *Muc*1 Glycotope on Ovarian, Breast, and Pancreatic Carcinomas", AACR-NCI-EORTC International Conference on Molecular Targets and Cancer Therapeutics, Discovery, Biology, and Clinical Applications Hynes Cancer, Boston, MA, B205 (Nov. 17-21, 2003).
Studnicka et al, *Protein Engineering*, 7(6):805-814 (1994).
Roguska et al, *Protein Engineering*, 9(10):895-904 (1996).
Smith et al.; "Patterns of Expression of the DS6-glycoform of MUC1 Correlates with Known Prognostic Indicators in Breast Cancer;" Proceedings of the Annual Meeting of the American Associattion for Cancer Research; New York; vol. 45, Jan. 1, 2004; p. 239, Abstract 1051, XP001247901.

* cited by examiner

*Primary Examiner*—David J. Blanchard
(74) *Attorney, Agent, or Firm*—Sughrue Mion, PLLC

(57) ABSTRACT

Cytotoxic conjugates comprising a cell binding agent and a cytotoxic agent, therapeutic compositions comprising the conjugate, methods for using the conjugates in the inhibition of cell growth and the treatment of disease, and a kit comprising the cytotoxic conjugate are disclosed are all embodiments of the invention. In particular, the cell binding agent is a monoclonal antibody, and epitope-binding fragments thereof, that recognizes and binds the CA6 glycotope. The present invention is also directed to humanized or resurfaced versions of DS6, an anti-CA6 murine monoclonal antibody, and epitope-binding fragments thereof.

21 Claims, 34 Drawing Sheets

Figure 2
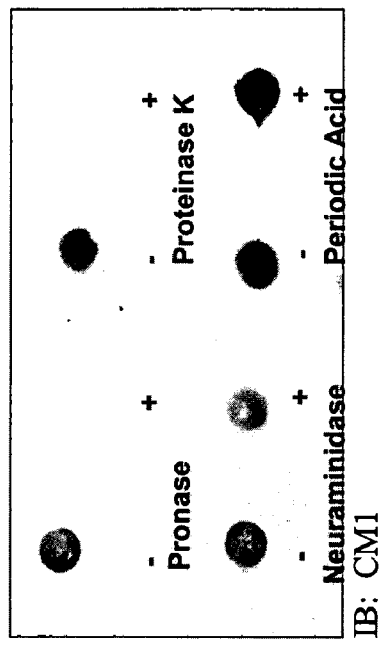
A. Caov-3
IB: DS6
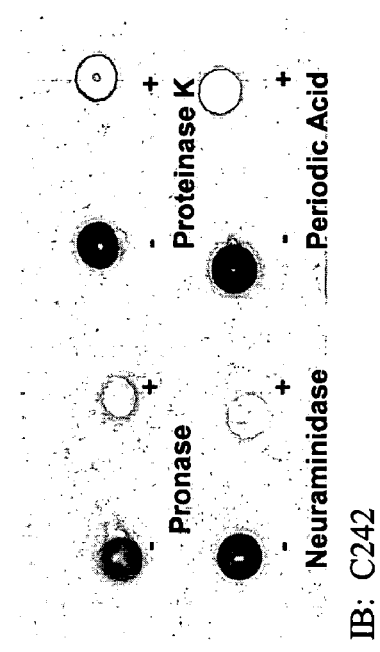
B. Caov-3
IB: CM1
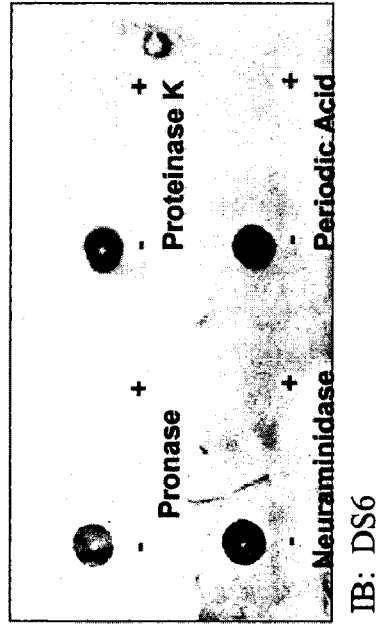
C. SKMEL28
IB: R24
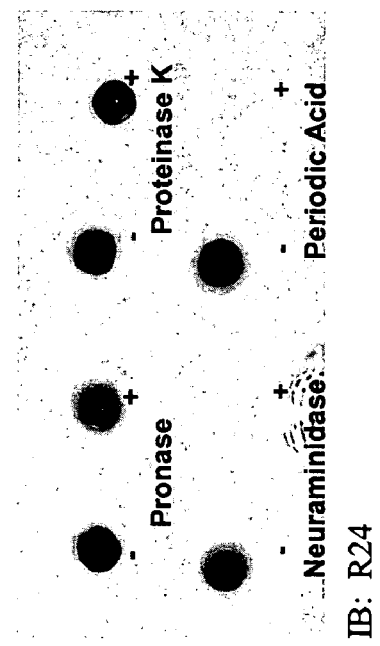
D. Colo205
IB: C242

Figure 5
A. Caov-3
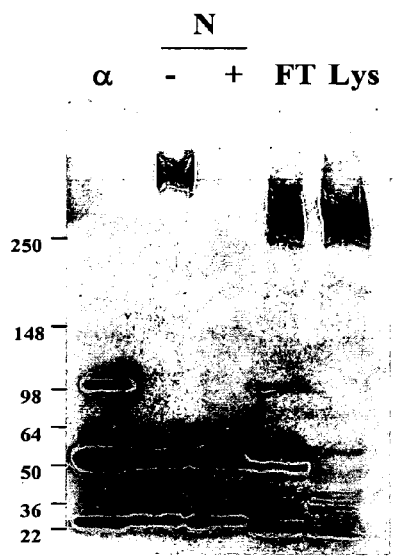
B. Caov-3
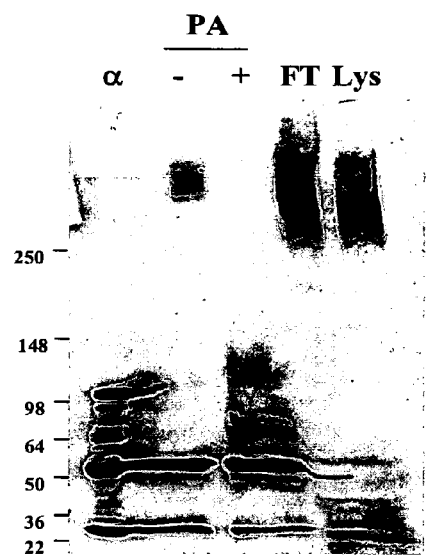
C. T-47D
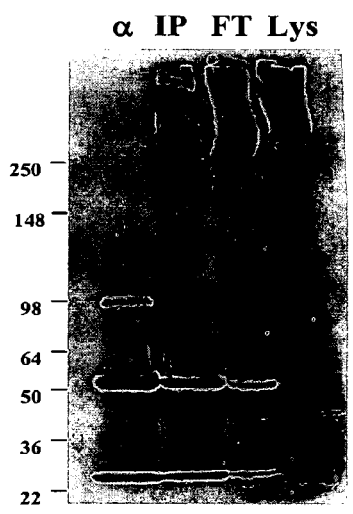
D. SK-OV-3
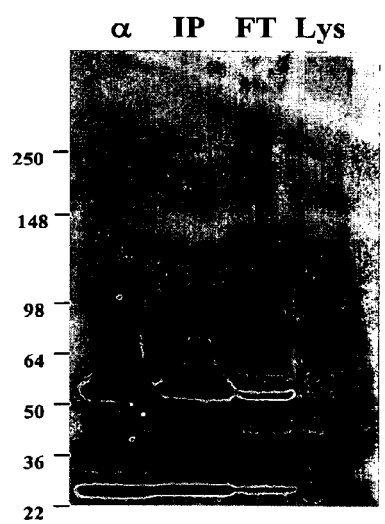

Figure 5 cont.
E. Colo205
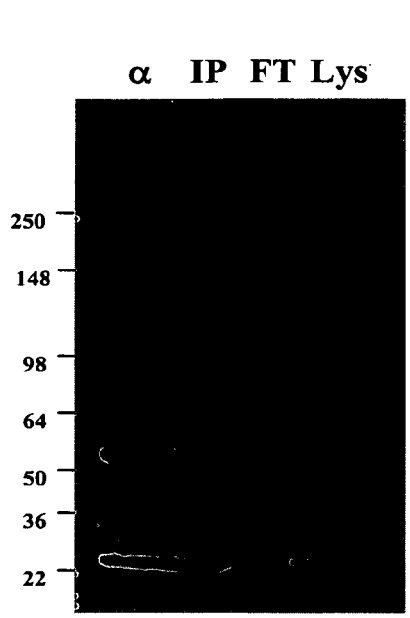
F. Caov-3
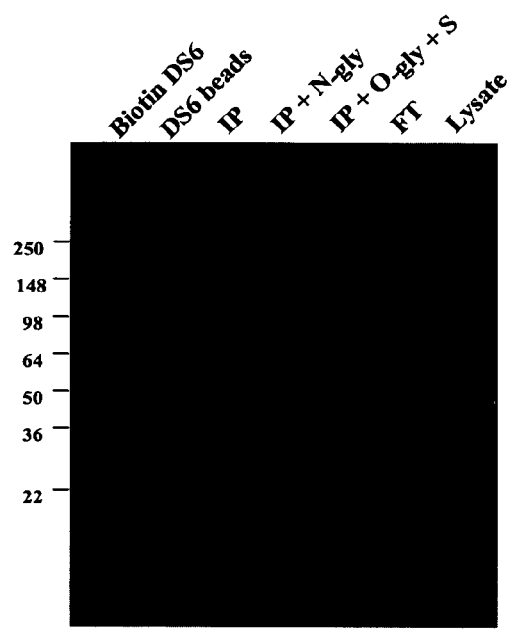

Figure 6
A. Caov-3
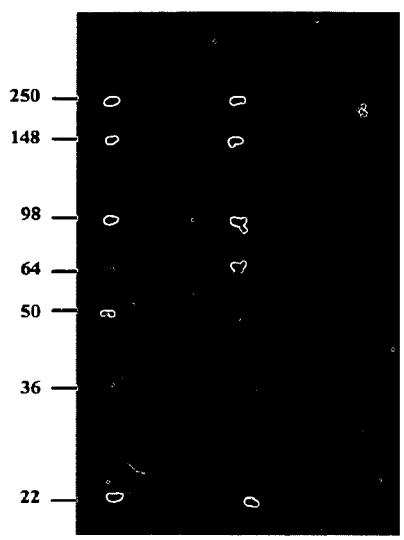
B. HeLa
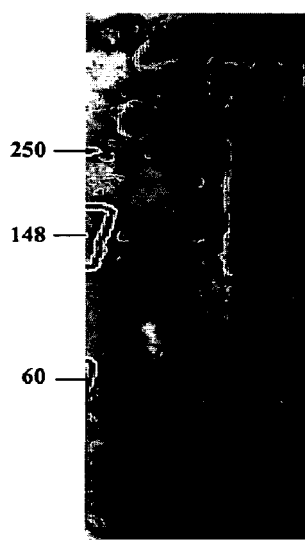 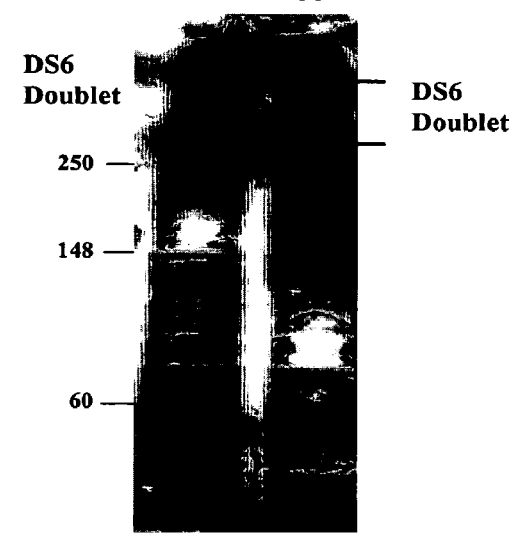

Figure 7
*Shed Antigen*
A.
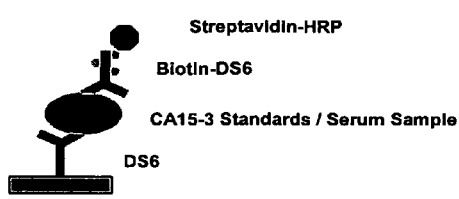
B.
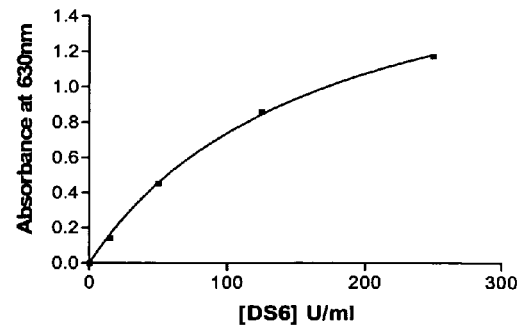
Figure 8
A. Standard 1
B. Standard 2
C. Detection Antibody Standard Curve
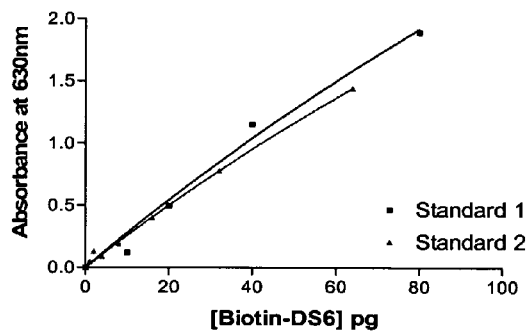

Figure 9

A. Light Chain - SEQ ID NO:7

```
          Q   I   V   L   T   Q   S   P   A   I   M   S   A   S   P   G   E
  1 CAAATTGTTC TCACCCAGTC TCCAGCAATC ATGTCTGCAT CTCCAGGGGA
                                                              CDR1
      K   V   T   I   T   C   S   A   H   S   S   V   S   F   M   H
 51 GAAGGTCACC ATAACCTGCA GTGCCCACTC AAGTGTAAGT TTCATGCACT

W   F   Q   Q   K   P   G   T   S   P   K   L   W   I   Y   S   T
101 GGTTCCAGCA GAAGCCAGGC ACTTCTCCCA AACTCTGGAT TTATAGCACA
        CDR2
      S   S   L   A   S   G   V   P   A   R   F   G   G   S   G   S   G
151 TCCAGCCTGG CTTCTGGAGT CCCTGCTCGC TTCGGTGGCA GTGGATCTGG

T   S   Y   S   L   T   I   S   R   M   E   A   E   D   A   A
201 GACCTCTTAC TCTCTCACAA TCAGCCGAAT GGAGGCTGAA GATGCTGCCA
                                          CDR3
      T   Y   Y   C   Q   Q   R   S   S   F   P   L   T   F   G   A   G
251 CTTATTACTG CCAGCAAAGG AGTAGTTTCC CGCTCACGTT CGGTGCTGGG

T   K   L   E   L   K   R
301 ACCAAGCTGG AGCTGAAACG T
```

B. Heavy Chain - SEQ ID NO:9

```
          Q   A   Y   L   Q   Q   S   G   A   E   L   V   R   S   G   A   S
  1 CAGGCTTATC TCCAGCAGTC TGGGGCTGAG CTGGTGAGGT CTGGGGCCTC
                                                                  CDR1
      V   K   M   S   C   K   A   S   G   Y   T   F   T   S   Y   N
 51 AGTGAAGATG TCCTGCAAGG CTTCTGGCTA CACATTTACC AGTTACAATA

M   H   W   V   K   Q   T   P   G   Q   G   L   E   W   I   G   Y
101 TGCACTGGGT AAAGCAGACA CCTGGACAGG GCCTGGAATG GATTGGATAT
        CDR2
      I   Y   P   G   N   G   A   T   N   Y   N   Q   K   F   K   G   K
151 ATTTATCCTG GAAATGGTGC TACTAACTAC AATCAGAAGT TCAAGGGCAA

A   T   L   T   A   D   P   S   S   S   T   A   Y   M   Q   I
201 GGCCACATTG ACTGCAGACC CATCCTCCAG CACAGCCTAC ATGCAGATCA

S   S   L   T   S   E   D   S   A   V   Y   F   C   A   R   G   D
251 GCAGCCTGAC ATCTGAAGAC TCTGCGGTCT ATTTCTGTGC AAGAGGAGAT
        CDR3
      S   V   P   F   A   Y   W   G   Q   G   T   L   V   T   V   S   A
301 TCGGTCCCGT TTGCTTACTG GGGCCAAGGG ACTCTTGTCA CTGTCTCTGC A
```

Figure 10

A. Light Chain

CDR1: S A H S S V S F M H - SEQ ID NO:4

CDR2: S T S S L A S - SEQ ID NO:5

CDR3: Q Q R S S F P L T - SEQ ID NO:6

B. Heavy Chain

CDR1: S Y N M H - SEQ ID NO:1

CDR2: Y I Y P G N G A T N Y N Q K F K G - SEQ ID NO:2

CDR3: G D S V P F A Y - SEQ ID NO:3

C. AbM Heavy Chain

CDR1: G Y T F T S Y N M H - SEQ ID NO:20

CDR2: Y I Y P G N G A T N - SEQ ID NO:21

CDR3: G D S V P F A Y - SEQ ID NO:22

Figure 11

Light Chain

```
               1                                                  50
IgVKap4   (1)  QIVLTQSPAIMSASPGEKVTITCSASSSVSMMHWFQQKPGTSPKLWIYST
muDS6LC   (1)  QIVLTQSPAIMSASPGEKVTITCSAHSSVSEMHWFQQKPGTSPKLWIYST 51                                             95
IgVKap4   (51) SNLASGVPARFSGSGSGTSYSLTISRMEAEDAATYYCQQRSSMPP
muDS6LC   (51) SSLASGVPARFGGSGSGTSYSLTISRMEAEDAATYYCQQRSSSPL
```

Heavy Chain

```
               1                                                  50
IgVh J558.41 (1) QAYLQQSGAELVRSGASVKMSCKASGYTFTSYNMHWVKQTPGQGLEWIGY
    muDS6HC  (1) QAYLQQSGAELVRSGASVKMSCKASGYTFTSYNMHWVKQTPGQGLEWIGY 51                                                 98
IgVh J558.41 (51) IYPGNGGTNYNQKFKGKATLTADTSSSTAYMQISSLTSEDSAVYFCAR
    muDS6HC  (51) IYPGNGATNYNQKFKGKATLTADESSSTAYMQISSLTSEDSAVYFCAR
```

Figure 12

Light Chain Ten Most Homologous Sequences with Structures

```
                   1                                                          60
muDS6LC    (1)  QIVLTQSPAIMSASPGEKVTITCSAHS--SVSFMHWFQQKPGTSPKLWIYSTSSLASGVP
   1for    (1)  QIVLTQSPAIMSAFPGEKVTITCSATS--SVNYMHWFQQKPGTSPKLWIYSSSNLASGVP
   1psk    (1)  XIVLTQSPAIMSASPGEKVTITCSASS--SVSNIHWFQQKPGTFPKLWIYSTSTLASGVP
   1ay1    (1)  DIQMTQSPAIMSASPGEKVTMTCSASS--SVSYMYWYQQKPGSSPRLLIYDSTNLASGVP
   1baf    (1)  QIVLTQSPAIMSASPGEKVTMTCSASS--SVYYMYWYQQKPGSSPRLLIYDTSNLASGVP
   1mim    (1)  QIVSTQSPAIMSASPGEKVTMTCSASSSRS--YMQWYQQKPGTSPKRWIYDTSKLASGVP
   1clo    (1)  QTVLSQSPAILSASPGEKVTMTCRASS--SVTYIHWYQQKPGSSPKSWIYATSNLASGVP
   1a6t    (1)  QSVLSQSPAILSASPGEKVIMTCSPSS--SVSYMQWYQQKPGSSPKPWIYSTSNLASGVP
   1fig    (1)  ENVLTQSPAIMSASPGEKVTMACRASSSVSSTYLHWYQQKSGASPKLLIYSTSNLASGVP
   15c8    (1)  DIVLTQSPAIMSASLGERVTMTCTASSSVSSSNLHWYQQKPGSSPKLWIYSTSNLASGVP
   1iai    (1)  DIQLTQSPAFMAASPGEKVTITCSVSSSISSSNLHWYQQKSETSPKPWIYGTSNLASGVP 61                                                       111
muDS6LC   (59)  ARFGGSGSGTSYSLTISRMEAEDAATYYCQQRSSFP-LTFGAGTKLELK--   (SEQ ID NO:7)
   1for   (59)  ARFSGSGSGTSYSLTISRMEAEDAATYYCQQRSSYP-ITFGSGTKLEIKR-   (SEQ ID NO:44)
   1psk   (59)  GRFSGSGSGTSYSLTISRMGAEDAATYYCQQRSGYP-FTFGSGTKLEIKR-   (SEQ ID NO:45)
   1ay1   (59)  VRFSGSGSGTSYSLTISRMEAEDAATYYCQQWSTYP-LTFGAGTKLELKR-   (SEQ ID NO:46)
   1baf   (59)  VRFSGSGSGTSYSLTISRMEAEDAATYYCQQWSSYPPITFGVGTKLELKR-   (SEQ ID NO:47)
   1mim   (59)  ARFSGSGSGTSYSLTISSMEAEDAATYYCHQRSS---YTFGGGTKLEIKR-   (SEQ ID NO:48)
   1clo   (59)  ARFSGSGSGTSYSLTISRVEAEDAATYYCQHWSSKP-PTFGGGTKLEIKR-   (SEQ ID NO:49)
   1a6t   (59)  GRFSGGGSGTSFSLTISGVEAEDAATYYCQQYSSHP-LTFGGGTKLELKR-   (SEQ ID NO:50)
   1fig   (61)  ARFSGSGSGTSYSLTISSVEAEDAATYYCQQYSGYP-LTFGAGTKLELKR-   (SEQ ID NO:51)
   15c8   (61)  ARFSGSGSGTSYSLTISSMEAEDAATYYCHQYHRSP-YTFGGGTKLEIKRA   (SEQ ID NO:52)
   1iai   (61)  VRFSGSGSGTSYSLTISSMEAEDAATYYCQQWNSYP-YTFGGGTKLEIKR-   (SEQ ID NO:53)
```

Heavy Chain Ten Most Homologous Sequences with Structures

```
                   1                                                                70
muDS6HC    (1)  QAYLQQSGAELVRSGASVKMSCKASGYTFTSYNMHWVKQTPGQGLEWIGYIYPGNGATNYNQKFKGKATL
   1PLG    (1)  QIQLQQSGPELVRPGASVKISCKASGYTFTDYYIHWVKQRPGEGLEWIGWIYPGSGNTKYNEKFKDKATL
   1NMB    (1)  QVQLQQPGAELVKPGASVRMSCKASGYTFTNYNMYWVKQSPGQGLEWIGIFYPGNGDTSYNQKFKDKATL
   1FOR    (1)  QGQLQQSGAELVRPGSSVKISCKASGYAFSSFWVNWVKQRPGQGLEWIGQIYPGDGDNKYNGKFKGKATL
   1NQB    (1)  QVQLQQSGAELVKPGASVKLSCKASGYTFTSYWMHWVKQRPGRGLEWIGRIDPNSGGTKYNEKFKSKATL
   6FAB    (1)  EVQLQQSGVELVRAGSSVKMSCKASGYTFTSNGINWVKQRPGQGLEWIGYNNPGNGYIAYNEKFKGKTTL
   1AE6    (1)  QIQLQQSGPELVKPGASVKISCKASGYTFTDYYINWMKQKPGQGLEWIGWIDPGSGNTKYNEKFKGKATL
   1D5B    (1)  QVQLQQSGAELMKPGASVKISCKATGYTFSSFWIEWVKQRPGHGLEWIGEILPGSSGGTHYNEKFKGKATF
   1FAI    (1)  QVQLQQSGAELVRAGSSVKMSCKASGYTFTSYGVNWVKQRPGQGLEWIGYINPGKGYLSYNEKFKGKTTL
   1MLB    (1)  QVQLQESGAEVMKPGASVKISCKATGYTFSTYWIEWVKQRPGHGLEWIGEILPGSGSTYYNEKFKGKATF
   1JHL    (1)  QVQLQQSGAELVRPGASVKLSCKASGYTFISYWINWVKQRPGQGLEWIGNIYPSDSYTNYNQKFKDKATL 71                                         124
muDS6HC   (71)  TADPSSSTAYMQISSLTSEDSAVYFCARGDSVP------FA-YWGQGTLVTVSA   (SEQ ID NO:9)
   1PLG   (71)  TVDTSSSTAYMQLSSLTSEDSAVYFCARGGK-------FAMDYWGQGTSVTVSS   (SEQ ID NO:54)
   1NMB   (71)  TADKSSNTAYMQLSSLTSEDSAVYYCARSGGSYRY--DGGFDYWGQGTTLTVSS   (SEQ ID NO:55)
   1FOR   (71)  TADKSSTTAYMQLYSLTSEDSAVYFCARSGN-Y----PYAMDYWGQGTSVTVSS   (SEQ ID NO:56)
   1NQB   (71)  TVDKPSSTAYMQLSSLTSEDSAVYYCARYDYYGS----SYFDYWGQGTTVTVSS   (SEQ ID NO:57)
   6FAB   (71)  TVDKSSSTAYMQLRSLTSEDSAVYFCARSEYYG---GSYKFDYWGQGTTLTVSS   (SEQ ID NO:58)
   1AE6   (71)  TVDTSSSTAYMQLSSLTSEDTAVYFCAREKTTY----YYAMDYWGQGTSVTVSA   (SEQ ID NO:59)
   1D5B   (71)  TADKSSNTAYMQLSSLTSEDSAVYYCARGHSYYFY--DG--DYWGQGTSVTVSS   (SEQ ID NO:60)
   1FAI   (71)  TVDRSSSTAYMQLRSLTSEDAAVYFCARSFYGGSDLAVYYFDSWGQGTTLTVSS   (SEQ ID NO:61)
   1MLB   (71)  TADTSSNTAYMQLSSLTSEDSAVYYCARGDGNYG-------YWGQGTTLTVSS   (SEQ ID NO:62)
   1JHL   (71)  TVDKSSSTAYMQLSSPTSEDSAVYYCTRDDNYG------AMDYWGQGTTVTV--   (SEQ ID NO:63)
```

Figure 13A
A. muDS6 Light Chain Surface Calculations

| 25-35 | ave % acc | >30 | 25-35 | flank | surf | Kabat No | SR no | SR surf | seq | ave % acc | >30 | 25-35 | flank | surf | Kabat No | SR no | SR surf |
|---|---|---|---|---|---|---|---|---|---|---|---|---|---|---|---|---|---|
| Q | 53.59 | 1 | | | 1 | 1 | 2 | 2 | P | 19.01 | | | | | 59 | 66 | |
| I | 4.63 | | | | | 2 | 3 | | A | 47.39 | 60 | | | 60 | 60 | 67 | 67 |
| V | 35.63 | 3 | | | 3 | 3 | 4 | 4 | R | 15.49 | | | | | 61 | 68 | |
| L | 4.02 | | | | | 4 | 5 | | F | 2.19 | | | | | 62 | 69 | |
| T | 30.41 | 5 | *??* | 33.144 | 5 | 5 | 6 | 6 | G | 25.02 | | *??* | 0 | | 63 | 70 | |
| Q | 7.10 | | | | | 6 | 7 | | G | 7.03 | | | | | 64 | 71 | |
| S | 29.08 | | *??* | 29.604 | | 7 | 8 | | S | 26.00 | | *??* | 28.46 2 | | 65 | 72 | |
| P | 21.80 | | | | | 8 | 9 | | G | 19.35 | | | | | 66 | 73 | |
| A | 31.98 | 9 | *??* | 31.567 | 9 | 9 | 10 | 10 | S | 38.04 | 67 | | | 67 | 67 | 74 | 74 |
| I | 37.67 | 10 | | | 10 | 10 | 11 | 11 | G | 17.95 | | | | | 68 | 75 | |
| M | 14.99 | | | | | 11 | 12 | | T | 24.68 | | | | | 69 | 76 | |
| S | 27.16 | | *??* | 26.2 | | 12 | 13 | | S | 28.93 | | *??* | 28.05 9 | | 70 | 77 | |
| A | 1.99 | | | | | 13 | 14 | | Y | 1.55 | | | | | 71 | 78 | |
| S | 17.20 | | | | | 14 | 15 | | S | 12.99 | | | | | 72 | 79 | |
| P | 34.43 | 15 | *??* | 33.573 | 15 | 15 | 16 | 16 | L | 0.03 | | | | | 73 | 80 | |
| G | 23.43 | | | | | 16 | 17 | | T | 10.88 | | | | | 74 | 81 | |
| E | 25.59 | | *??* | 25.601 | | 17 | 18 | | I | 0.06 | | | | | 75 | 82 | |
| K | 45.67 | 18 | | | 18 | 18 | 19 | 19 | S | 24.84 | | | | | 76 | 83 | |
| V | 2.97 | | | | | 19 | 20 | | R | 32.14 | 77 | *??* | 46.08 7 | 77 | 77 | 84 | 84 |
| T | 28.62 | | *??* | 26.845 | | 20 | 21 | | M | 0.87 | | | | | 78 | 85 | |
| I | 0.79 | | | | | 21 | 22 | | E | 24.97 | | | | | 79 | 86 | |
| T | 20.78 | | | | | 22 | 23 | | A | 30.52 | 80 | *??* | 27.85 | | 80 | 87 | |
| C | 0.13 | | | | | 23 | 24 | | E | 36.62 | 81 | | | 81 | 81 | 88 | 88 |
| S | 25.91 | | *??* | | | 24 | 25 | | D | 1.24 | | | | | 82 | 89 | |
| A | 3.25 | | | | | 25 | 26 | | A | 17.79 | | | | | 83 | 90 | |
| H | 31.44 | 26 | *??* | | | 26 | 27 | | A | 3.37 | | | | | 84 | 91 | |
| S | 28.15 | | *??* | | | 27 | 28 | | T | 11.19 | | | | | 85 | 92 | |
| S | 33.75 | 27A | *??* | | | 27A | 29 | | Y | 0.05 | | | | | 86 | 93 | |
| V | 5.59 | | | | | 27B | 30 | | Y | 4.28 | | | | | 87 | 94 | |
| S | 32.25 | 27C | *??* | | | 27C | 31 | | C | 0.04 | | | | | 88 | 95 | |
| | 8.34 | | | | | 27D | 32 | | Q | 1.16 | | | | | 89 | 96 | |
| | 3.70 | | | | | 27E | 33 | | Q | 0.23 | | | | | 90 | 97 | |
| | 0.00 | | | | | 27F | 34 | | R | 16.47 | | | | | 91 | 98 | |
| | 0.00 | | | | | 28 | 35 | | S | 22.54 | | | | | 92 | 99 | |
| | 0.00 | | | | | 29 | 36 | | S | 23.05 | | | | | 93 | 100 | |
| | 0.00 | | | | | 30 | 37 | | | 3.13 | | | | | 94 | 101 | |
| | 0.00 | | | | | 31 | 38 | | | 0.89 | | | | | 95 | 102 | |
| F | 22.65 | | | | | 32 | 39 | | F | 22.65 | | | | | 95E | 107 | |
| M | 0.10 | | | | | 33 | 40 | | P | 9.70 | | | | | 95F | 108 | |
| H | 2.53 | | | | | 34 | 41 | | L | 6.52 | | | | | 96 | 109 | |
| W | 0.30 | | | | | 35 | 42 | | T | 11.97 | | | | | 97 | 110 | |
| F | 1.13 | | | | | 36 | 43 | | F | 6.15 | | | | | 98 | 111 | |
| Q | 3.34 | | | | | 37 | 44 | | G | 1.68 | | | | | 99 | 112 | |
| Q | 8.68 | | | | | 38 | 45 | | A | 28.73 | | *??* | 20.74 | | 100 | 113 | |
| K | 22.43 | | | | | 39 | 46 | | G | 4.48 | | | | | 101 | 114 | |
| P | 50.62 | 40 | | | 40 | 40 | 47 | 47 | T | 0.10 | | | | | 102 | 115 | |
| G | 44.24 | 41 | | | 41 | 41 | 48 | 48 | K | 29.39 | | *??* | 29.57 3 | | 103 | 116 | |
| T | 25.08 | | *??* | 29.575 | | 42 | 49 | | L | 1.15 | | | | | 104 | 117 | |
| S | 15.21 | | | | | 43 | 50 | | E | 27.47 | | *??* | 27.17 | | 105 | 118 | |
| P | 2.56 | | | | | 44 | 51 | | L | 21.66 | | | | | 106 | 119 | |
| K | 27.85 | | *??* | 29.675 | | 45 | 52 | | K | 35.78 | 107 | | | 107 | 107 | 121 | 121 |
| L | 9.44 | | | | | 46 | 53 | | | | | | | | | | |
| W | 5.39 | | | | | 47 | 54 | | | | | | | | | | |
| I | 0.34 | | | | | 48 | 55 | | | | | | | | | | |
| Y | 17.69 | | | | | 49 | 56 | | | | | | | | | | |
| S | 13.01 | | | | | 50 | 57 | | | | | | | | | | |
| T | 5.88 | | | | | 51 | 58 | | | | | | | | | | |
| S | 29.44 | | *??* | | | 52 | 59 | | | | | | | | | | |
| S | 26.16 | | *??* | | | 53 | 60 | | | | | | | | | | |
| L | 22.15 | | | | | 54 | 61 | | | | | | | | | | |
| A | 9.25 | | | | | 55 | 62 | | | | | | | | | | |
| S | 51.26 | 56 | | | | 56 | 63 | | | | | | | | | | |
| G | 38.57 | 57 | | | 57 | 57 | 64 | 64 | | | | | | | | | |
| V | 8.76 | | | | | 58 | 65 | | | | | | | | | | |

Figure 13B

B. muDS6 Heavy Chain Surface Calculations

| seq | Ave % acc | >30 | 25-35 | flank | surf | Kabat No | SR no | SR surf | seq | Ave % acc | >30 | 25-35 | flank | surf | Kabat No | SR no | SR surf |
|---|---|---|---|---|---|---|---|---|---|---|---|---|---|---|---|---|---|
| Q | 64.68 | 1 | | | 1 | 1 | 2 | 2 | K | 39.08 | 64 | | | 64 | 64 | 70 | 70 |
| A | 15.65 | | | | | 2 | 3 | | G | 39.4 | 65 | | | 65 | 65 | 71 | 71 |
| Y | 31.88 | 3 | *??* | 31.88 | 3 | 3 | 4 | 4 | K | 16.66 | | | | | 66 | 72 | |
| L | 4.156 | | | | | 4 | 5 | | A | 2.096 | | | | | 67 | 73 | |
| Q | 29.83 | | *??* | 30.16 | 5 | 5 | 6 | 6 | T | 25.55 | | *??* | 28.08 | | 68 | 74 | |
| Q | 5.146 | | | | | 6 | 7 | | L | 3.639 | | | | | 69 | 75 | |
| S | 21.64 | | | | | 7 | 8 | | T | 25.85 | | *??* | 29.56 | | 70 | 76 | |
| G | 20.31 | | | | | 8 | 9 | | A | 13.24 | | | | | 71 | 77 | |
| A | 36.19 | 9 | | | 9 | 9 | 10 | 10 | D | 21.35 | | | | | 72 | 78 | |
| E | 21.29 | | | | | 10 | 11 | | P | 36.15 | 73 | | | 73 | 73 | 79 | 79 |
| L | 49.11 | 11 | | | 11 | 11 | 12 | 12 | S | 48.82 | 74 | | | 74 | 74 | 80 | 80 |
| V | 10.25 | | | | | 12 | 13 | | S | 24.62 | | | | | 75 | 81 | |
| R | 50.21 | 13 | | | 13 | 13 | 14 | 14 | S | 15.41 | | | | | 76 | 82 | |
| S | 34.2 | 14 | *??* | 34.2 | 14 | 14 | 15 | 15 | T | 5.116 | | | | | 77 | 83 | |
| G | 29.89 | | *??* | 29.73 | | 15 | 16 | | A | 0.488 | | | | | 78 | 84 | |
| A | 18.34 | | | | | 16 | 17 | | Y | 15.94 | | | | | 79 | 85 | |
| S | 25.54 | | *??* | 27.06 | | 17 | 18 | | M | 0.282 | | | | | 80 | 86 | |
| V | 4.2 | | | | | 18 | 19 | | Q | 22.29 | | | | | 81 | 87 | |
| K | 36.48 | 19 | | | 19 | 19 | 20 | 20 | I | 1.738 | | | | | 82 | 88 | |
| M | 0.813 | | | | | 20 | 21 | | S | 20.72 | | | | | 82A | 89 | |
| S | 13.11 | | | | | 21 | 22 | | S | 31.21 | 82B | *??* | 31.18 | 82B | 82B | 90 | 90 |
| C | 0.529 | | | | | 22 | 23 | | L | 0.63 | | | | | 82C | 91 | |
| K | 29.41 | | *??* | 31.16 | 23 | 23 | 24 | 24 | T | 26.26 | | *??* | 26.39 | | 83 | 92 | |
| A | 3.823 | | | | | 24 | 25 | | S | 35.72 | 84 | | | 84 | 84 | 93 | 93 |
| S | 21.79 | | | | | 25 | 26 | | E | 38.86 | 85 | | | 85 | 85 | 94 | 94 |
| G | 26.57 | | *??* | | | 26 | 27 | | D | 3.913 | | | | | 86 | 95 | |
| Y | 13.69 | | | | | 27 | 28 | | S | 14.42 | | | | | 87 | 96 | |
| T | 34.52 | 28 | *??* | | | 28 | 29 | | A | 2.996 | | | | | 88 | 97 | |
| F | 3.192 | | | | | 29 | 30 | | V | 16.13 | | | | | 89 | 98 | |
| T | 22.22 | | | | | 30 | 31 | | Y | 1.019 | | | | | 90 | 99 | |
| S | 28.17 | | *??* | | | 31 | 32 | | F | 2.811 | | | | | 91 | 100 | |
| Y | 0 | | | | | 32 | 33 | | C | 0 | | | | | 92 | 101 | |
| N | 0 | | | | | 33 | 34 | | A | 0.198 | | | | | 93 | 102 | |
| M | 14.35 | | | | | 34 | 35 | | R | 5.789 | | | | | 94 | 103 | |
| H | 11.38 | | | | | 35 | 36 | | G | 2.404 | | | | | 95 | 104 | |
| | 0.63 | | | | | 35A | 37 | | D | 15.92 | | | | | 96 | 105 | |
| | 1.018 | | | | | 35B | 38 | | S | 25.28 | | *??* | | | 97 | 106 | |
| W | 0.18 | | | | | 36 | 39 | | V | 29.64 | | *??* | | | 98 | 107 | |
| V | 0.5 | | | | | 37 | 40 | | P | 23.57 | | | | | 99 | 108 | |
| K | 5.459 | | | | | 38 | 41 | | | 18.79 | | | | | 100 | 109 | |
| Q | 10.08 | | | | | 39 | 42 | | | 12.87 | | | | | 100A | 110 | |
| T | 22.08 | | | | | 40 | 43 | | | 10.47 | | | | | 100B | 111 | |
| P | 46.17 | 41 | | | 41 | 41 | 44 | 44 | | 2.039 | | | | | 100C | 112 | |
| G | 43.05 | 42 | | | 42 | 42 | 45 | 45 | | 2.919 | | | | | 100D | 113 | |
| Q | 42.17 | 43 | | | 43 | 43 | 46 | 46 | | 0.252 | | | | | 100E | 114 | |
| G | 11.9 | | | | | 44 | 47 | | | 0.522 | | | | | 100F | 115 | |
| L | 6.039 | | | | | 45 | 48 | | | 0 | | | | | 100G | 116 | |
| E | 19.21 | | | | | 46 | 49 | | | 0 | | | | | 100H | 117 | |
| W | 1.433 | | | | | 47 | 50 | | F | 0.721 | | | | | 101 | 120 | |
| I | 0.123 | | | | | 48 | 51 | | A | 12.13 | | | | | 102 | 121 | |
| G | 0 | | | | | 49 | 52 | | Y | 24.24 | | | | | 103 | 122 | |
| Y | 4.983 | | | | | 50 | 53 | | W | 7.003 | | | | | 104 | 123 | |
| I | 2.466 | | | | | 51 | 54 | | G | 1.847 | | | | | 105 | 124 | |
| Y | 13.72 | | | | | 52 | 55 | | Q | 36.46 | 106 | | | 106 | 106 | 125 | 125 |
| P | 2.199 | | | | | 52A | 56 | | G | 7.55 | | | | | 107 | 126 | |
| | 22.06 | | | | | 52B | 57 | | T | 1.036 | | | | | 108 | 127 | |
| | 39.1 | 52C | | | | 52C | 58 | | L | 25.8 | | *??* | 25.8 | | 109 | 128 | |
| G | 25.76 | | *??* | | | 53 | 59 | | V | 1.059 | | | | | 110 | 129 | |
| N | 0 | | | | | 54 | 60 | | T | 25.56 | | *??* | 26.55 | | 111 | 130 | |
| G | 0 | | | | | 55 | 61 | | V | 7.217 | | | | | 112 | 131 | |
| A | 31.16 | 56 | *??* | | | 56 | 62 | | S | 41.66 | 113 | | | 113 | 113 | 132 | 132 |
| T | 22.29 | | | | | 57 | 63 | | A | | | | | | | | |
| N | 21.14 | | | | | 58 | 64 | | | | | | | | | | |
| Y | 14.28 | | | | | 59 | 65 | | | | | | | | | | |
| N | 6.902 | | | | | 60 | 66 | | | | | | | | | | |
| Q | 47.15 | 61 | | | 61 | 61 | 67 | 67 | | | | | | | | | |
| K | 43.58 | 62 | | | 62 | 62 | 68 | 68 | | | | | | | | | |
| F | 4.24 | | | | | 63 | 69 | | | | | | | | | | |

Figure 15

A. Light chain amino acid sequence (murine and human residue variability shaded)

```
Kabat #      1                                                  51
   muDS6LC   QIVLTQSPAIMSASPGEKVTITCSAHSSVSFMHWFQQKPGTSPKLWIYST
huDS6LC v1.01 EIVLTQSPATMSASPGERVTITCSAHSSVSFMHWFQQKPGTSPKLWIYST
huDS6LC v1.21 EIVLTQSPAIMSASPGERVTITCSAHSSVSFMHWFQQKPGTSPKLWIYST Kabat #      52                                                 101
   muDS6LC   SSLASGVPARFGGSGSGTSYSLTISRMEAEDAATYYCQQRSSFPLTFGAG
huDS6LC v1.01 SSLASGVPARFGGSGSGTSYSLTISSMEAEDAATYYCQQRSSFPLTFGAG
huDS6LC v1.21 SSLASGVPARFGGSGSGTSYSLTISSMEAEDAATYYCQQRSSFPLTFGAG Kabat #      102
   muDS6LC   TKLELKR - SEQ ID NO:7
huDS6LC v1.01 TKLELKR - SEQ ID NO:8
huDS6LC v1.21 TKLELKR - SEQ ID NO:8
```

B. Heavy chain amino acid sequence (murine and human residue variability shaded)

```
Kabat #      1                                                  50
   muDS6HC   QAYLQQSGAELVRSGASVKMSCKASGYTFTSYNMHWVKQTPGQGLEWIGY
huDS6HC v1.01 QAQLVQSGAEVVKPGASVKMSCKASGYTFTSYNMHWVKQTPGQGLEWIGY
huDS6HC v1.21 QAQLVQSGAEVVKPGASVKMSCKASGYTFTSYNMHWVKQTPGQGLEWIGY Kabat #      51                                              96
   muDS6HC   IYPGNGATNYNQKFKGKATLTADESSSTAYMQISSLTSEDSAVYFCARGD
huDS6HC v1.01 IYPGNGATNYNQKFQGKATLTADTSSSTAYMQISSLTSEDSAVYFCARGD
huDS6HC v1.21 IYPGNGATNYNQKFQGKATLTADESSSTAYMQISSLTSEDSAVYFCARGD Kabat #      97         114
   muDS6HC   SVPFAYWGQGTLVTVSA - SEQ ID NO:9
huDS6HC v1.01 SVPFAYWGQGTLVTVSA - SEQ ID NO:10
huDS6HC v1.21 SVPFAYWGQGTLVTVSA - SEQ ID NO:11
```

Figure 16 huDS6 Light Chain (v1.01 and v1.21) - SEQ ID NO:8

```
         E   I   V   L       T   Q   S       P   A   T       M   S   A   S       P   G   E
  1 GAGATTGTTC TCACCCAGTC TCCAGCAACC ATGTCTGCAT CTCCAGGGGA

R   V   T       I   T   C       S   A   H   S       S   V   S       F   M   H
 51 GAGGGTCACC ATAACCTGCA GTGCCCACTC AAGTGTAAGT TTCATGCACT

W   F   Q   Q       K   P   G       T   S   P   K       L   W   I   Y       S   T
101 GGTTCCAGCA GAAGCCAGGC ACTTCTCCCA AACTCTGGAT TTATAGCACA

S   S   L   A       S   G   V       P   A   R       F   G   G   S       G   S   G
151 TCCAGCCTGG CTTCTGGAGT CCCTGCTCGC TTCGGTGGCA GTGGATCTGG

T   S   Y       S   L   T   I       S   S   M       E   A   E       D   A   A
201 GACCTCTTAC TCTCTCACAA TCAGCAGCAT GGAGGCTGAA GATGCTGCCA

T   Y   Y   C       Q   Q   R       S   S   F   P       L   T   F       G   A   G
251 CTTATTACTG CCAGCAAAGG AGTAGTTTCC CGCTCACGTT CGGTGCTGGG

T   K   L   E       L   K   R
301 ACCAAGCTGG AGCTGAAACG T
```

Figure 17

A. huDS6 Heavy Chain v1.01 - SEQ ID NO:10

```
          Q   A   Q   L     V   Q   S   G   A     E   V   V   K   P     G   A   S
     1 CAGGCTCAGC TCGTGCAGTC TGGGGCTGAG GTGGTGAAGC CCGGGGCCTC

V   K   M       S   C   K   A   S   G   Y     T   F   T       S   Y   N
    51 AGTGAAGATG TCCTGCAAGG CTTCTGGCTA CACATTTACC AGTTACAATA

M   H   W   V     K   Q   T     P   G   Q   G     L   E   W     I   G   Y
   101 TGCACTGGGT AAAGCAGACA CCTGGACAGG GCCTGGAATG GATTGGATAT

I   Y   P   G     N   A     T   N   Y     N   Q   K   F     Q   G   K
   151 ATTTATCCTG GAAATGGTGC TACTAACTAC AATCAGAAGT TCCAGGGCAA

A   T   L       T   A   D   T     S   S   S       T   A   Y     M   Q   I
   201 GGCCACATTG ACTGCAGACA CATCCTCCAG CACAGCCTAC ATGCAGATCA

S   S   L   T     S   E   D     S   A   V   Y     F   C   A     R   G   D
   251 GCAGCCTGAC ATCTGAAGAC TCTGCGGTCT ATTTCTGTGC AAGAGGAGAT

S   V   P   F     A   Y   W     G   Q   G     T   L   V   T     V   S   A
   301 TCGGTCCCGT TTGCTTACTG GGGCCAAGGG ACTCTTGTCA CTGTCTCTGC

351 C
```

B. huDS6 Heavy Chain v1.21 - SEQ ID NO:11

```
          Q   A   Q   L     V   Q   S   G   A     E   V   V   K   P     G   A   S
     1 CAGGCTCAGC TCGTGCAGTC TGGGGCTGAG GTGGTGAAGC CCGGGGCCTC

V   K   M       S   C   K   A   S   G   Y     T   F   T       S   Y   N
    51 AGTGAAGATG TCCTGCAAGG CTTCTGGCTA CACATTTACC AGTTACAATA

M   H   W   V     K   Q   T     P   G   Q   G     L   E   W     I   G   Y
   101 TGCACTGGGT AAAGCAGACA CCTGGACAGG GCCTGGAATG GATTGGATAT

I   Y   P   G     N   A     T   N   Y     N   Q   K   F     Q   G   K
   151 ATTTATCCTG GAAATGGTGC TACTAACTAC AATCAGAAGT TCCAGGGCAA

A   T   L       T   A   D   P     S   S   S       T   A   Y     M   Q   I
   201 GGCCACATTG ACTGCAGACC CATCCTCCAG CACAGCCTAC ATGCAGATCA

S   S   L   T     S   E   D     S   A   V   Y     F   C   A     R   G   D
   251 GCAGCCTGAC ATCTGAAGAC TCTGCGGTCT ATTTCTGTGC AAGAGGAGAT

S   V   P   F     A   Y   W     G   Q   G     T   L   V   T     V   S   A
   301 TCGGTCCCGT TTGCTTACTG GGGCCAAGGG ACTCTTGTCA CTGTCTCTGC

351 C
```

Figure 22
A. HPAC
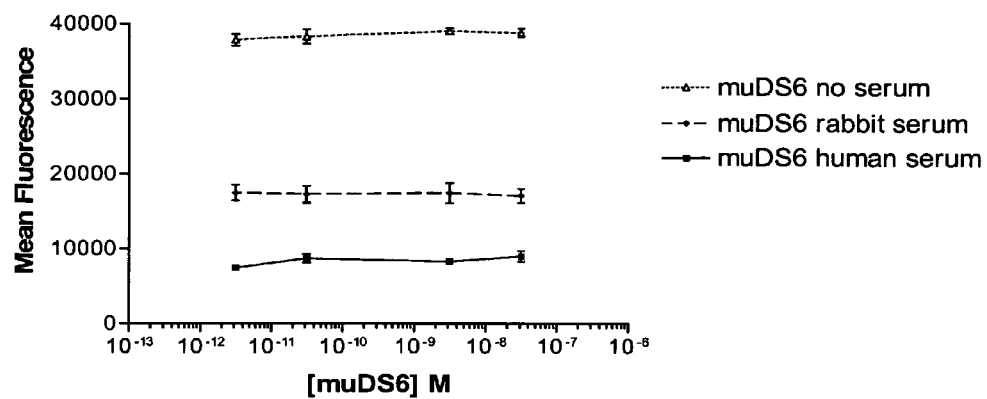
B. ZR-75-1
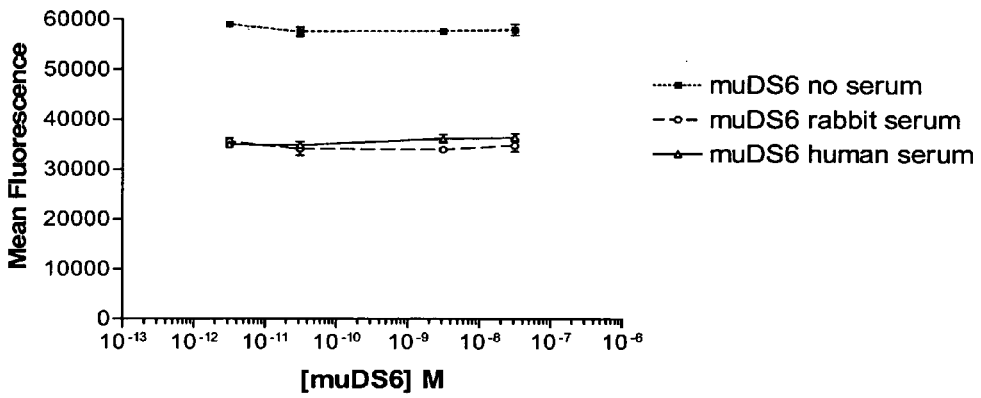

A. Human ovarian cancer cell lines

B. Human breast cancer cell lines

C. Human cervical cancer cell lines

D. Human pancreatic cancer cell lines

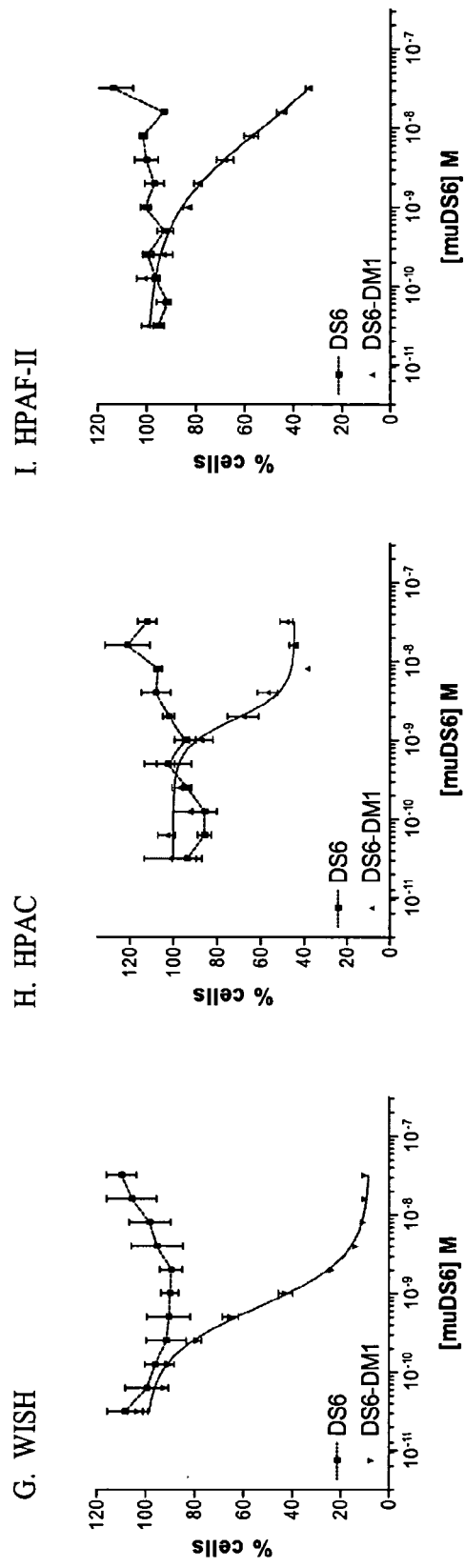

Figure 25
A.
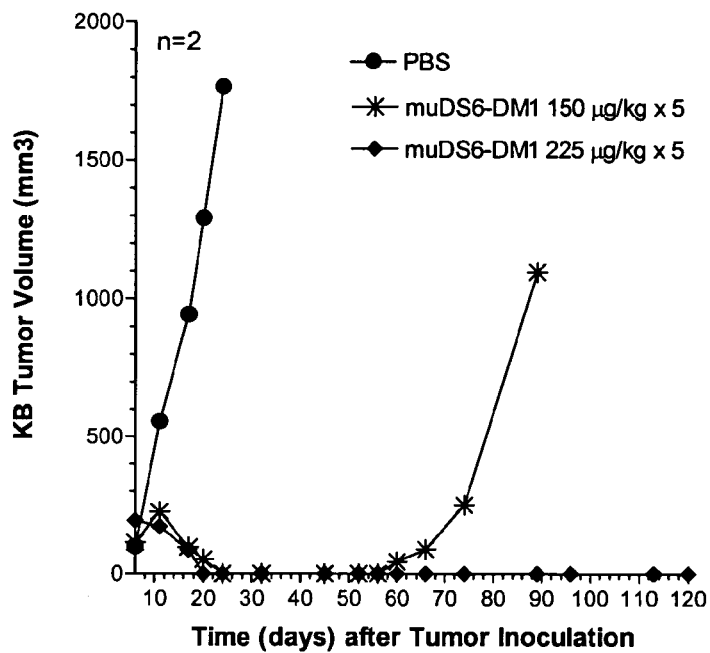
B.
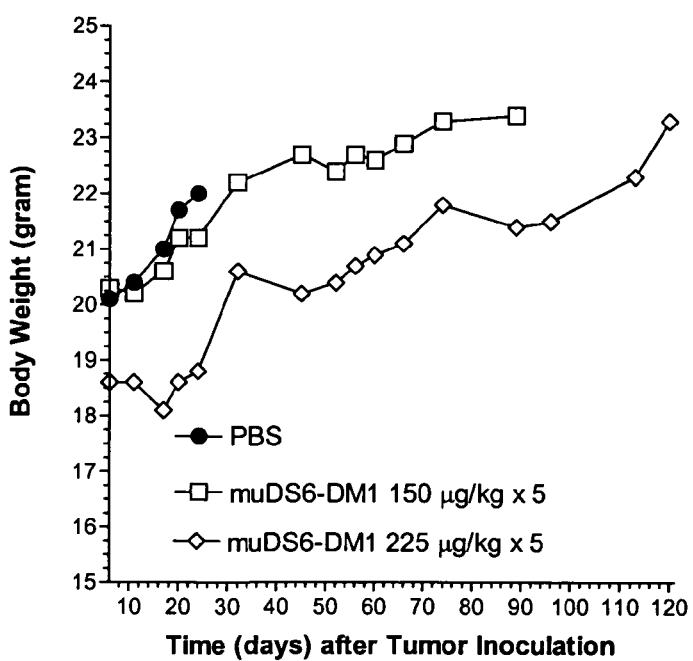

Figure 26
OVCAR5
A.
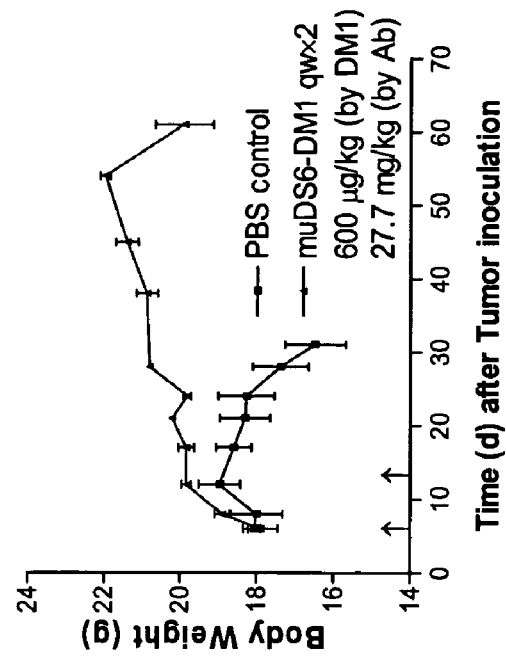
B.
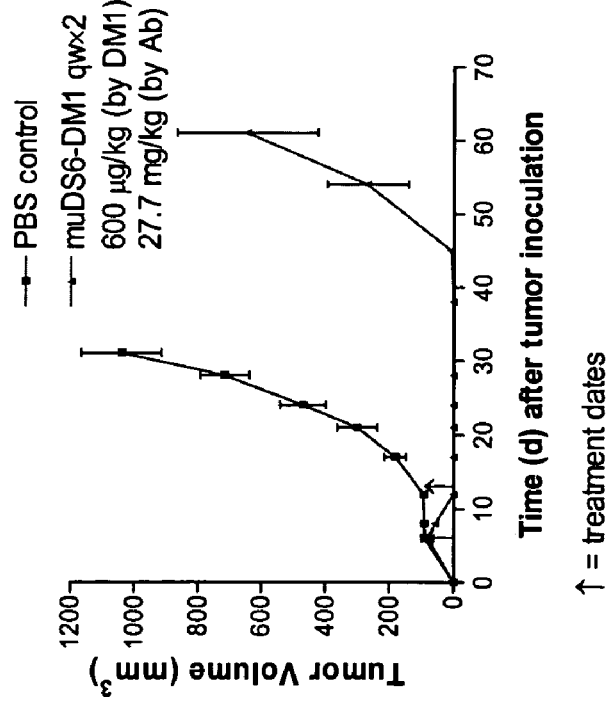
↑ = treatment dates

Figure 26 cont.
TOV-21G
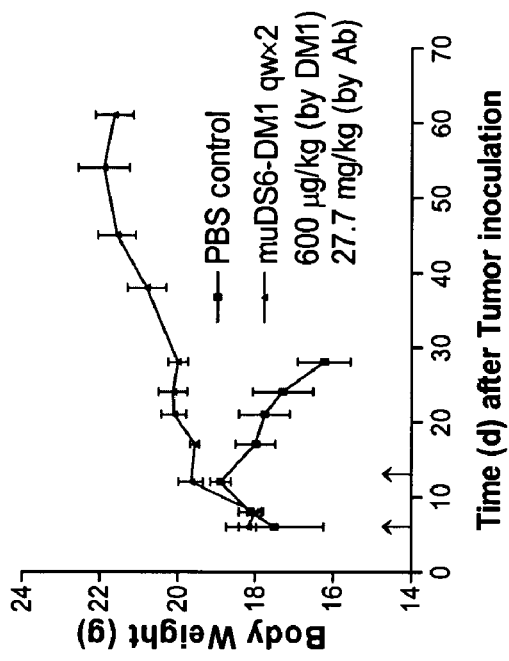
C.
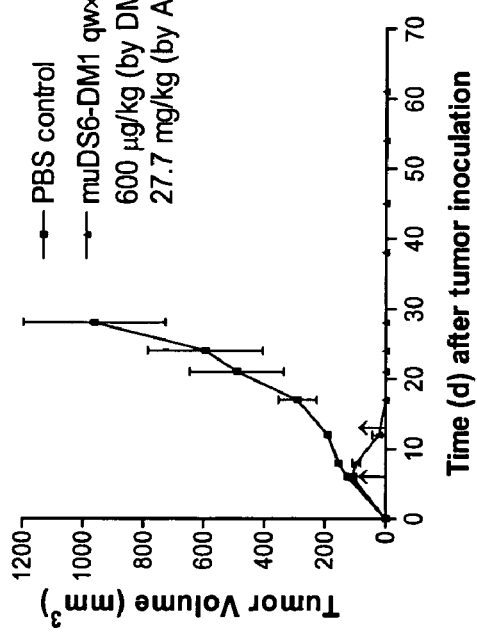
D.

Figure 26 cont.
HPAC
E.
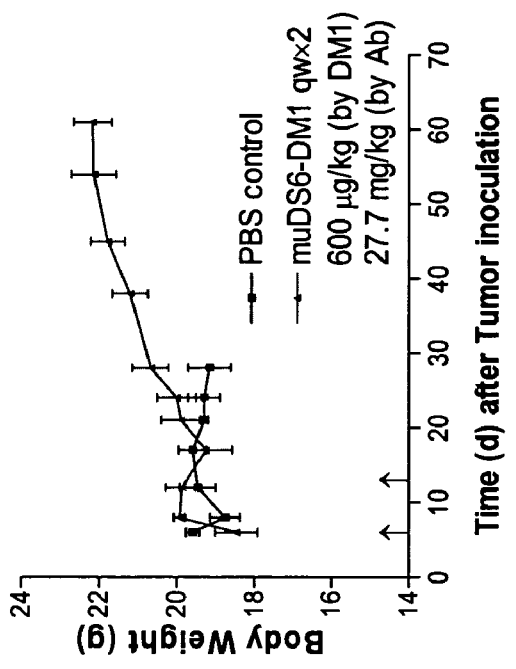
F.
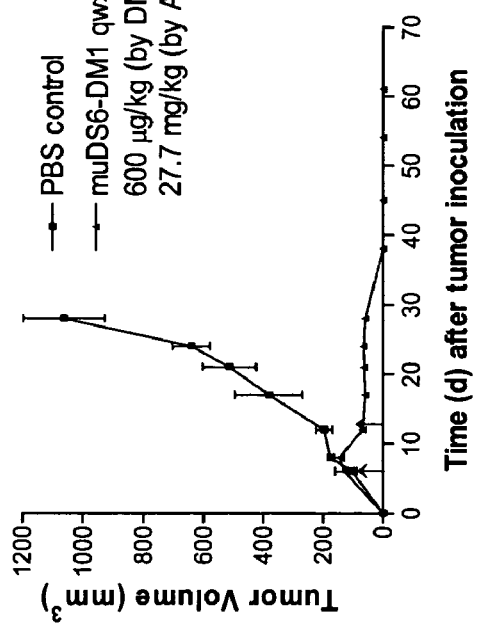

Figure 26 cont.
HeLa
G.
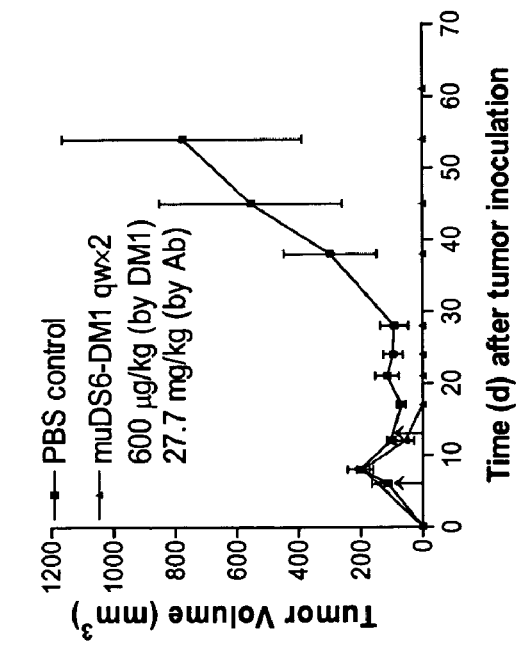
H.
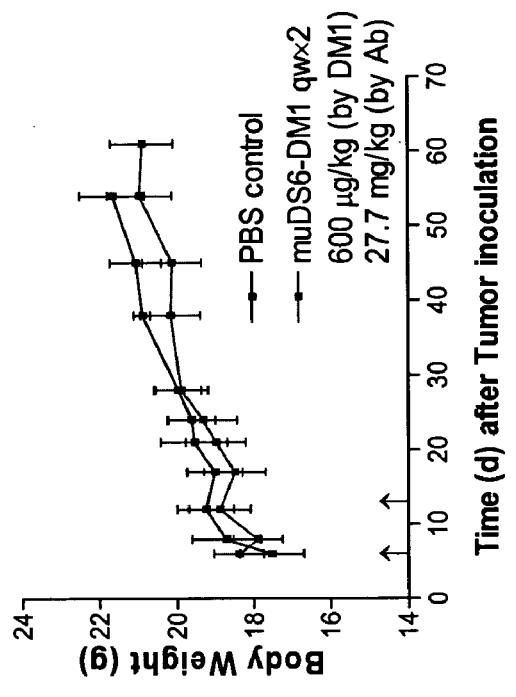

Figure 29
A.
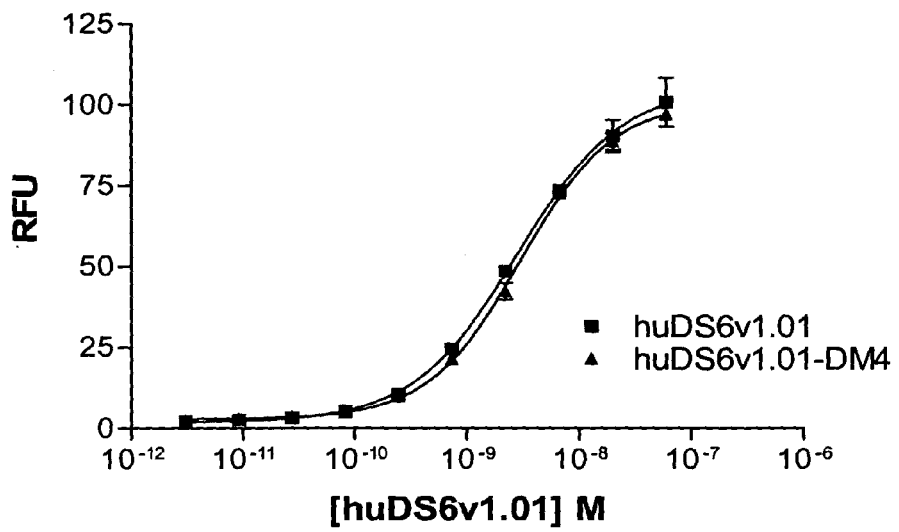
B.
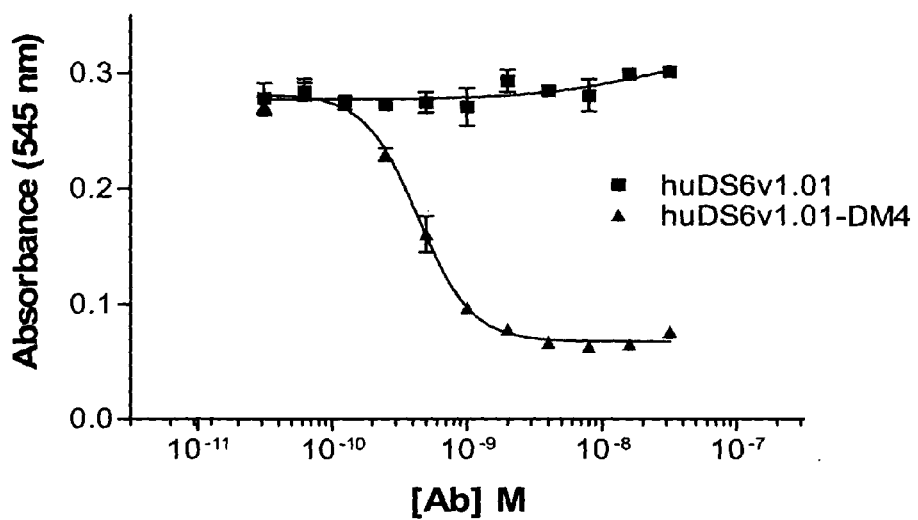

Figure 30
A.
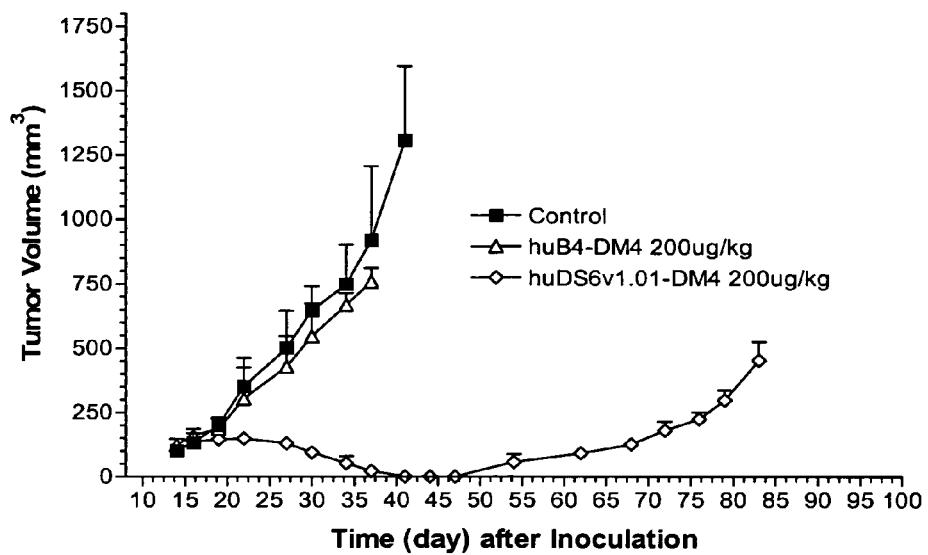
B.
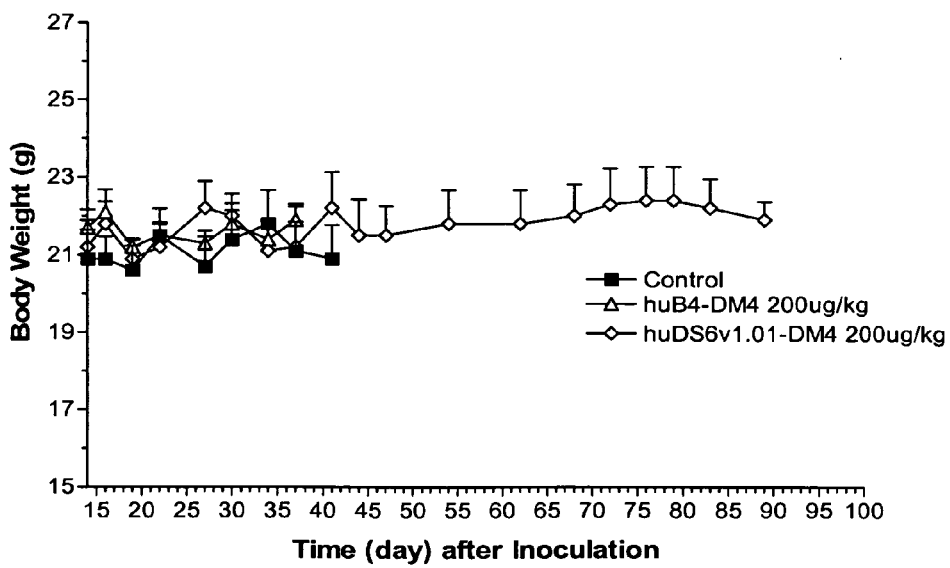

SEQUENCE LISTING

```
<160> NUMBER OF SEQ ID NOS: 63

<210> SEQ ID NO 1
<211> LENGTH: 5
<212> TYPE: PRT
<213> ORGANISM: Mus musculus

<400> SEQUENCE: 1

Ser Tyr Asn Met His
1               5

<210> SEQ ID NO 2
<211> LENGTH: 17
<212> TYPE: PRT
<213> ORGANISM: Mus musculus

<400> SEQUENCE: 2

Tyr Ile Tyr Pro Gly Asn Gly Ala Thr Asn Tyr Asn Gln Lys Phe Lys
1               5                   10                  15

Gly

<210> SEQ ID NO 3
<211> LENGTH: 8
<212> TYPE: PRT
<213> ORGANISM: Mus musculus

<400> SEQUENCE: 3

Gly Asp Ser Val Pro Phe Ala Tyr
1               5
```

```
<210> SEQ ID NO 4
<211> LENGTH: 10
<212> TYPE: PRT
<213> ORGANISM: Mus musculus

<400> SEQUENCE: 4

Ser Ala His Ser Ser Val Ser Phe Met His
1               5                   10

<210> SEQ ID NO 5
<211> LENGTH: 7
<212> TYPE: PRT
<213> ORGANISM: Mus musculus

<400> SEQUENCE: 5

Ser Thr Ser Ser Leu Ala Ser
1               5

<210> SEQ ID NO 6
<211> LENGTH: 9
<212> TYPE: PRT
<213> ORGANISM: Mus musculus

<400> SEQUENCE: 6

Gln Gln Arg Ser Ser Phe Pro Leu Thr
1               5

<210> SEQ ID NO 7
<211> LENGTH: 107
<212> TYPE: PRT
<213> ORGANISM: Mus musculus

<400> SEQUENCE: 7

Gln Ile Val Leu Thr Gln Ser Pro Ala Ile Met Ser Ala Ser Pro Gly
1               5                   10                  15

Glu Lys Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
        35                  40                  45

Ser Thr Ser Ser Leu Ala Ser Gly Val Pro Ala Arg Phe Gly Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys Arg
            100                 105

<210> SEQ ID NO 8
<211> LENGTH: 107
<212> TYPE: PRT
<213> ORGANISM: Artificial Sequence
<220> FEATURE:
<223> OTHER INFORMATION: humanized murine antibody sequence

<400> SEQUENCE: 8

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30

His Trp Phe Gln Gln Lys Pro Gly Thr Ser Pro Lys Leu Trp Ile Tyr
        35                  40                  45
```

```
Ser Thr Ser Ser Leu Ala Ser Gly Val Pro Ala Arg Phe Gly Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Arg Ser Ser Phe Pro Leu Thr
                85                  90                  95

Phe Gly Ala Gly Thr Lys Leu Glu Leu Lys Arg
            100                 105

<210> SEQ ID NO 9
<211> LENGTH: 117
<212> TYPE: PRT
<213> ORGANISM: Mus musculus

<400> SEQUENCE: 9

Gln Ala Tyr Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Gln Gly Leu Glu Trp Ile
            35                  40                  45

Gly Tyr Ile Tyr Pro Gly Asn Gly Ala Thr Asn Tyr Asn Gln Lys Phe
    50                  55                  60

Lys Gly Lys Ala Thr Leu Thr Ala Asp Pro Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Asp Ser Val Pro Phe Ala Tyr Trp Gly Gln Gly Thr Leu
            100                 105                 110

Val Thr Val Ser Ala
        115

<210> SEQ ID NO 10
<211> LENGTH: 117
<212> TYPE: PRT
<213> ORGANISM: Artificial Sequence
<220> FEATURE:
<223> OTHER INFORMATION: humanized murine antibody sequence

<400> SEQUENCE: 10

Gln Ala Gln Leu Gln Val Ser Gly Ala Glu Val Val Lys Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Gly Gln Gly Leu Glu Trp Ile
            35                  40                  45

Gly Tyr Ile Tyr Pro Gly Asn Gly Ala Thr Asn Tyr Asn Gln Lys Phe
    50                  55                  60

Gln Gly Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Asp Ser Val Pro Phe Ala Tyr Trp Gly Gln Gly Thr Leu
            100                 105                 110

Val Thr Val Ser Ala
        115
```

```
<210> SEQ ID NO 11
<211> LENGTH: 117
<212> TYPE: PRT
<213> ORGANISM: Artificial Sequence
<220> FEATURE:
<223> OTHER INFORMATION: humanized murine antibody sequence

<400> SEQUENCE: 11
```

Gln Ala Gln Leu Gln Val Ser Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Tyr Ile Tyr Pro Gly Asn Gly Ala Thr Asn Tyr Asn Gln Lys Phe
    50                  55                  60

Gln Gly Lys Ala Thr Leu Thr Ala Asp Pro Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg Gly Asp Ser Val Pro Phe Ala Tyr Trp Gly Gln Gly Thr Leu
            100                 105                 110

Val Thr Val Ser Ala
        115

```
<210> SEQ ID NO 12
<211> LENGTH: 15
<212> TYPE: PRT
<213> ORGANISM: Mus musculus

<400> SEQUENCE: 12
```

Gln Val Thr Ala Ile Pro Lys Pro Gly Gly Ala Ser Arg Glu Lys
1               5                   10                  15

```
<210> SEQ ID NO 13
<211> LENGTH: 15
<212> TYPE: PRT
<213> ORGANISM: Homo sapiens

<400> SEQUENCE: 13
```

Glu Val Thr Ala Thr Pro Arg Pro Gly Gly Ala Ser Ser Glu Lys
1               5                   10                  15

```
<210> SEQ ID NO 14
<211> LENGTH: 15
<212> TYPE: PRT
<213> ORGANISM: Homo sapiens

<400> SEQUENCE: 14
```

Glu Val Thr Gly Thr Pro Arg Pro Gly Gly Asp Ser Arg Glu Lys
1               5                   10                  15

```
<210> SEQ ID NO 15
<211> LENGTH: 15
<212> TYPE: PRT
<213> ORGANISM: Homo sapiens

<400> SEQUENCE: 15
```

Glu Val Thr Gly Thr Pro Arg Pro Gly Gly Asp Ser Arg Glu Lys
1               5                   10                  15

-continued

```
<210> SEQ ID NO 16
<211> LENGTH: 23
<212> TYPE: PRT
<213> ORGANISM: Mus musculus

<400> SEQUENCE: 16

Gln Tyr Gln Ala Leu Arg Ser Lys Lys Pro Gly Gln Gln Lys Lys Gly
1               5                   10                  15

Pro Ser Ser Ser Glu Gln Ser
            20

<210> SEQ ID NO 17
<211> LENGTH: 23
<212> TYPE: PRT
<213> ORGANISM: Homo sapiens

<400> SEQUENCE: 17

Gln Gln Val Ala Val Lys Pro Lys Pro Gly Gln Gln Lys Gln Gly
1               5                   10                  15

Thr Ser Ser Ser Glu Gln Ser
            20

<210> SEQ ID NO 18
<211> LENGTH: 22
<212> TYPE: PRT
<213> ORGANISM: Homo sapiens

<400> SEQUENCE: 18

Gln Val Ala Val Lys Pro Lys Pro Gly Gln Gln Lys Gln Gly Glu
1               5                   10                  15

Ser Ser Ser Glu Gln Ser
            20

<210> SEQ ID NO 19
<211> LENGTH: 22
<212> TYPE: PRT
<213> ORGANISM: Homo sapiens

<400> SEQUENCE: 19

Gln Val Ala Val Lys Pro Lys Pro Gly Gln Gln Lys Gln Gly Glu
1               5                   10                  15

Ser Ser Ser Glu Gln Ser
            20

<210> SEQ ID NO 20
<211> LENGTH: 10
<212> TYPE: PRT
<213> ORGANISM: Mus musculus

<400> SEQUENCE: 20

Gly Tyr Thr Phe Thr Ser Tyr Asn Met His
1               5                   10

<210> SEQ ID NO 21
<211> LENGTH: 10
<212> TYPE: PRT
<213> ORGANISM: Mus musculus

<400> SEQUENCE: 21

Tyr Ile Tyr Pro Gly Asn Gly Ala Thr Asn
1               5                   10
```

```
<210> SEQ ID NO 22
<211> LENGTH: 8
<212> TYPE: PRT
<213> ORGANISM: Mus musculus

<400> SEQUENCE: 22

Gly Asp Ser Val Pro Phe Ala Tyr
1               5

<210> SEQ ID NO 23
<211> LENGTH: 95
<212> TYPE: PRT
<213> ORGANISM: Mus musculus

<400> SEQUENCE: 23

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro
                85                  90                  95

<210> SEQ ID NO 24
<211> LENGTH: 98
<212> TYPE: PRT
<213> ORGANISM: Mus musculus

<400> SEQUENCE: 24

Gln Ala Tyr Leu Gln Gln Ser Gly Ala Glu Leu Val Arg Ser Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Tyr Ile Tyr Pro Gly Asn Gly Gly Thr Asn Tyr Asn Gln Lys Phe
    50                  55                  60

Lys Gly Lys Ala Thr Leu Thr Ala Asp Thr Ser Ser Ser Thr Ala Tyr
65                  70                  75                  80

Met Gln Ile Ser Ser Leu Thr Ser Glu Asp Ser Ala Val Tyr Phe Cys
                85                  90                  95

Ala Arg

<210> SEQ ID NO 25
<211> LENGTH: 46
<212> TYPE: DNA
<213> ORGANISM: Artificial Sequence
<220> FEATURE:
<223> OTHER INFORMATION: PCR primer

<400> SEQUENCE: 25
tatagagctc aagcttggat ggtgggaaga tggatacagt tggtgc                46
```

```
<210> SEQ ID NO 26
<211> LENGTH: 36
<212> TYPE: DNA
<213> ORGANISM: Artificial Sequence
<220> FEATURE:
<223> OTHER INFORMATION: PCR primer

<400> SEQUENCE: 26
ggaggatcca tagacagatg ggggtgtcgt tttggc                                 36

<210> SEQ ID NO 27
<211> LENGTH: 32
<212> TYPE: DNA
<213> ORGANISM: Artificial Sequence
<220> FEATURE:
<223> OTHER INFORMATION: PCR primer

<400> SEQUENCE: 27
gggagctcga yattgtgmts acmcarwctm ca                                     32

<210> SEQ ID NO 28
<211> LENGTH: 32
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t

<400> SEQUENCE: 28
cttccggaat tcsargtnma gctgsagsag tc                                     32

<210> SEQ ID NO 29
<211> LENGTH: 35
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t

<400> SEQUENCE: 29
cttccggaat tcsargtnma gctgsagsag tcwgg                                  35

<210> SEQ ID NO 30
<211> LENGTH: 30
<212> TYPE: DNA
<213> ORGANISM: Artificial Sequence
<220> FEATURE:
<223> OTHER INFORMATION: Degenerate primer

<400> SEQUENCE: 30
ttttgaattc aataactaca ggtgtccact                                        30

<210> SEQ ID NO 31
<211> LENGTH: 30
<212> TYPE: DNA
<213> ORGANISM: Artificial Sequence
<220> FEATURE:
<223> OTHER INFORMATION: Degenerate primer

<400> SEQUENCE: 31
ttttgagctc cagattttca gcttcctgct                                        30
```

<210> SEQ ID NO 32
<211> LENGTH: 40
<212> TYPE: DNA
<213> ORGANISM: Artificial Sequence
<220> FEATURE:
<223> OTHER INFORMATION: PCR primer

<400> SEQUENCE: 32
cgatgggccc ttggtggagg ctgcagagac agtgaccaga                           40

<210> SEQ ID NO 33
<211> LENGTH: 28
<212> TYPE: DNA
<213> ORGANISM: Artificial Sequence
<220> FEATURE:
<223> OTHER INFORMATION: PCR primer

<400> SEQUENCE: 33
ttttcgtacg tttcagctcc agcttggt                                        28

<210> SEQ ID NO 34
<211> LENGTH: 35
<212> TYPE: DNA
<213> ORGANISM: Artificial Sequence
<220> FEATURE:
<223> OTHER INFORMATION: PCR primer

<400> SEQUENCE: 34
caggtgtaca ctcccaggct tatctccagc agtct                                35

<210> SEQ ID NO 35
<211> LENGTH: 40
<212> TYPE: DNA
<213> ORGANISM: Artificial Sequence
<220> FEATURE:
<223> OTHER INFORMATION: PCR primer

<400> SEQUENCE: 35
cgatgggccc ttggtggagg cggcagagac agtgaccaga                           40

<210> SEQ ID NO 36
<211> LENGTH: 56
<212> TYPE: DNA
<213> ORGANISM: Artificial Sequence
<220> FEATURE:
<223> OTHER INFORMATION: PCR primer

<400> SEQUENCE: 36
caggtgtaca ctccgagatt gttctcaccc agtctccagc aaccatgtct gcatct         56

<210> SEQ ID NO 37
<211> LENGTH: 36
<212> TYPE: DNA
<213> ORGANISM: Artificial Sequence
<220> FEATURE:
<223> OTHER INFORMATION: PCR primer

<400> SEQUENCE: 37
ggcactgcag gttatggtga ccctctcccc tggaga                               36

<210> SEQ ID NO 38
<211> LENGTH: 25
<212> TYPE: DNA
<213> ORGANISM: Artificial Sequence
<220> FEATURE:
<223> OTHER INFORMATION: PCR primer

```
<400> SEQUENCE: 38
caatcagcag catggaggct gaaga                                          25

<210> SEQ ID NO 39
<211> LENGTH: 24
<212> TYPE: DNA
<213> ORGANISM: Artificial Sequence
<220> FEATURE:
<223> OTHER INFORMATION: PCR primer

<400> SEQUENCE: 39
gcctccatgc tgctgattgt gaga                                           24

<210> SEQ ID NO 40
<211> LENGTH: 67
<212> TYPE: DNA
<213> ORGANISM: Artificial Sequence
<220> FEATURE:
<223> OTHER INFORMATION: PCR primer

<400> SEQUENCE: 40
caggtgtaca ctcccaggct cagctccagg tgtctggggc tgaggtggtg aagcccgggg    60
cctcagt                                                              67

<210> SEQ ID NO 41
<211> LENGTH: 27
<212> TYPE: DNA
<213> ORGANISM: Artificial Sequence
<220> FEATURE:
<223> OTHER INFORMATION: PCR primer

<400> SEQUENCE: 41
ttgactgcag acacatcctc cagcaca                                        27

<210> SEQ ID NO 42
<211> LENGTH: 40
<212> TYPE: DNA
<213> ORGANISM: Artificial Sequence
<220> FEATURE:
<223> OTHER INFORMATION: PCR primer

<400> SEQUENCE: 42
gtgtctgcag tcaatgtggc cttgccctgg aacttctgat                          40

<210> SEQ ID NO 43
<211> LENGTH: 40
<212> TYPE: DNA
<213> ORGANISM: Artificial Sequence
<220> FEATURE:
<223> OTHER INFORMATION: PCR primer

<400> SEQUENCE: 43
cgatgggccc ttggtggagg cggcagagac agtgacaaga                          40

<210> SEQ ID NO 44
<211> LENGTH: 107
<212> TYPE: PRT
<213> ORGANISM: Mus musculus

<400> SEQUENCE: 44

Gln Ile Val Leu Thr Gln Ser Pro Ala Ile Met Ser Ala Phe Pro Gly
1               5                   10                  15

Glu Lys Val Thr Ile Thr Cys Ser Ala Thr Ser Ser Val Asn Tyr Met
            20                  25                  30
```

His Trp Phe Gln Gln Lys Pro Gly Thr Ser Pro Lys Leu Trp Ile Tyr
            35                  40                  45

Ser Ser Ser Asn Leu Ala Ser Gly Val Pro Ala Arg Phe Ser Gly Ser
 50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Ile Thr
                85                  90                  95

Phe Gly Ser Gly Thr Lys Leu Glu Ile Lys Arg
                100                 105

<210> SEQ ID NO 45
<211> LENGTH: 107
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 45

Xaa Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Asn Ile
                20                  25                  30

His Trp Phe Gln Gln Lys Pro Gly Thr Phe Pro Lys Leu Trp Ile Tyr
            35                  40                  45

Ser Thr Ser Thr Leu Ala Ser Gly Val Pro Gly Arg Phe Ser Gly Ser
 50                  55                  60

Gly Ser Gly Thr Ser Tyr Ser Leu Thr Ile Ser Arg Met Gly Ala Glu
65                  70                  75                  80

Asp Ala Ala Thr Tyr Tyr Cys Gln Gln Arg Ser Gly Tyr Pro Phe Thr
                85                  90                  95

Phe Gly Ser Gly Thr Lys Leu Glu Ile Lys Arg
                100                 105

<210> SEQ ID NO 46
<211> LENGTH: 107
<212> TYPE: PRT
<213> ORGANISM: Mus musculus

<400> SEQUENCE: 46

Asp Ile Gln Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Gly Ser Ser Pro Arg Leu Leu Ile Tyr
            35                  40                  45

Asp Ser Thr Asn Leu Ala Ser Gly Val Pro Val Arg Phe Ser Gly Ser
 50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Thr Tyr Pro Leu Thr
                85                  90                  95

Phe Gly Ala Gly Thr Lys Leu Glu Leu Lys Arg
                100                 105

<210> SEQ ID NO 47
<211> LENGTH: 108
<212> TYPE: PRT
<213> ORGANISM: Mus musculus

<400> SEQUENCE: 47

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Tyr Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Ile
                85                  90                  95

Thr Phe Gly Val Gly Thr Lys Leu Glu Leu Lys Arg
            100                 105

<210> SEQ ID NO 48
<211> LENGTH: 105
<212> TYPE: PRT
<213> ORGANISM: Mus musculus

<400> SEQUENCE: 48

Gln Ile Val Ser Thr Gln Ser Pro Ala Ile Met Ser Ala Ser Pro Gly
1               5                   10                  15

Glu Lys Val Thr Met Thr Cys Ser Ala Ser Ser Ser Arg Ser Tyr Met
            20                  25                  30

Gln Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Ser Ser Tyr Thr Phe Gly
                85                  90                  95

Gly Gly Thr Lys Leu Glu Ile Lys Arg
            100                 105

<210> SEQ ID NO 49
<211> LENGTH: 107
<212> TYPE: PRT
<213> ORGANISM: Mus musculus

<400> SEQUENCE: 49

Gln Thr Val Leu Ser Gln Ser Pro Ala Ile Leu Ser Ala Ser Pro Gly
1               5                   10                  15

Glu Lys Val Thr Met Thr Cys Arg Ala Ser Ser Ser Val Thr Tyr Ile
            20                  25                  30

His Trp Tyr Gln Gln Lys Pro Gly Ser Ser Pro Lys Ser Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln His Trp Ser Ser Lys Pro Pro Thr
                85                  90                  95

Phe Gly Gly Gly Thr Lys Leu Glu Ile Lys Arg
            100                 105

<210> SEQ ID NO 50
<211> LENGTH: 107
<212> TYPE: PRT
<213> ORGANISM: Mus musculus

<400> SEQUENCE: 50

Gln Ser Val Leu Ser Gln Ser Pro Ala Ile Leu Ser Ala Ser Pro Gly
1               5                   10                  15

Glu Lys Val Ile Met Thr Cys Ser Pro Ser Ser Val Ser Tyr Met
            20                  25                  30

Gln Trp Tyr Gln Gln Lys Pro Gly Ser Ser Pro Lys Pro Trp Ile Tyr
        35                  40                  45

Ser Thr Ser Asn Leu Ala Ser Gly Val Pro Gly Arg Phe Ser Gly Gly
    50                  55                  60

Gly Ser Gly Thr Ser Phe Ser Leu Thr Ile Ser Gly Val Glu Ala Glu
65                  70                  75                  80

Asp Ala Ala Thr Tyr Tyr Cys Gln Gln Tyr Ser Ser His Pro Leu Thr
                85                  90                  95

Phe Gly Gly Gly Thr Lys Leu Glu Leu Lys Arg
            100                 105

<210> SEQ ID NO 51
<211> LENGTH: 109
<212> TYPE: PRT
<213> ORGANISM: Mus musculus

<400> SEQUENCE: 51

Glu Asn Val Leu Thr Gln Ser Pro Ala Ile Met Ser Ala Ser Pro Gly
1               5                   10                  15

Glu Lys Val Thr Met Ala Cys Arg Ala Ser Ser Ser Val Ser Ser Thr
            20                  25                  30

Tyr Leu His Trp Tyr Gln Gln Lys Ser Gly Ala Ser Pro Lys Leu Leu
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Val Glu
65                  70                  75                  80

Ala Glu Asp Ala Ala Thr Tyr Tyr Cys Gln Gln Tyr Ser Gly Tyr Pro
                85                  90                  95

Leu Thr Phe Gly Ala Gly Thr Lys Leu Glu Leu Lys Arg
            100                 105

<210> SEQ ID NO 52
<211> LENGTH: 110
<212> TYPE: PRT
<213> ORGANISM: Mus musculus

<400> SEQUENCE: 52

Asp Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

```
Asn Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys His Gln Tyr His Arg Ser Pro
                 85                  90                  95

Tyr Thr Phe Gly Gly Gly Thr Lys Leu Glu Ile Lys Arg Ala
                100                 105                 110

<210> SEQ ID NO 53
<211> LENGTH: 109
<212> TYPE: PRT
<213> ORGANISM: Mus musculus

<400> SEQUENCE: 53

Asp Ile Gln Leu Thr Gln Ser Pro Ala Phe Met Ala Ala Ser Pro Gly
 1               5                  10                  15

Glu Lys Val Thr Ile Thr Cys Ser Val Ser Ser Ile Ser Ser Ser
                 20                  25                  30

Asn Leu His Trp Tyr Gln Gln Lys Ser Glu Thr Ser Pro Lys Pro Trp
            35                  40                  45

Ile Tyr Gly Thr Ser Asn Leu Ala Ser Gly Val Pro Val Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Asn Ser Tyr Pro
                 85                  90                  95

Tyr Thr Phe Gly Gly Gly Thr Lys Leu Glu Ile Lys Arg
                100                 105

<210> SEQ ID NO 54
<211> LENGTH: 117
<212> TYPE: PRT
<213> ORGANISM: Mus musculus

<400> SEQUENCE: 54

Gln Ile Gln Leu Gln Gln Ser Gly Pro Glu Leu Val Arg Pro Gly Ala
 1               5                  10                  15

Ser Val Lys Ile Ser Cys Lys Ala Ser Gly Tyr Thr Phe Thr Asp Tyr
                 20                  25                  30

Tyr Ile His Trp Val Lys Gln Arg Pro Gly Glu Gly Leu Glu Trp Ile
            35                  40                  45

Gly Trp Ile Tyr Pro Gly Ser Gly Asn Thr Lys Tyr Asn Glu Lys Phe
 50                  55                  60

Lys Gly Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Gly Gly Lys Phe Ala Met Asp Tyr Trp Gly Gln Gly Thr Ser
                100                 105                 110

Val Thr Val Ser Ser
            115
```

<210> SEQ ID NO 55
<211> LENGTH: 122
<212> TYPE: PRT
<213> ORGANISM: Mus musculus

<400> SEQUENCE: 55

Gln Val Gln Leu Gln Gln Pro Gly Ala Glu Leu Val Lys Pro Gly Ala
1               5                   10                  15

Ser Val Arg Met Ser Cys Lys Ala Ser Gly Tyr Thr Phe Thr Asn Tyr
            20                  25                  30

Asn Met Tyr Trp Val Lys Gln Ser Pro Gly Gln Gly Leu Glu Trp Ile
        35                  40                  45

Gly Ile Phe Tyr Pro Gly Asn Gly Asp Thr Ser Tyr Asn Gln Lys Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Gly Gly Ser Tyr Arg Tyr Asp Gly Gly Phe Asp Tyr Trp
            100                 105                 110

Gly Gln Gly Thr Thr Leu Thr Val Ser Ser
        115                 120

<210> SEQ ID NO 56
<211> LENGTH: 119
<212> TYPE: PRT
<213> ORGANISM: Mus musculus

<400> SEQUENCE: 56

Gln Gly Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Phe
            20                  25                  30

Trp Val Asn Trp Val Lys Gln Arg Pro Gly Gln Gly Leu Glu Trp Ile
        35                  40                  45

Gly Gln Ile Tyr Pro Gly Asp Gly Asp Asn Lys Tyr Asn Gly Lys Phe
    50                  55                  60

Lys Gly Lys Ala Thr Leu Thr Ala Asp Lys Ser Ser Thr Thr Ala Tyr
65                  70                  75                  80

Met Gln Leu Tyr Ser Leu Thr Ser Glu Asp Ser Ala Val Tyr Phe Cys
                85                  90                  95

Ala Arg Ser Gly Asn Tyr Pro Tyr Ala Met Asp Tyr Trp Gly Gln Gly
            100                 105                 110

Thr Ser Val Thr Val Ser Ser
        115

<210> SEQ ID NO 57
<211> LENGTH: 120
<212> TYPE: PRT
<213> ORGANISM: Mus musculus

<400> SEQUENCE: 57

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

```
Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Tyr Gly Ser Ser Tyr Phe Asp Tyr Trp Gly Gln
                100                 105                 110

Gly Thr Thr Val Thr Val Ser Ser
            115                 120

<210> SEQ ID NO 58
<211> LENGTH: 121
<212> TYPE: PRT
<213> ORGANISM: Mus musculus

<400> SEQUENCE: 58

Glu Val Gln Leu Gln Gln Ser Gly Val Glu Leu Val Arg Ala Gly Ser
1               5                   10                  15

Ser Val Lys Met Ser Cys Lys Ala Ser Gly Tyr Thr Phe Thr Ser Asn
                20                  25                  30

Gly Ile Asn Trp Val Lys Gln Arg Pro Gly Gln Gly Leu Glu Trp Ile
            35                  40                  45

Gly Tyr Asn Asn Pro Gly Asn Gly Tyr Ile Ala Tyr Asn Glu Lys Phe
    50                  55                  60

Lys Gly Lys Thr Thr Leu Thr Val Asp Lys Ser Ser Ser Thr Ala Tyr
65                  70                  75                  80

Met Gln Leu Arg Ser Leu Thr Ser Glu Asp Ser Ala Val Tyr Phe Cys
                85                  90                  95

Ala Arg Ser Glu Tyr Tyr Gly Gly Ser Tyr Lys Phe Asp Tyr Trp Gly
                100                 105                 110

Gln Gly Thr Thr Leu Thr Val Ser Ser
            115                 120

<210> SEQ ID NO 59
<211> LENGTH: 120
<212> TYPE: PRT
<213> ORGANISM: Mus musculus

<400> SEQUENCE: 59

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Met Lys Gln Lys Pro Gly Gln Gly Leu Glu Trp Ile
            35                  40                  45

Gly Trp Ile Asp Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Arg Glu Lys Thr Thr Tyr Tyr Tyr Ala Met Asp Tyr Trp Gly Gln
                100                 105                 110

Gly Thr Ser Val Thr Val Ser Ala
            115                 120
```

<210> SEQ ID NO 60
<211> LENGTH: 120
<212> TYPE: PRT
<213> ORGANISM: Mus musculus

<400> SEQUENCE: 60

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Phe
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Gly Thr His Tyr Asn Glu Lys Phe
    50                  55                  60

Lys Gly Lys Ala Thr Phe Thr Ala Asp Lys Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly His Ser Tyr Tyr Phe Tyr Asp Gly Asp Tyr Trp Gly Gln
            100                 105                 110

Gly Thr Ser Val Thr Val Ser Ser
        115                 120

<210> SEQ ID NO 61
<211> LENGTH: 124
<212> TYPE: PRT
<213> ORGANISM: Mus musculus

<400> SEQUENCE: 61

Gln Val Gln Leu Gln Gln Ser Gly Ala Glu Leu Val Arg Ala Gly Ser
1               5                   10                  15

Ser Val Lys Met Ser Cys Lys Ala Ser Gly Tyr Thr Phe Thr Ser Tyr
            20                  25                  30

Gly Val Asn Trp Val Lys Gln Arg Pro Gly Gln Gly Leu Glu Trp Ile
        35                  40                  45

Gly Tyr Ile Asn Pro Gly Lys Gly Tyr Leu Ser Tyr Asn Glu Lys Phe
    50                  55                  60

Lys Gly Lys Thr Thr Leu Thr Val Asp Arg Ser Ser Ser Thr Ala Tyr
65                  70                  75                  80

Met Gln Leu Arg Ser Leu Thr Ser Glu Asp Ala Ala Val Tyr Phe Cys
                85                  90                  95

Ala Arg Ser Phe Tyr Gly Gly Ser Asp Leu Ala Val Tyr Tyr Phe Asp
            100                 105                 110

Ser Trp Gly Gln Gly Thr Thr Leu Thr Val Ser Ser
        115                 120

<210> SEQ ID NO 62
<211> LENGTH: 116
<212> TYPE: PRT
<213> ORGANISM: Mus musculus

<400> SEQUENCE: 62

Gln Val Gln Leu Gln Glu Ser Gly Ala Glu Val Met Lys Pro Gly Ala
1               5                   10                  15

Ser Val Lys Ile Ser Cys Lys Ala Thr Gly Tyr Thr Phe Ser Thr Tyr
            20                  25                  30

Trp Ile Glu Trp Val Lys Gln Arg Pro Gly His Gly Leu Glu Trp Ile
        35                  40                  45

```
                                  -continued

Gly Glu Ile Leu Pro Gly Ser Gly Ser Thr Tyr Tyr Asn Glu Lys Phe
        50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                85                  90                  95

Ala Arg Gly Asp Gly Asn Tyr Gly Tyr Trp Gly Gln Gly Thr Thr Leu
            100                 105                 110

Thr Val Ser Ser
        115

<210> SEQ ID NO 63
<211> LENGTH: 116
<212> TYPE: PRT
<213> ORGANISM: Mus musculus

<400> SEQUENCE: 63

Gln Val Gln Leu Gln Gln Ser Gly Ala Glu Leu Val Arg Pro Gly Ala
 1               5                  10                  15

Ser Val Lys Leu Ser Cys Lys Ala Ser Gly Tyr Thr Phe Ile Ser Tyr
                20                  25                  30

Trp Ile Asn Trp Val Lys Gln Arg Pro Gly Gln Gly Leu Glu Trp Ile
            35                  40                  45

Gly Asn Ile Tyr Pro Ser Asp Ser Tyr Thr Asn Tyr Asn Gln Lys Phe
        50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                85                  90                  95

Thr Arg Asp Asp Asn Tyr Gly Ala Met Asp Tyr Trp Gly Gln Gly Thr
            100                 105                 110

Thr Val Thr Val
        115
```

CA6 ANTIGEN-SPECIFIC CYTOTOXIC CONJUGATE AND METHODS OF USING THE SAME

RELATED APPLICATIONS

The present application is a continuation-in-part application of application Ser. No. 10/895,135, filed Jul. 21, 2004, now abandoned, which claims benefit of U.S. Provisional Application No. 60/488,447, filed Jul. 21, 2003. Both applications are herein incorporated by reference in their entireties.

FIELD OF THE INVENTION

The present invention is directed to a murine anti-CA6 glycotope monoclonal antibody, and humanized or resurfaced versions thereof. The present invention is also directed to epitope-binding fragments of the anti-CA6 glycotope monoclonal antibody, as well as to epitope-binding fragments of humanized or resurfaced versions of the anti-CA6 glycotope monoclonal antibody.

The present invention is further directed to cytotoxic conjugates comprising a cell binding agent and a cytotoxic agent, therapeutic compositions comprising the conjugate, methods for using the conjugates in the inhibition of cell growth and the treatment of disease, and a kit comprising the cytotoxic conjugate. In particular, the cell binding agent is a monoclonal antibody, or epitope-binding fragment thereof, that recognizes and binds the CA6 glycotope or a humanized or resurfaced version thereof.

BACKGROUND OF THE INVENTION

There have been numerous attempts to develop anti-cancer therapeutic agents that specifically destroy target cancer cells without harming surrounding, non-cancerous cells and tissue. Such therapeutic agents have the potential to vastly improve the treatment of cancer in human patients.

One promising approach has been to link cell binding agents, such as monoclonal antibodies, with cytotoxic drugs (Sela et al, in Immunoconjugates 189-216 (C. Vogel, ed. 1987); Ghose et al, in Targeted Drugs 1-22 (E. Goldberg, ed. 1983); Diener et al, in Antibody mediated delivery systems 1-23 (J. Rodwell, ed. 1988); Pietersz et al, in Antibody mediated delivery systems 25-53 (J. Rodwell, ed. 1988); Bumol et al, in Antibody mediated delivery systems 55-79 (J. Rodwell, ed. 1988). Depending on the selection of the cell binding agent, these cytotoxic conjugates can be designed to recognize and bind only specific types of cancerous cells, based on the expression profile of molecules expressed on the surface of such cells.

Cytotoxic drugs such as methotrexate, daunorubicin, doxorubicin, vincristine, vinblastine, melphalan, mitomycin C, and chlorambucil have been used in such cytotoxic conjugates, linked to a variety of murine monoclonal antibodies. In some cases, the drug molecules were linked to the antibody molecules through an intermediary carrier molecule such as serum albumin (Garnett et al, 46 Cancer Res. 2407-2412 (1986); Ohkawa et al 23 Cancer Immunol. Immunother. 81-86 (1986); Endo et al, 47 Cancer Res. 1076-1080 (1980)), dextran (Hurwitz et al, 2 Appl. Biochem. 25-35 (1980); Manabi et al, 34 Biochem. Pharmacol. 289-291 (1985); Dillman et al, 46 Cancer Res. 4886-4891 (1986); Shoval et al, 85 Proc. Natl. Acad. Sci. 8276-8280 (1988)), or polyglutamic acid (Tsukada et al, 73 J. Natl. Canc. Inst. 721-729 (1984); Kato et al 27 J. Med. Chem. 1602-1607 (1984); Tsukada et al, 52 Br. J. Cancer 111-116 (1985)).

As an example of one specific conjugate that has shown some promise, is the conjugate of the C242 antibody, directed against CanAg, an antigen expressed on colorectal and pancreatic tumors, and the maytansine derivative DM1 (Liu et al., *Proc Natl Acad Sci USA*, 93: 8618-8623 (1996)). In vitro evaluation of this conjugate indicated that its binding affinity towards CanAg expressed on the cell surface was high with an apparent $K_d$ value of $3 \times 10^{-11}$ M, and its cytotoxic potency for CanAg-positive cells was high with an $IC_{50}$ of $6 \times 10^{-11}$ M. This cytotoxicity was antigen-dependent since it was blocked by an excess of non-conjugated antibody, and since antigen-negative cells were more than 100-fold less sensitive to the conjugate. Other examples of antibody-DM1 conjugates with both high affinity towards respective target cells and high antigen-selective cytotoxicity include those of huN901, a humanized version of antibody against human CD56; huMy9-6, a humanized version of antibody against human CD33; huC242, a humanized version of antibody against the CanAg Muc1 epitope; huJ591, a deimmunized antibody against PSMA; trastuzumab, a humanized antibody against Her2/neu; and bivatuzumab, a humanized antibody against CD44v6.

The development of additional cytotoxic conjugates that specifically recognize particular types of cancerous cells will be important in the continuing improvement of methods used to treat patients with cancer.

To that end, the present invention is directed to the development of antibodies that recognize and bind molecules/receptors expressed on the surface of cancerous cells, and to the development of novel cytotoxic conjugates comprising cell binding agents, such as antibodies, and cytotoxic agents that specifically target the molecules/receptors expressed on the surface of cancerous cells.

More specifically, the present invention is directed to the characterization of a novel CA6 sialoglycotope on the Muc1 mucin receptor expressed by cancerous cells, and to the provision of antibodies, preferably humanized antibodies, that recognize the novel CA6 sialoglycotope of the Muc1 mucin and that may be used to inhibit the growth of a cell expressing the CA6 glycotope in the context of a cytotoxic agent.

SUMMARY OF THE INVENTION

The present invention includes antibodies that specifically recognize and bind a novel CA6 sialoglycotope of the Muc1 mucin receptor, or an epitope-binding fragment thereof. In another embodiment, the present invention includes a humanized antibody, or an epitope-binding fragment thereof, that recognizes the novel CA6 sialoglycotope ("the CA6 glycotope") of the Muc1 mucin receptor.

In preferred embodiments, the present invention includes the murine anti-CA6 monoclonal antibody DS6 ("the DS6 antibody"), and resurfaced or humanized versions of the DS6 antibody wherein surface-exposed residues of the antibody, or its epitope-binding fragments, are replaced in both light and heavy chains to more closely resemble known human antibody surfaces. The humanized antibodies and epitope-binding fragments thereof of the present invention have improved properties in that they are much less immunogenic (or completely non-immunogenic) in human subjects to which they are administered than fully murine versions. Thus, the humanized DS6 antibodies and epitope-binding fragments thereof of the present invention specifically recognize a novel sialoglycotope on the Muc1 mucin receptor, i.e., the CA6 glycotope, while not being immunogenic to a human.

The humanized antibodies and epitope-binding fragments thereof can be conjugated to a drug, such as a maytansinoid, to form a prodrug having specific cytotoxicity towards antigen-expressing cells by targeting the drug to the Muc1 CA6 sialoglycotope. Cytotoxic conjugates comprising such antibodies and small, highly toxic drugs (e.g., maytansinoids, taxanes, and CC-1065 analogs) can thus be used as a therapeutic for treatment of tumors, such as breast and ovarian tumors.

The humanized versions of the DS6 antibody of the present invention are fully characterized herein with respect to their respective amino acid sequences of both light and heavy chain variable regions, the DNA sequences of the genes for the light and heavy chain variable regions, the identification of the CDRs, the identification of their surface amino acids, and disclosure of a means for their expression in recombinant form.

In one embodiment, there is provided a humanized DS6 antibody or an epitope-binding fragment thereof having a heavy chain including CDRs having amino acid sequences represented by SEQ ID NOS:1-3:

(SEQ ID NO: 1)
S Y N M H, (SEQ ID NO: 2)
Y I Y P G N G A T N Y N Q K F K G, (SEQ ID NO: 3)
G D S V P F A Y, and having a light chain that comprises CDRs having amino acid sequences represented by SEQ ID NOS:4-6:

(SEQ ID NO: 4)
S A H S S V S F M H, (SEQ ID NO: 5)
S T S S L A S, (SEQ ID NO: 6)
Q Q R S S F P L T,

Also provided are humanized DS6 antibodies and epitope-binding fragments thereof having a light chain variable region that has an amino acid sequence that shares at least 90% sequence identity with an amino acid sequence represented by SEQ ID NO:7 or SEQ ID NO: 8:

(SEQ ID NO: 7)
QIVLTQSPAIMSASPGEKVTITCSAHSSVSFMHWFQQKPGTSPKLWIYST

SSLASGVPARFGGSGSGTSYSLTISRMEAEDAATYYCQQRSSFPLTFGAG

TKLELKR (SEQ ID NO: 8)
EIVLTQSPATMSASPGERVTITCSAHSSVSFMHWFQQKPGTSPKLWIYST

SSLASGVPARFGGSGSGTSYSLTISSMEAEDAATYYCQQRSSFPLTFGAG

TKLELKR

Similarly, there are provided humanized DS6 antibodies and epitope-binding fragments thereof having a heavy chain variable region that has an amino acid sequence that shares at least 90% sequence identity with an amino acid sequence represented by SEQ ID NO:9, SEQ ID NO:10, or SEQ ID NO: 11:

(SEQ ID NO: 9)
QAYLQQSGAELVRSGASVKMSCKASGYTFTSYNMHWVKQTPGQGLEWIGY

IYPGNGATNYNQKEKGKATLTADPSSSTAYMQISSLTSEDSAVYFCARGD

SVPFAYWGQGTLVTVSA (SEQ ID NO: 10)
QAQLVQSGAEVVKPGASVKMSCKASGYTFTSYNMHWVKQTPGQGLEWIGY

IYGNGATNYNQKFQGKATLTADTSSSTAYMQISSLTSEDSAVYFCARGDS

VPFAYWGQGTLVTVSA (SEQ ID NO: 11)
QAQLVQSGAEVVKPGASVKMSCKASGYTFTSYNMHWVKQTPGQGLEWIGY

IYPGNGATNYNQKFQGKATLTADPSSSTAYMQISSLTSEDSAVYFCARGD

SVPFAYWGQGTLVTVSA

In another embodiment, humanized DS6 antibodies and epitope-binding fragments thereof are provided having a humanized or resurfaced light chain variable region having an amino acid sequence corresponding to SEQ ID NO: 8

(SEQ ID NO: 8)
EIVLTQSPATMSASPGERVTITCSAHSSVSFMHWFQQKPGTSPKLWIYST

SSLASGVPARFGGSGSGTSYSLTISSMEAEDAATYYCQQRSSFPLTFGAG

TKLELKR.

Similarly, humanized DS6 antibodies and epitope-binding fragments thereof are provided having a humanized or resurfaced heavy chain variable region having an amino acid sequence corresponding to SEQ ID NO:10 or SEQ ID NO: 11, respectively:

(SEQ ID NO: 10)
QAQLVQSGAEVVKPGASVKMSCKASGYTFTSYNMHWVKQTPGQGLEWIGY

IYPGNGATNYNQKFQGKATLTADTSSSTAYMQISSLTSEDSAVYFCARGD

SVPFAYWGQGTLVTVSA.

(SEQ ID NO: 11)
QAQLVQSGAEVVKPGASVKMSCKASGYTFTSYNMHWVKQTPGQGLEWIGY

IYPGNGATNYNQKFQGKATLTADPSSSTAYMQISSLTSEDSAVYFCARGD

SVPFAYWGQGTLVTVSA.

The humanized DS6 antibodies and epitope-binding fragments thereof of the present invention can also include substitution in light and/or heavy chain amino acid residues at one or more positions defined by the starred residues in Table 1 which represent the murine surface framework residues found within 5 Angstroms of a CDR requiring change to a human residue. For example, the first amino acid residue Q in the murine sequence (SEQ ID NO:7) has been replaced by E (SEQ ID NO:8) to humanize the antibody. However, because of the proximity of this residue to a CDR, a back mutation to the murine residue Q may be required to maintain antibody affinity.

TABLE 1 muDS6 framework residues proximal
to a CDR (Kabat numbering)

| Light chain | Heavy chain |
| --- | --- |
| Q1* | Q1 |
| V3 | K64* |
| T5 | P73* |
| P40 | S74 |
| G57 | |
| A60 | |
| S67 | |
| E81 | |

This is further shown in Table 2 where muDS6 variable region surface residues are shown aligned with the three most homologous human variable region surface residues. The amino acid residues in Table 1 correspond to the underlined amino acid residues in Table 2.

TABLE 2

Top 3 Most Homologous Human Antibody Surfaces

| Antibody | Light Chain | SEQ ID NO: |
| --- | --- | --- |
| muDS6 | Q V T A I P K P G G A S R E K | SEQ ID NO: 12 |
| 28E4 | E V T A T P R P G G A S S E K | SEQ ID NO: 13 |
| HAZcPB | E V T G T P R P G G D S R E K | SEQ ID NO: 14 |
| SSaPB | E V T G T P R P G G D S R E K | SEQ ID NO: 15 |

| Antibody | Heavy Chain | SEQ ID NO: |
| --- | --- | --- |
| muDS6 | Q Y Q A L R S K K P G Q Q K K G P S S S E Q S | SEQ ID NO: 16 |
| 28E4 | Q Q V A V K P K K P G Q Q K Q G T S S S E Q S | SEQ ID NO: 17 |
| HAZcPB | – Q V A V K P K K P G Q Q K Q G E S S S E Q S | SEQ ID NO: 18 |
| SSaPB | – Q V A V K P K K P G Q Q K Q G E S S S E Q S | SEQ ID NO: 19 |

The present invention further provides cytotoxic conjugates comprising (1) a cell binding agent that recognizes and binds the CA6 glycotope, and (2) a cytotoxic agent. In the cytotoxic conjugates, the cell binding agent has a high affinity for the CA6 glycotope and the cytotoxic agent has a high degree of cytotoxicity for cells expressing the CA6 glycotope, such that the cytotoxic conjugates of the present invention form effective killing agents.

In a preferred embodiment, the cell binding agent is an anti-CA6 antibody or an epitope-binding fragment thereof, more preferably a humanized anti-CA6 antibody or an epitope-binding fragment thereof, wherein a cytotoxic agent is covalently attached, directly or via a cleavable or non-cleavable linker, to the antibody or epitope-binding fragment thereof. In more preferred embodiments, the cell binding agent is the humanized DS6 antibody or an epitope-binding fragment thereof, and the cytotoxic agent is a taxol, a maytansinoid, CC-1065 or a CC-1065 analog.

In preferred embodiments of the invention, the cell binding agent is a humanized anti-CA6 antibody and the cytotoxic agent is a cytotoxic drug such as a maytansinoid or a taxane.

More preferably, the cell binding agent is the humanized anti-CA6 antibody DS6 and the cytotoxic agent is a maytansine compound, such as DM1 or DM4.

The present invention also includes a method for inhibiting the growth of a cell expressing the CA6 glycotope. In preferred embodiments, the method for inhibiting growth of the cell expressing the CA6 glycotope takes place in vivo and results in the death of the cell, although in vitro and ex vivo applications are also included.

The present invention also provides a therapeutic composition comprising the cytotoxic conjugate, and a pharmaceutically acceptable carrier or excipient.

The present invention further includes a method of treating a subject having cancer using the therapeutic composition. In preferred embodiments, the cytotoxic conjugate comprises an anti-CA6 antibody and a cytotoxic agent. In more preferred embodiments, the cytotoxic conjugate comprises a humanized DS6 antibody-DM1 conjugate, humanized DS6 antibody-DM4 or a humanized DS6 antibody-taxane conjugate, and the conjugate is administered along with a pharmaceutically acceptable carrier or excipient.

The present invention also includes a kit comprising an anti-CA6 antibody-cytotoxic agent conjugate and instructions for use. In preferred embodiments, the anti-CA6 antibody is the humanized DS6 antibody, the cytotoxic agent is a maytansine compound, such as DM1 or DM4, or a taxane, and the instructions are for using the conjugates in the treatment of a subject having cancer. The kit may also include components necessary for the preparation of a pharmaceutically acceptable formulation, such a diluent if the conjugate is in a lyophilized state or concentrated form, and for the administration of the formulation.

The present invention also includes derivatives of antibodies that specifically bind and recognize the CA6 glycotope. In preferred embodiments, the antibody derivatives are prepared by resurfacing or humanizing antibodies that bind the CA6 glycotope, wherein the derivatives have decreased immunogenicity toward the host.

The present invention further provides for humanized antibodies or fragments thereof that are further labeled for use in research or diagnostic applications. In preferred embodiments, the label is a radiolabel, a fluorophore, a chromophore, an imaging agent or a metal ion.

A method for diagnosis is also provided in which said labeled humanized antibodies or epitope-binding fragments thereof are administered to a subject suspected of having a cancer, and the distribution of the label within the body of the subject is measured or monitored.

The present invention also provides methods for the treatment of a subject having a cancer by administering a humanized antibody conjugate of the present invention, either alone or in combination with other cytotoxic or therapeutic agents. The cancer can be one or more of, for example, breast cancer, colon cancer, ovarian carcinoma, endometrial cancer, osteosarcoma, cervical cancer, prostate cancer, lung cancer, synovial carcinoma, pancreatic cancer, a sarcoma or a carcinoma in which CA6 is expressed or other cancer yet to be determined in which CA6 glycotope is expressed predominantly.

Unless otherwise stated, all references and patents cited herein are incorporated by reference.

BRIEF DESCRIPTION OF THE DRAWINGS

FIG. 2 shows the results of dot blot analysis of epitope expression. Caov-3 (FIG. 2A & FIG. 2B), SKMEL28 (FIG. 2C), and Colo205 (FIG. 2D) cell lysates were individually spotted onto nitrocellulose membranes and then incubated individually with pronase, proteinase K, neuraminidase or periodic acid. The membranes were then immunoblotted with the DS6 antibody (FIG. 2A), the CM1 antibody (FIG. 2B), the R24 antibody (FIG. 2C), or the C242 antibody (FIG. 2D).

FIG. 5 shows the results of western blot analysis of the DS6 antigen. Cell lysates were immunoprecipitated ("IP") and immunoblotted with the DS6 antibody. The antigen corresponds to a >250 kDa protein band observed in antigen-positive Caov-3 (FIG. 5A and FIG. 5B) and T47D (FIG. 5C) cells. Antigen negative SK-OV-3 (FIG. 5D) and Colo205 (FIG. 5E) cell lines do not exhibit this band. After immunoprecipitation, the Protein G beads of the Caov-3 cell lysates were incubated with (FIG. 5A) neuraminidase ("N") or (FIG. 5B) periodic acid ("PA"). Antibody ("α"), pre-IP ("Lys") and post-IP flow-through ("FT") lysate controls were run on the same gel. Caov-3 immunoprecipitates were also incubated with N-glycanase ("N-gly"), O-glycanase ("O-gly"), and/or sialidase ("S") (see FIG. 5F), where the blot was alternatively probed with biotinylated-DS6 and strepavidin-HRP.

FIG. 6 shows the results of immunoprecipitations and/or immunoblots of the DS6 antibody and the CM1 antibody on Caov-3 (FIG. 6A) and HeLa (FIG. 6B) cell lysates. Overlapping CM1 and DS6 western blot signals signify that the DS6 antigen is on the Muc1 protein. In HeLa lysates, the Muc1 doublet results from Muc1 expression directed by distinct alleles differing in their number of tandem repeats.

FIG. 7 shows a DS6 antibody sandwich ELISA design (FIG. 7A) and a standard curve (FIG. 7B). The standard curve was generated using known concentrations of commercially available CA15-3 standards (where 1 CA15-3 unit=1 DS6 unit).

FIG. 8 shows quantitative ELISA standard curves. The standard curves of the detection antibody (streptavidin-HRP/ biotin-DS6) signal (FIG. 8C) were determined using known concentrations of biotin-DS6 either captured by plated goat anti-mouse IgG (FIG. 8A) or bound directly onto the ELISA plate (FIG. 8B).

FIG. 9 shows the cDNA and amino acid sequences of the light chain (FIG. 9A) and heavy chain (FIG. 9B) variable region for the murine DS6 antibody. The three CDRs in each sequence are underlined (Kabat definitions).

FIG. 10 shows the light (FIG. 10A) and heavy chain (FIG. 10B) CDRs of the murine DS6 antibody determined by Kabat definitions. The AbM modeling software produces a slightly different definition for the heavy chain CDRs (FIG. 10c).

FIG. 11 shows the light chain ("muDS6LC") (residues 1-95 of SEQ ID NO:7) and heavy chain ("muDS6HC") (residues 1-98 of SEQ ID NO:9) amino acid sequences for the murine DS6 antibody aligned with the germline sequences for the IgVκap4 (SEQ ID NO:23) and IgVh J558.41 (SEQ ID NO:24) genes. Grey indicates sequence divergence.

FIG. 12 shows the ten light chain and heavy chain antibody sequences most homologous to the murine DS6 (muDS6) light chain ("muDS6LC") and heavy chain ("muDS6HC") sequences that have solved structure files in the Brookhaven database. Sequences are aligned in order of most to least homologous.

FIG. 13 shows surface accessibility data and calculations to predict which framework residues of the murine DS6 antibody light chain variable region are surface accessible. The positions with 25-35% average surface accessibility are marked (*??*) and were subjected to the second round analysis. DS6 antibody light chain variable region (FIG. 13A) and heavy chain variable region (FIG. 13B).

FIG. 15 shows amino acid sequences of murine ("muDS6") and humanized ("huDS6") (1.01 & 1.21) DS6 antibody light chain (FIG. 15A) and heavy chain (FIG. 15B) variable domains.

FIG. 16 shows the cDNA and amino acid sequences of the light chain variable region for the humanized DS6 antibody ("huDS6") (1.01 and 1.21).

FIG. 17 shows the cDNA and amino acid sequences of the heavy chain variable region for the humanized DS6 antibody ("huDS6") 1.01 (FIG. 17A) and 1.21 (FIG. 17B).

Figure 21:
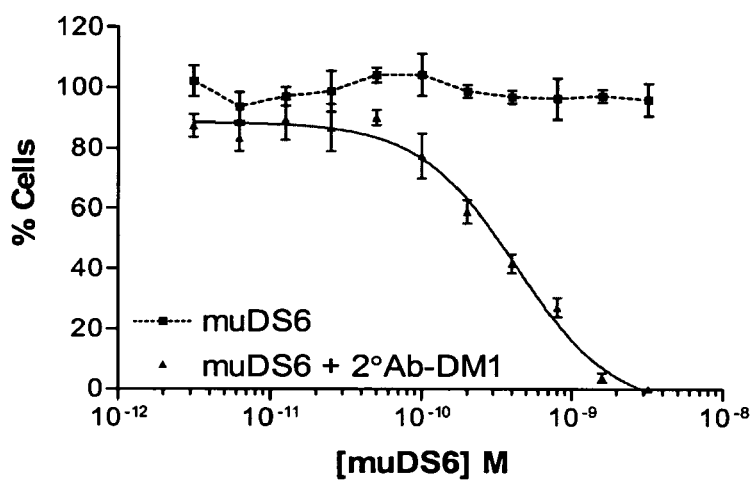

FIG. 21 shows the results of an indirect cell viability assay using the DS6 antibody in the presence or absence of the anti-mouse IgG (H+L) DM1 conjugate (2° Ab-DM1). Antigen-positive Caov-3 cells were killed in a DS6 antibody-dependent manner ($IC_{50}$=424.9 pM) only in the presence of the secondary conjugate ("DS6+2° Ab-DM1").

FIG. 22 shows the results of a complement-dependent cytotoxicity (CDC) assay of the muDS6 antibody. The results demonstrate that there is no CDC mediated effect of the DS6 antibody or on HPAC (FIG. 22A) and ZR-75-1 (FIG. 22B) cells.

Figure 23:
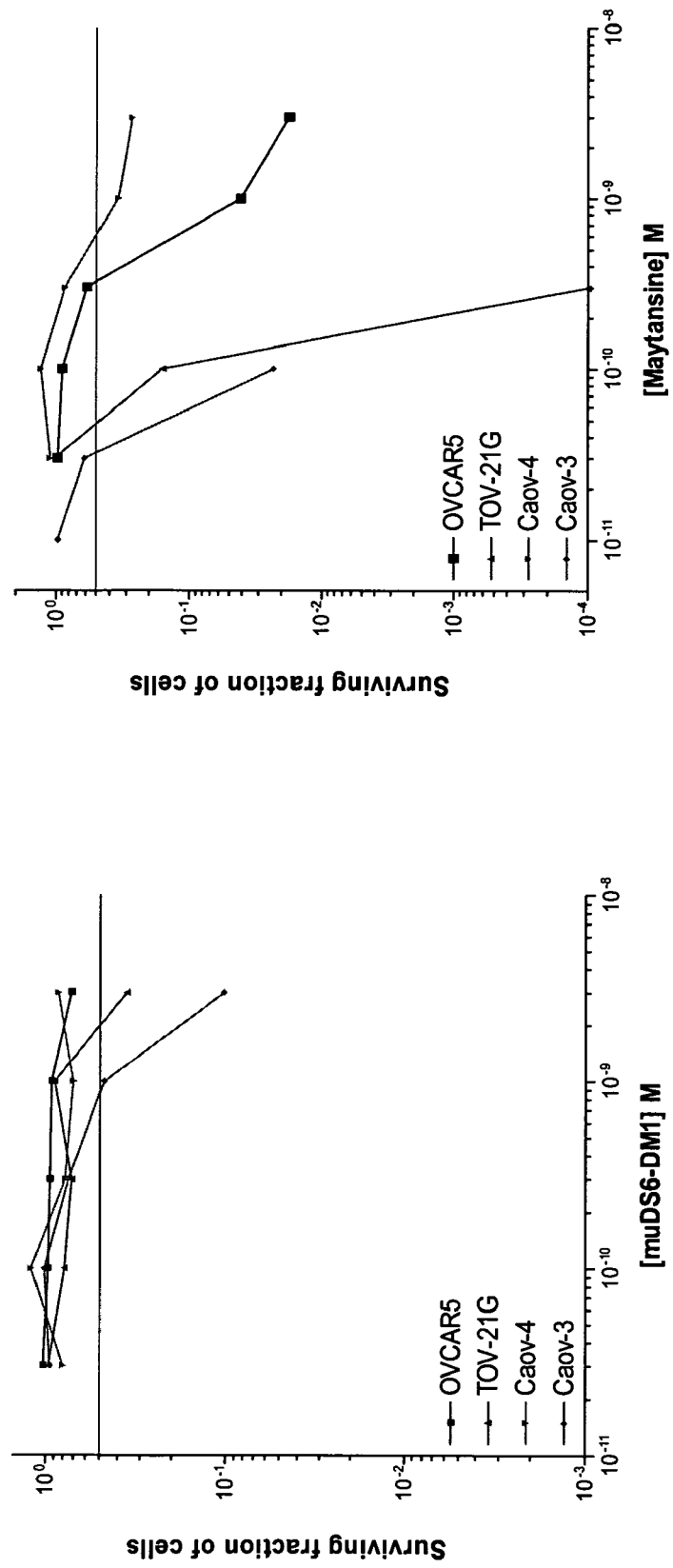
Figure 23:
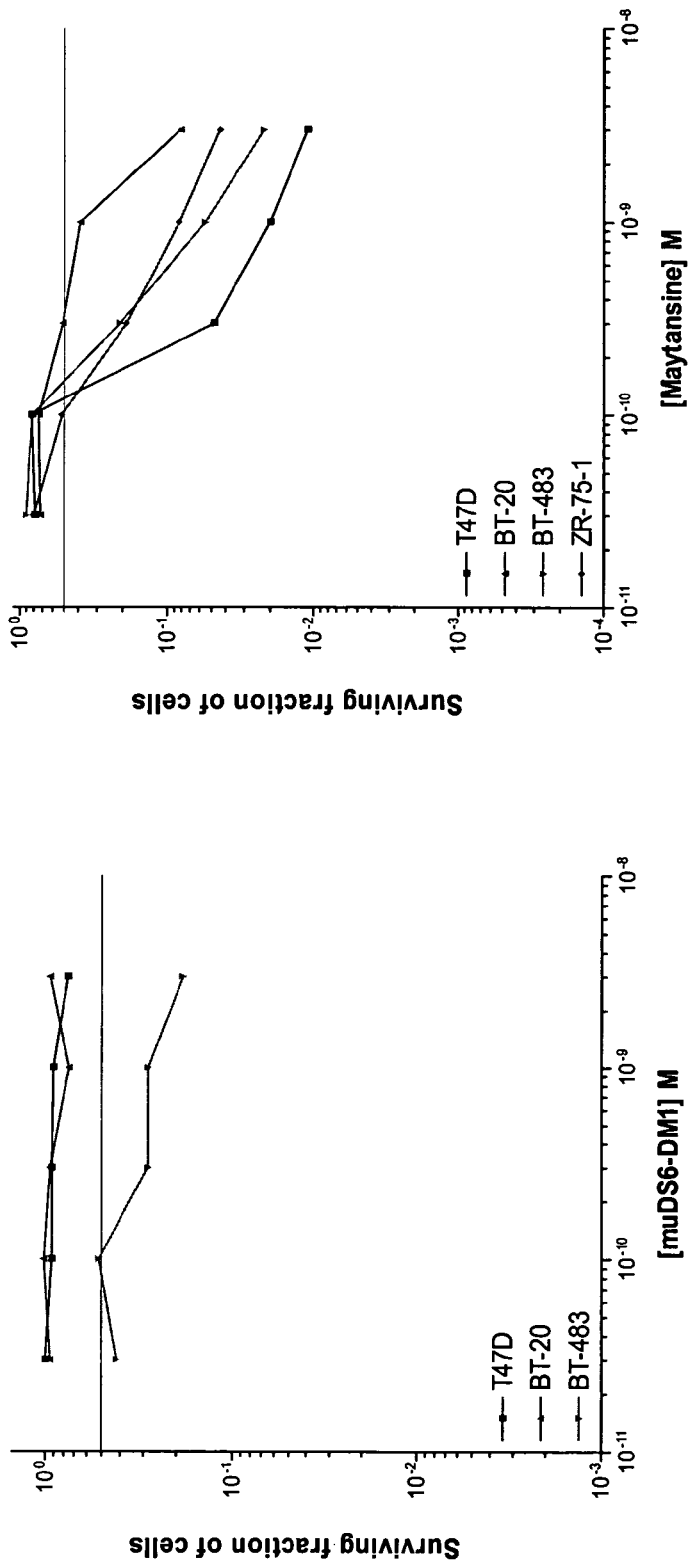
Figure 23:
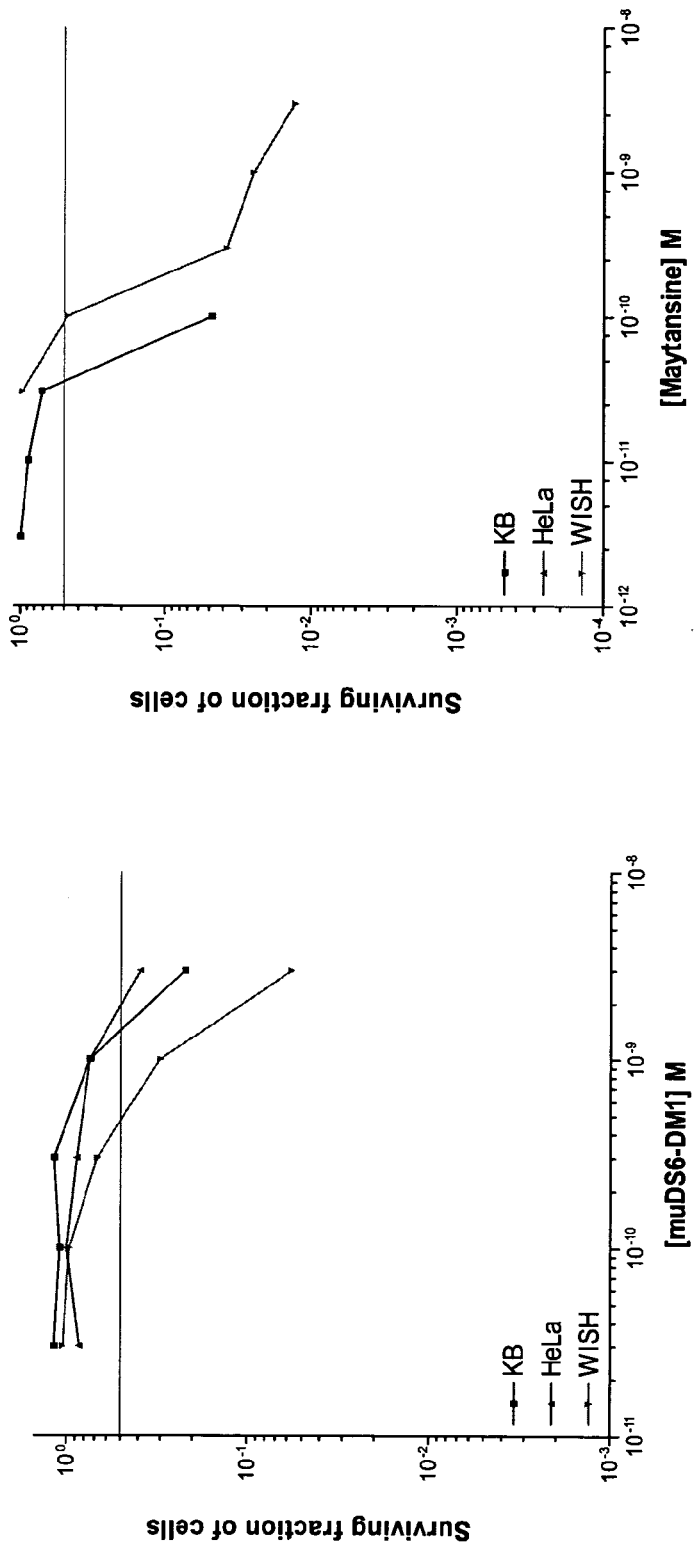
Figure 23:
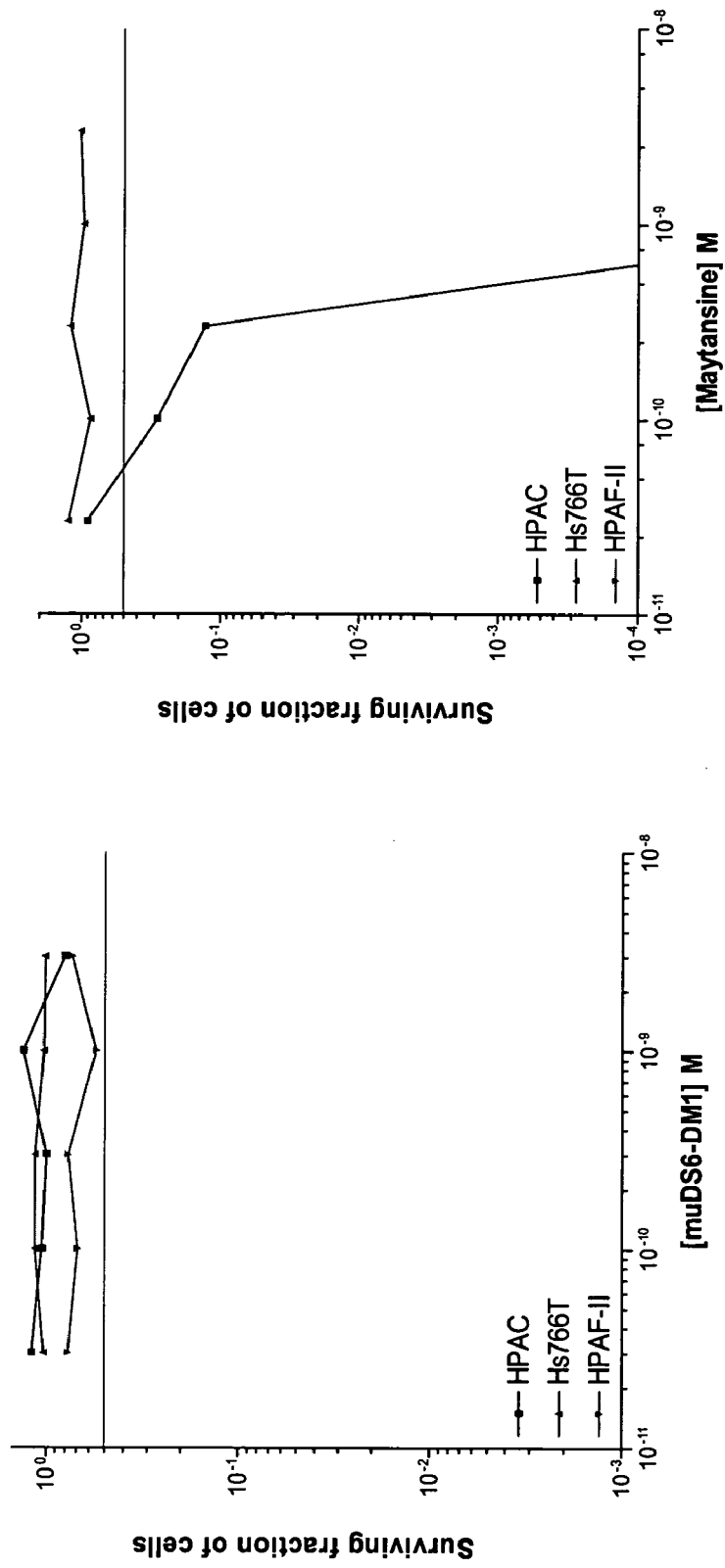

FIG. 23 shows the results of an in vitro cytotoxicity assay of a DS6 antibody-DM1 conjugate versus free maytansine. In a clonogenic assay, DS6 antigen-positive ovarian (FIG. 23A), breast (FIG. 23B), cervical (FIG. 23C), and pancreatic (FIG. 23D) cancer cell lines were tested for cytotoxicity of continuous exposure to a DS6 antibody-DM1 conjugate (left panels). These cell lines were similarly tested for maytansine sensitivity by a 72 h exposure to free maytansine (right panels). The ovarian cancer cell lines tested were OVCAR5, TOV-21G, Caov-4 and Caov-3. The breast cancer cell lines tested were T47D, BT-20 and BT-483. The cervical cancer cell lines tested were KB, HeLa and WISH. The pancreatic cancer cell lines tested were HPAC, Hs766T and HPAF-II.

Figure 24:
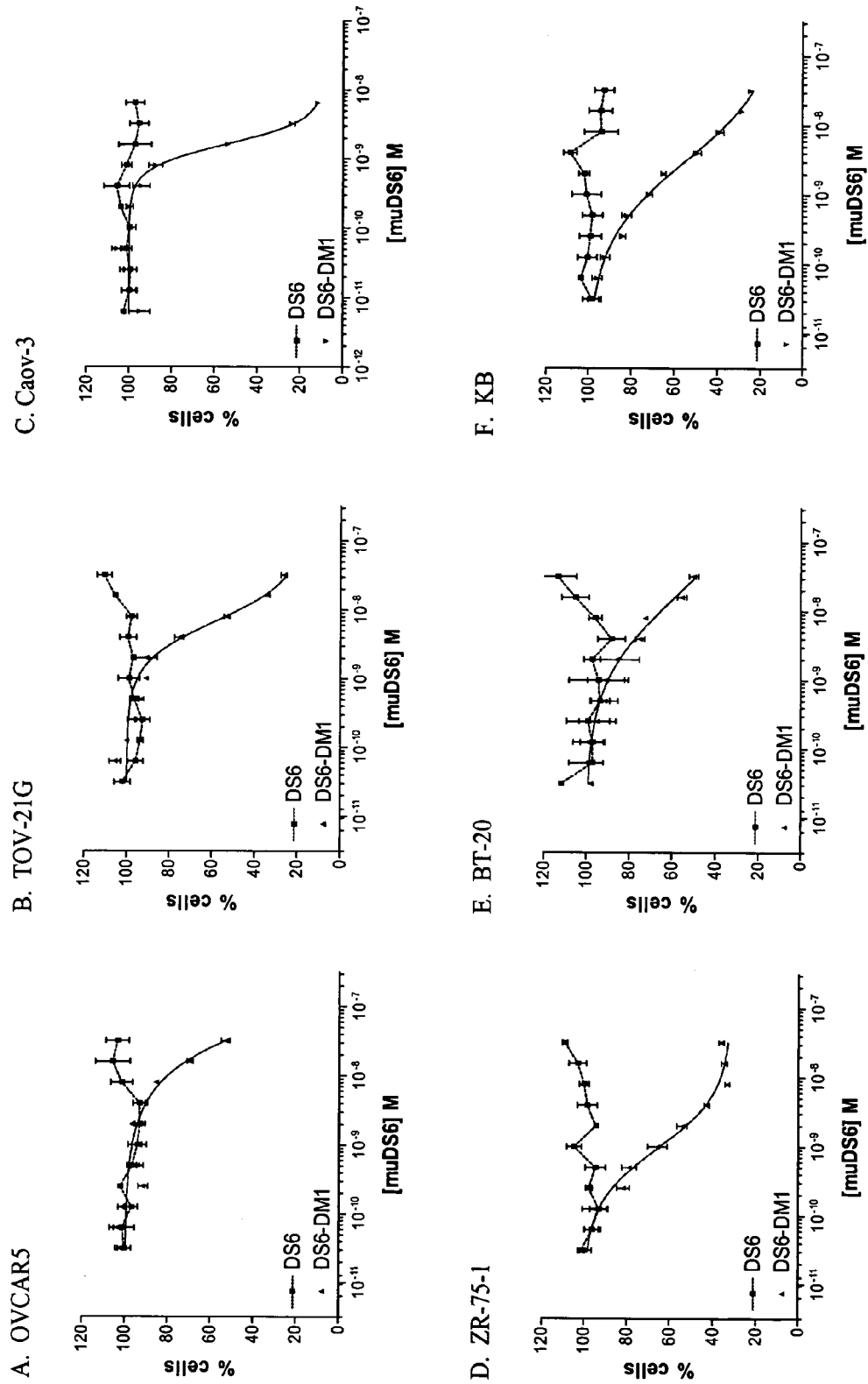

FIG. 24 shows the results of an in vitro cytotoxicity assay of a DS6 antibody-DM1 conjugate. In a MTT cell viability assay, human ovarian (FIG. 24A, FIG. 24B & FIG. 24C), breast (FIG. 24D & FIG. 24E), cervical (FIG. 24F & FIG. 24G), and pancreatic (FIG. 24H & FIG. 24I) cancer cells were killed in a DS6 antibody-DM1 conjugate-dependent manner. Naked DS6 did not adversely affect the growth of these cells, indicating that DM1 conjugation is required for the cytotoxicity.

FIG. 25A shows the results of an in vivo anti-tumor efficacy study of a DS6 antibody-DM1 conjugate on established subcutaneous KB tumor xenografts. Tumor cells were inoculated on day 0, and the first treatment was given on day 6. Immunoconjugate treatments continued daily for a total of 5 doses. PBS control animals were euthanized once tumor volumes exceeded 1500 $mm^3$. The conjugate was given at a dose of 150 or 225 µg/kg DM1, corresponding to antibody concentrations of 5.7 and 8.5 mg/kg respectively. The body weights (FIG. 25B) of the mice were monitored during the course of the study.

FIG. 26 shows the results of an antitumor efficacy study of a DS6 antibody-DM1 conjugate on established subcutaneous tumor xenografts. OVCAR5 (FIG. 26A and FIG. 26B), TOV-21G (FIG. 26C and FIG. 26D), HPAC (FIG. 26E and FIG. 26F), and HeLa (FIG. 26G and FIG. 26H) cells were inoculated on day 0, and immunoconjugate treatments were given on day 6 and 13. PBS control animals were euthanized once tumor volumes exceeded 1000 $mm^3$. The conjugate was given at a dose of 600 µg/kg DM1, corresponding to an antibody concentration 27.7 mg/kg. Tumor volume (FIG. 26A, FIG. 26C, FIG. 26E, and FIG. 26G) and body weight (FIG. 26B, FIG. 26D, FIG. 26F, and FIG. 26H) of the mice were monitored during the course of the study.

Figure 27:
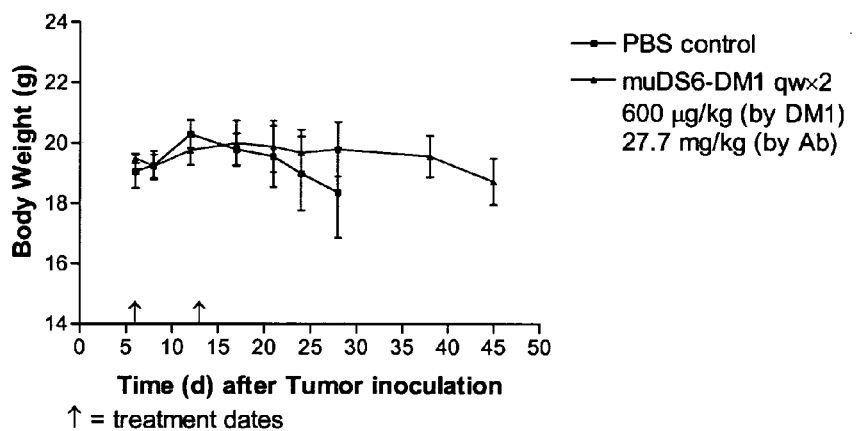

FIG. 27 shows the results of an in vivo efficacy study of a muDS6 antibody-DM1 conjugate on intraperitoneal OVCAR5 tumors. Tumor cells were injected intraperitoneally on day 0, and immunoconjugate treatments were given on day 6 and 13. Animals were euthanized once body weight loss exceeded 20%.

Figure 28:
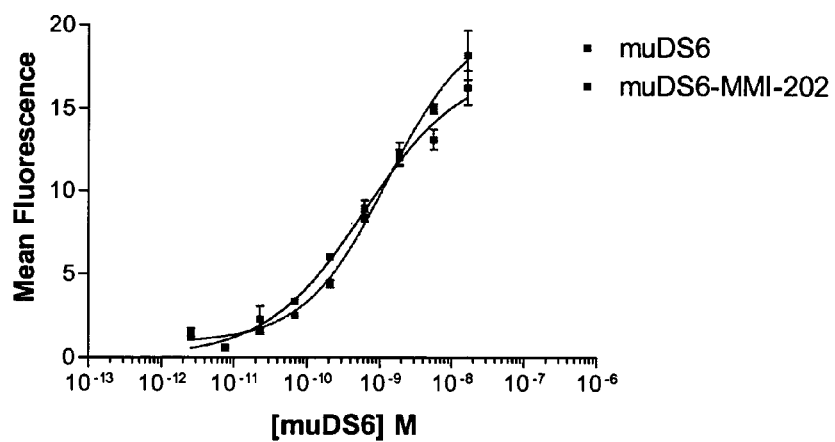

FIG. 28 shows the flow cytometry binding curve from a study of the binding affinity of naked and taxane-conjugated DS6 antibody on HeLa cells. Taxane (MM1-202)-conjugation does not adversely affect the binding affinity of the antibody. The apparent Kd of the DS6-MM1-202 conjugate (1.24 nM) was slightly greater than the naked DS6 antibody (620 pM).

FIG. 29 shows in vitro binding and potency of humanized DS6 version 1.01 antibody conjugate. Conjugation of huDS6v1.01 with DM4 has little effect on the avidity of huDS6v1.01 for KB cells (FIG. 29A). huDS6v1.01-DM4 shows potent in vitro cytotoxicity toward DS6-expressing WISH cells with an $IC_{50}$ of 0.44 nM (FIG. 29B).

FIG. 30 shows the results of an in vivo efficacy study with huDS6v1.01-DM4 conjugate in an HPAC pancreatic cancer model. huDS6v1.01-DM4 showed potent anti-tumor activity whereas the B4-DM4 control conjugate whose target is not expressed in the HPAC model had essentially no activity (FIG. 30A). The administered dose of 200 µg/kg was not toxic to the animals as indicated by the lack of weight loss (FIG. 30B).

DETAILED DESCRIPTION OF THE INVENTION

The present invention provides, among other features, anti-CA6 monoclonal antibodies, anti-CA6 humanized antibodies, and fragments of the anti-CA6 antibodies. Each of the antibodies and antibody fragments of the present invention are designed to specifically recognize and bind the CA6 glycotope on the surface of a cell. CA6 is known to be expressed by many human tumors: 95% of serous ovarian carcinomas, 50% of endometrioid ovarian carcinomas, 50% of the neoplasms of the uterine cervix, 69% of the neoplasms of the endometrius, 80% of neoplasms of the vulva, 60% of breast carcinomas, 67% pancreatic tumors, and 48% of tumors of the urothelium, but is rarely expressed by normal human tissue.

A report by Kearse et al., *Int. J. Cancer* 88(6):866-872 (2000) misidentified the protein on which the CA6 epitope is found as an 80 kDa protein having an N-linked carbohydrate containing the CA6 epitope when they used a hybridoma supernatant to characterize it. Using purified DS6 we have since demonstrated that the CA6 epitope is found on an O-linked carbohydrate of a greater than 250 kDa non-disulfide-linked glycoprotein. Furthermore, the glycoprotein was identified as the mucin, Muc1. Because different Muc1 alleles have varying numbers of tandem repeats in the variable number tandem repeat (VNTR) domain cells often express two distinct Muc1 proteins of different size (Taylor-Papadimitriou, *Biochim. Biophys. Acta* 1455(2-3):301-13 (1999). Because of differences in the number of repeats in the VNTR domain as well as differences in glycosylation the molecular weight of Muc1 varies from cell line to cell line.

The susceptibility of CA6 immunoreactivity to periodic acid indicates CA6 is a carbohydrate epitope "glycotope." The additional susceptibility of CA6 immunoreactivity to treatment with neuraminidase from *Vibrio cholerae* indicates that the CA6 epitope is a sialic acid dependent glycotope, thus a "sialoglycotope."

Details of the characterization of CA6 can be found in the Example 2 (see below). Additional details on CA6 may be found in WO 02/16401; Wennerberg et al., *Am. J. Pathol.* 143(4):1050-1054 (1993); Smith et al., *Human Antibodies* 9:61-65 (1999); Kearse et al., *Int. J. Cancer* 88(6):866-872 (2000); Smith et al., *Int. J. Gynecol. Pathol.* 20(3):260-6 (2001); and Smith et al., *Appl. Immunohistochem. Mol. Morphol.* 10(2):152-8 (2002).

The present invention also includes cytotoxic conjugates comprising two primary components. The first component is a cell binding agent that recognizes and binds the CA6 glycotope. The cell binding agent should recognize the CA6 sialoglycotope on Muc1 with a high degree of specificity so that the cytotoxic conjugates recognize and bind only the cells for which they are intended. A high degree of specificity will allow the conjugates to act in a targeted fashion with little side-effects resulting from non-specific binding.

In another embodiment, the cell binding agent of the present invention also recognizes the CA6 glycotope with a high degree of affinity so that the conjugates will be in contact with the target cell for a sufficient period of time to allow the cytotoxic drug portion of the conjugate to act on the cell, and/or to allow the conjugates sufficient time in which to be internalized by the cell.

In a preferred embodiment, the cytotoxic conjugates comprise an anti-CA6 antibody as the cell binding agent, more preferably the murine DS6 anti-CA6 monoclonal antibody. In a more preferred embodiment, the cytotoxic conjugates comprises a humanized DS6 antibody or an epitope-binding fragment thereof. The DS6 antibody is able to recognize CA6 with a high degree of specificity and directs the cytotoxic agent to an abnormal cell or a tissue, such as cancer cells, in a targeted fashion.

The second component of the cytotoxic conjugates of the present invention is a cytotoxic agent. In preferred embodiments, the cytotoxic agent is a taxol, a maytansinoid such as DM1 or DM4, CC-1065 or a CC-1065 analog. In preferred embodiments, the cell binding agents of the present invention are covalently attached, directly or via a cleavable or non-cleavable linker, to the cytotoxic agent.

The cell binding agents, cytotoxic agents, and linkers are discussed in more detail below.

Cell Binding Agents

The effectiveness of the compounds of the present invention as therapeutic agents depends on the careful selection of an appropriate cell binding agent. Cell binding agents may be of any kind presently known, or that become known and includes peptides and non-peptides. The cell binding agent may be any compound that can bind a cell, either in a specific or non-specific manner. Generally, these can be antibodies (especially monoclonal antibodies), lymphokines, hormones, growth factors, vitamins, nutrient-transport molecules (such as transferrin), or any other cell binding molecule or substance.

More specific examples of cell binding agents that can be used include:
(a) polyclonal antibodies;
(b) monoclonal antibodies;
(c) fragments of antibodies such as Fab, Fab', and F(ab')$_2$, Fv (Parham, *J. Immunol.* 131:2895-2902 (1983); Spring et al. *J. Immunol.* 113:470-478 (1974); Nisonoff et al. *Arch. Biochem. Biophys.* 89:230-244 (1960));
(d) interferons (e.g. alpha., .beta., gamma.);
(e) lymphokines such as IL-2, IL-3, IL-4, IL-6;
(f) hormones such as insulin, TRH (thyrotropin releasing hormone), MSH (melanocyte-stimulating hormone), steroid hormones, such as androgens and estrogens;
(g) growth factors and colony-stimulating factors such as EGF, TGF-alpha, FGF, VEGF, G-CSF, M-CSF and GM-CSF (Burgess, *Immunology Today* 5:155-158 (1984));
(h) transferrin (O'Keefe et al. *J. Biol. Chem.* 260:932-937 (1985)); and
(i) vitamins, such as folate.

Antibodies

Selection of the appropriate cell binding agent is a matter of choice that depends upon the particular cell population that is to be targeted, but in general, antibodies are preferred if an appropriate one is available or can be prepared, more preferably a monoclonal antibody.

Monoclonal antibody techniques allow for the production of extremely specific cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587).

A typical antibody is comprised of two identical heavy chains and two identical light chains that are joined by disulfide bonds. The variable region is a portion of the antibody heavy chains and light chains that differs in sequence among antibodies and that cooperates in the binding and specificity of each particular antibody for its antigen. Variability is not usually evenly distributed throughout antibody variable regions. It is typically concentrated within three segments of a variable region called complementarity-determining regions (CDRs) or hypervariable regions, both in the light chain and the heavy chain variable regions. The more highly conserved portions of the variable regions are called the framework regions. The variable regions of heavy and light chains comprise four framework regions, largely adopting a beta-sheet configuration, with each framework region connected by the three CDRs, which form loops connecting the beta-sheet structure, and in some cases forming part of the beta-sheet structure. The CDRs in each chain are held in close proximity by the framework regions and, with the CDRs from the other chain, contribute to the formation of the antigen binding site of antibodies (E. A. Kabat et al. Sequences of Proteins of Immunological Interest, Fifth Edition, 1991, NIH).

The constant region is a portion of the heavy chain. While not involved directly in binding an antibody to an antigen, it does exhibit various effector functions, such as participation of the antibody in antibody-dependent cellular toxicity.

A suitable monoclonal antibody for use in the present invention includes the murine DS6 monoclonal antibody (U.S. Pat. No. 6,596,503; ATCC deposit number PTA-4449).

Humanized or Resurfaced DS6 Antibodies

Preferably, a humanized anti-CA6 antibody is used as the cell binding agent of the present invention. A preferred embodiment of such a humanized antibody is a humanized DS6 antibody, or an epitope-binding fragment thereof.

The goal of humanization is a reduction in the immunogenicity of a xenogenic antibody, such as a murine antibody, for introduction into a human, while maintaining the full antigen binding affinity and specificity of the antibody.

Humanized antibodies may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Strategies and methods for the resurfacing of antibodies, and other methods for reducing immunogenicity of antibodies within a different host, are disclosed in U.S. Pat. No. 5,639,641 (Pedersen et al.), which is hereby incorporated in its entirety by reference. Briefly, in a preferred method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity-determining regions of the rodent antibody; and (5) the humanized rodent antibody having binding specificity is produced.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, Molecular Immunology 28(4/5):489-498; Studnicka G. M. et al., 1994, Protein Engineering 7(6):805-814; Roguska M. A. et al., 1994, PNAS 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

In preferred embodiment, the present invention provides humanized antibodies or fragments thereof that recognizes a novel sialoglycotope (the CA6 glycotope) on the Muc1 mucin. In another embodiment, the humanized antibodies or epitope-binding fragments thereof have the additional ability to inhibit growth of a cell expressing the CA6 glycotope.

In more preferred embodiments, there are provided resurfaced or humanized versions of the DS6 antibody wherein surface-exposed residues of the antibody or its fragments are replaced in both light and heavy chains to more closely resemble known human antibody surfaces. The humanized DS6 antibodies or epitope-binding fragments thereof of the present invention have improved properties. For example, humanized DS6 antibodies or epitope-binding fragments thereof specifically recognize a novel sialoglycotope (the CA6 glycotope) on the Muc1 mucin. More preferably, the humanized DS6 antibodies or epitope-binding fragments thereof have the additional ability to inhibit growth of a cell expressing the CA6 glycotope. The humanized antibody or an epitope-binding fragment thereof can be conjugated to a drug, such as a maytansinoid, to form a prodrug having specific cytotoxicity towards antigen-expressing cells by targeting the drug to the novel Muc1 sialoglycotope, CA6. Cytotoxic conjugates comprising such antibodies and a small, highly toxic drug (e.g., maytansinoids, taxanes, and CC-1065 analogs) can be used as a therapeutic for treatment of tumors, such as breast and ovarian tumors.

The humanized versions of the DS6 antibody are also fully characterized herein with respect to their respective amino acid sequences of both light and heavy chain variable regions, the DNA sequences of the genes for the light and heavy chain variable regions, the identification of the CDRs, the identification of their surface amino acids, and disclosure of a means for their expression in recombinant form.

In one embodiment, there is provided a humanized antibody or epitope-binding fragment thereof having a heavy chain including CDRs having amino acid sequences represented by SEQ ID NOs:1-3:

```
                                            (SEQ ID NO: 1)
    S Y N M H (SEQ ID NO: 2)
    Y I Y P G N G A T N Y N Q K F K G (SEQ ID NO: 3)
    G D S V P F A Y
```

When the heavy chain CDRs are determined by the AbM modeling software they are represented by SEQ ID NOs:20-22:

```
                                            (SEQ ID NO: 20)
    G Y T F T S Y N M H (SEQ ID NO: 21)
    Y I Y P G N G A T N (SEQ ID NO: 22)
    G D S V P F A Y
```

In the same embodiment, the humanized antibody or epitope-binding fragment thereof has a light chain that comprises CDRs having amino acid sequences represented by SEQ ID NOS:4-6:

```
                                            (SEQ ID NO: 4)
    S A H S S V S F M H (SEQ ID NO: 5)
    S T S S L A S (SEQ ID NO: 6)
    Q Q R S S F P L T
```

Also provided are humanized antibodies and epitope-binding fragments thereof having a light chain variable region that has an amino acid sequence that shares at least 90% sequence identity with an amino acid sequence represented by SEQ ID NO:7 or SEQ ID NO:8:

```
                                            (SEQ ID NO: 7)
QIVLTQSPAIMSASPGEKVTITCSAHSSVSFMHWFQQKPGTSPKLWIYST

SSLASGVPARFGGSGSGTSYSLTISRMEAEDAATYYCQQRSSFPLTFGAG

TKLELKR.

(SEQ ID NO: 8)
EIVLTQSPATMSASPGERVTITCSAHSSVSFMHWFQQKPGTSPKLWIYST

SSLASGVPARFGGSGSGTSYSLTISSMEAEDAATYYCQQRSSFPLTFGAG

TKLELKR.
```

Similarly, there are provided humanized antibodies and epitope-binding fragments thereof having a heavy chain variable region that has an amino acid sequence that shares at least 90% sequence identity with an amino acid sequence represented by SEQ ID NO:9, SEQ ID NO:10, or SEQ ID NO:11:

```
                                              (SEQ ID NO: 9)
QAYLQQSGAELVRSGASVKMSCKASGYTFTSYNMHWVKQTPGQGLEWIGY

IYPGNGATNYNQKFKGKATLTADPSSSTAYMQISSLTSEDSAVYFCARGD

SVPFAYWGQGTLVTVSA.

(SEQ ID NO: 10)
QAQLVQSGAEVVKPGASVKMSCKASGYTFTSYNMHWVKQTPGQGLEWIGY

IYPGNGATNYNQKFQGKATLTADTSSSTAYMQISSLTSEDSAVYFCARGD

SVPFAYWGQGTLVTVSA.

(SEQ ID NO: 11)
QAQLVQSGAEVVKPGASVKMSCKASGYTFTSYNMHWVKQTPGQGLEWIGY

IYPGNGATNYNQKFQGKATLTADPSSSTAYMQISSLTSEDSAVYFCARGD

SVPFAYWGQGTLVTVSA.
```

In another embodiment, humanized antibodies and epitope-binding fragments thereof are provided having a humanized or resurfaced light chain variable region having an amino acid sequence corresponding to SEQ ID NO: 8

```
                                              (SEQ ID NO: 8)
EIVLTQSPATMSASPGERVTITCSAHSSVSFMHWFQQKPGTSPKLWIYST

SSLASGVPARFGGSGSGTSYSLTISSMEAEDAATYYCQQRSSFPLTFGAG

TKLELKR.
```

Similarly, humanized antibodies and epitope-binding fragments thereof are provided having a humanized or resurfaced heavy chain variable region having an amino acid sequence corresponding to SEQ ID NO: 10 or SEQ ID NO:11:

```
                                              (SEQ ID NO: 10)
QAQLVQSGAEVVKPGASVKMSCKASGYTFTSYNMHWVKQTPGQGLEWIGY

IYPGNGATNYNQKFQGKATLTADTSSSTAYMQISSLTSEDSAVYFCARGD

SVPFAYWGQGTLVTVSA.

(SEQ ID NO: 11)
QAQLVQSGAEVVKPGASVKMSCKASGYTFTSYNMHWVKQTPGQGLEWIGY

IYPGNGATNYNQKFQGKATLTADPSSSTAYMQISSLTSEDSAVYFCARGD

SVPFAYWGQGTLVTVSA.
```

The humanized antibodies and epitope-binding fragments thereof of the present invention can also include versions of light and/or heavy chain variable regions in which human surface amino acid residues in proximity to the CDRs are replaced by the corresponding muDS6 surface residues at one or more positions defined by the residues in Table 1 (Kabat numbering) marked with an asterisk in order to retain the binding affinity and specificity of muDS6.

TABLE 1

| muDS6 framework residues proximal to a CDR (Kabat numbering) ||
|---|---|
| Light chain | Heavy chain |
| Q1* | Q1 |
| V3 | K64* |

TABLE 1-continued

| muDS6 framework residues proximal to a CDR (Kabat numbering) ||
|---|---|
| Light chain | Heavy chain |
| T5 | P73* |
| P40 | S74 |
| G57 | |
| A60 | |
| S67 | |
| E81 | |

The primary amino acid and DNA sequences of the DS6 antibody light and heavy chains, and of humanized versions thereof, are disclosed herein. However, the scope of the present invention is not limited to antibodies and fragments comprising these sequences. Instead, all antibodies and fragments that specifically bind to CA6 as a unique tumor-specific glycotope on the Muc1 receptor are included in the present invention. Preferably, the antibodies and fragments that specifically bind to CA6 also antagonize the biological activity of the receptor. More preferably, such antibodies further are substantially devoid of agonist activity. Thus, antibodies and antibody fragments of the present invention may differ from the DS6 antibody or the humanized derivatives thereof, in the amino acid sequences of their scaffold, CDRs, and/or light chain and heavy chain, and still fall within the scope of the present invention.

The CDRs of the DS6 antibody are identified by modeling and their molecular structures have been predicted. Again, while the CDRs are important for epitope recognition, they are not essential to the antibodies and fragments of the invention. Accordingly, antibodies and fragments are provided that have improved properties produced by, for example, affinity maturation of an antibody of the present invention.

The mouse light chain IgVκ ap4 germline gene and heavy chain IgVh J558.41 germline gene from which DS6 was likely derived are shown in FIG. 11 aligned with the sequence of the DS6 antibody. The comparison identifies probable somatic mutations in the DS6 antibody, including several in the CDRs.

The sequence of the heavy chain and light chain variable region of the DS6 antibody, and the sequences of the CDRs of the DS6 antibody were not previously known and are set forth in FIGS. 9A and 9B. Such information can be used to produce humanized versions of the DS6 antibody.

Antibody Fragments

The antibodies of the present invention include both the full length antibodies discussed above, as well as epitope-binding fragments. As used herein, "antibody fragments" include any portion of an antibody that retains the ability to bind to the epitope recognized by the full length antibody, generally termed "epitope-binding fragments." Examples of antibody fragments include, but are not limited to, Fab, Fab' and F(ab')$_2$, Fd, single-chain Fvs (scFv), single-chain antibodies, disulfide-linked Fvs (dsFv) and fragments comprising either a $V_L$ or $V_H$ region. Epitope-binding fragments, including single-chain antibodies, may comprise the variable region(s) alone or in combination with the entirety or a portion of the following: hinge region, $C_H1$, $C_H2$, and $C_H3$ domains.

Such fragments may contain one or both Fab fragments or the F(ab')$_2$ fragment. Preferably, the antibody fragments contain all six CDRs of the whole antibody, although fragments containing fewer than all of such regions, such as three, four or five CDRs, are also functional. Further, the fragments may be or may combine members of any one of the following immunoglobulin classes: IgG, IgM, IgA, IgD, or IgE, and the subclasses thereof.

Fab and F(ab')$_2$ fragments may be produced by proteolytic cleavage, using enzymes such as papain (Fab fragments) or pepsin (F(ab')$_2$ fragments).

The single-chain FVs (scFvs) fragments are epitope-binding fragments that contain at least one fragment of an antibody heavy chain variable region ($V_H$) linked to at least one fragment of an antibody light chain variable region ($V_L$). The linker may be a short, flexible peptide selected to assure that the proper three-dimensional folding of the ($V_L$) and ($V_H$) regions occurs once they are linked so as to maintain the target molecule binding-specificity of the whole antibody from which the single-chain antibody fragment is derived. The carboxyl terminus of the ($V_L$) or ($V_H$) sequence may be covalently linked by a linker to the amino acid terminus of a complementary ($V_L$) or ($V_H$) sequence.

Single-chain antibody fragments of the present invention contain amino acid sequences having at least one of the variable or complementarity determining regions (CDRs) of the whole antibodies described in this specification, but are lacking some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Single-chain antibody fragments may be generated by molecular cloning, antibody phage display library or similar techniques well known to the skilled artisan. These proteins may be produced, for example, in eukaryotic cells or prokaryotic cells, including bacteria. The epitope-binding fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled antigen bound or captured to a solid surface or bead. Phage used in these methods are typically filamentous phage including fd and M13 binding domains expressed from phage with Fab, Fv or disulfide-stabilized Fv antibody domains recombinantly fused to either the phage gene III or gene VIII protein.

Examples of phage display methods that can be used to make the epitope-binding fragments of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology, e.g., as described in detail below. For example, techniques to recombinantly produce Fab, Fab' and F(ab')$_2$ fragments can also be employed using methods known in the art such as those disclosed in PCT publication WO 92/22324; Mullinax et al., 1992, BioTechniques 12(6):864-869; Sawai et al., 1995, AJRI 34:26-34; and Better et al., 1988, Science 240: 1041-1043; said references incorporated by reference in their entireties. Examples of techniques which can be used to produce single-chain Fvs and antibodies include those described in U.S. Pat. Nos. 4,946,778 and 5,258,498; Huston et al., 1991, Methods in Enzymology 203:46-88; Shu et al., 1993, PNAS 90:7995-7999; Skerra et al., 1988, Science 240:1038-1040.

Functional Equivalents

Also included within the scope of the invention are functional equivalents of the anti-CA6 antibody and the humanized anti-CA6 antibody. The term "functional equivalents" includes antibodies with homologous sequences, chimeric antibodies, artificial antibodies and modified antibodies, for example, wherein each functional equivalent is defined by its ability to bind to CA6. The skilled artisan will understand that there is an overlap in the group of molecules termed "antibody fragments" and the group termed "functional equivalents." Methods of producing functional equivalents are disclosed, for example, in PCT Application WO 93/21319, European Patent Application No. 239,400; PCT Application WO 89/09622; European Patent Application 338,745; and European Patent Application EP 332,424, which are incorporated in their respective entireties by reference.

Antibodies with homologous sequences are those antibodies with amino acid sequences that have sequence homology with amino acid sequence of an anti-CA6 antibody and a humanized anti-CA6 antibody of the present invention. Preferably homology is with the amino acid sequence of the variable regions of the anti-CA6 antibody and humanized anti-CA6 antibody of the present invention. "Sequence homology" as applied to an amino acid sequence herein is defined as a sequence with at least about 90%, 91%, 92%, 93%, or 94% sequence homology, and more preferably at least about 95%, 96%, 97%, 98%, or 99% sequence homology to another amino acid sequence, as determined, for example, by the FASTA search method in accordance with Pearson and Lipman, Proc. Natl. Acad. Sci. USA 85, 2444-2448 (1988).

As used herein, a chimeric antibody is one in which different portions of an antibody are derived from different animal species. For example, an antibody having a variable region derived from a murine monoclonal antibody paired with a human immunoglobulin constant region. Methods for producing chimeric antibodies are known in the art. See, e.g., Morrison, 1985, Science 229:1202; Oi et al., 1986, BioTechniques 4:214; Gillies et al., 1989, J. Immunol. Methods 125:

191-202; U.S. Pat. Nos. 5,807,715; 4,816,567; and 4,816,397, which are incorporated herein by reference in their entireties.

Humanized forms of chimeric antibodies are made by substituting the complementarity determining regions of, for example, a mouse antibody, into a human framework domain, e.g., see PCT Pub. No. WO92/22653. Humanized chimeric antibodies preferably have constant regions and variable regions other than the complementarity determining regions (CDRs) derived substantially or exclusively from the corresponding human antibody regions and CDRs derived substantially or exclusively from a mammal other than a human.

Artificial antibodies include scFv fragments, diabodies, triabodies, tetrabodies and mru (see reviews by Winter, G. and Milstein, C., 1991, Nature 349: 293-299; Hudson, P. J., 1999, Current Opinion in Immunology 11: 548-557), each of which has antigen-binding ability. In the single chain Fv fragment (scFv), the $V_H$ and $V_L$ domains of an antibody are linked by a flexible peptide. Typically, this linker peptide is about 15 amino acid residues long. If the linker is much smaller, for example 5 amino acids, diabodies are formed, which are bivalent scFv dimers. If the linker is reduced to less than three amino acid residues, trimeric and tetrameric structures are formed that are called triabodies and tetrabodies. The smallest binding unit of an antibody is a CDR, typically the CDR2 of the heavy chain which has sufficient specific recognition and binding that it can be used separately. Such a fragment is called a molecular recognition unit or mru. Several such mrus can be linked together with short linker peptides, therefore forming an artificial binding protein with higher avidity than a single mru.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, phosphorylation, amidation, derivatization by known protecting/blocking groups, proteolytic cleavage, linkage to a cellular ligand or other protein, etc. The covalent attachment does not prevent the antibody from generating an anti-idiotypic response. These modifications may be carried out by known techniques, including, but not limited to, specific chemical cleavage, acetylation, formylation, metabolic synthesis of tunicamycin, etc. Additionally, the modified antibodies may contain one or more non-classical amino acids.

Functional equivalents may be produced by interchanging different CDRs on different chains within different frameworks. Thus, for example, different classes of antibody are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework.

Functional equivalents may be readily produced by mutation, deletion and/or insertion within the variable and/or constant region sequences that flank a particular set of CDRs, using a wide variety of methods known in the art.

The antibody fragments and functional equivalents of the present invention encompass those molecules with a detectable degree of binding to CA6, when compared to the DS6 antibody. A detectable degree of binding includes all values in the range of at least 10-100%, preferably at least 50%, 60% or 70%, more preferably at least 75%, 80%, 85%, 90%, 95% or 99% the binding ability of the murine DS6 antibody to CA6.

Improved Antibodies

The CDRs are of primary importance for epitope recognition and antibody binding. However, changes may be made to the residues that comprise the CDRs without interfering with the ability of the antibody to recognize and bind its cognate epitope. For example, changes that do not affect epitope recognition, yet increase the binding affinity of the antibody for the epitope may be made.

Thus, also included in the scope of the present invention are improved versions of both the murine and humanized antibodies, which also specifically recognize and bind CA6, preferably with increased affinity.

Several studies have surveyed the effects of introducing one or more amino acid changes at various positions in the sequence of an antibody, based on the knowledge of the primary antibody sequence, on its properties such as binding and level of expression (Yang, W. P. et al., 1995, J. Mol. Biol., 254, 392-403; Rader, C. et al., 1998, Proc. Natl. Acad. Sci. USA, 95, 8910-8915; Vaughan, T. J. et al., 1998, Nature Biotechnology, 16, 535-539).

In these studies, equivalents of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, Nature Biotechnology, 16, 535-539; Adey, N. B. et al., 1996, Chapter 16, pp. 277-291, in "Phage Display of Peptides and Proteins", Eds. Kay, B. K. et al., Academic Press). These methods of changing the sequence of the primary antibody have resulted in improved affinities of the secondary antibodies (Gram, H. et al., 1992, Proc. Natl. Acad. Sci. USA, 89, 3576-3580; Boder, E. T. et al., 2000, Proc. Natl. Acad. Sci. USA, 97, 10701-10705; Davies, J. and Riechmann, L., 1996, Immunotechnolgy, 2, 169-179; Thompson, J. et al., 1996, J. Mol. Biol., 256, 77-88; Short, M. K. et al., 2002, J. Biol. Chem., 277, 16365-16370; Furukawa, K. et al., 2001, J. Biol. Chem., 276, 27622-27628).

By a similar directed strategy of changing one or more amino acid residues of the antibody, the antibody sequences described in this invention can be used to develop anti-CA6 antibodies with improved functions, including improved affinity for CA6.

Improved antibodies also include those antibodies having improved characteristics that are prepared by the standard techniques of animal immunization, hybridoma formation and selection for antibodies with specific characteristics Cytotoxic Agents The cytotoxic agent used in the cytotoxic conjugate of the present invention may be any compound that results in the death of a cell, or induces cell death, or in some manner decreases cell viability. Preferred cytotoxic agents include, for example, maytansinoids and maytansinoid analogs, taxoids, CC-1065 and CC-1065 analogs, dolastatin and dolastatin analogs, defined below. These cytotoxic agents are conjugated to the antibodies, antibodies fragments, functional equivalents, improved antibodies and their analogs as disclosed herein The cytotoxic conjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the drug or prodrug.

Maytansinoids

Among the cytotoxic agents that may be used in the present invention to form a cytotoxic conjugate, are maytansinoids and maytansinoid analogs. Examples of suitable maytansinoids include maytansinol and maytansinol analogs. Maytansinoids are drugs that inhibit microtubule formation and that are highly toxic to mammalian cells.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Specific examples of suitable analogues of maytansinol having a modified aromatic ring include:

(1) C-19-dechloro (U.S. Pat. No. 4,256,746) (prepared by LAH reduction of ansamytocin P2);

(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl (demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from *Nocardia*);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

In a preferred embodiment, the cytotoxic conjugates of the present invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (I):

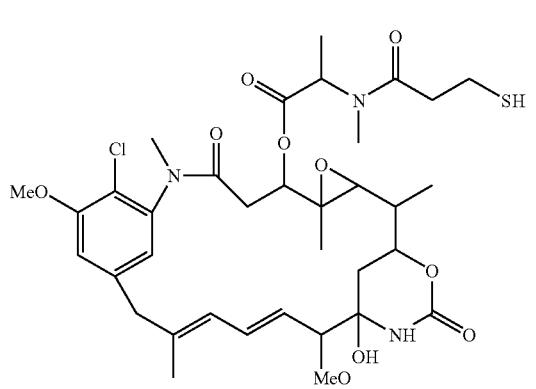

(I)

In another preferred embodiment, the cytotoxic conjugates of the present invention utilize the thiol-containing maytansinoid $N^{2'}$-deacetyl-$N^{2'}$-(4-methyl-4-mercapto-1-oxopentyl)-maytansine as the cytotoxic agent. DM4 is represented by the following structural formula (II):

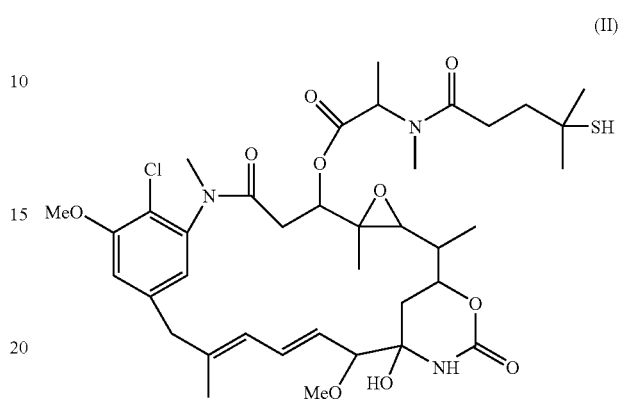

(II)

In further embodiments of the invention, other maytansines, including thiol and disulfide-containing maytansinoids bearing a mono or di-alkyl substitution on the carbon atom bearing the sulfur atom, may be used. These include a maytansinoid having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being CH3, C2H5, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Such additional maytansines include compounds represented by formula (III):

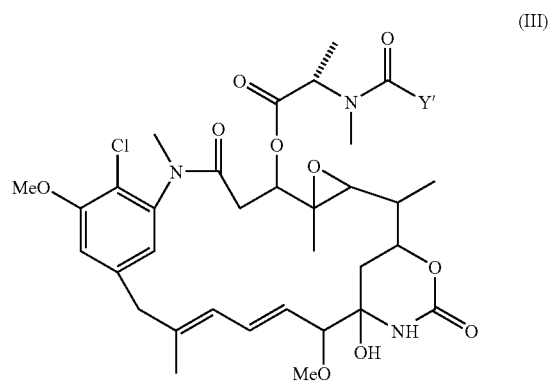

(III)

wherein:

Y' represents
$(CR_7R_8)_l(CR_9\!=\!CR_{10})_p(C\!\equiv\!C)_qA_o(CR_5R_6)_mD_u$
$(CR_{11}\!=\!CR_{12})_r(C\!\equiv\!C)_sB_t(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

A, B, D are cycloalkyl or cycloalkenyl having 3-10 carbon atoms, simple or substituted aryl or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m, n, o, p, q, r, s, and t are each independently 0 or an integer of from 1 to 5, provided that at least two of l, m, n, o, p, q, r, s t and u are not zero at any one time; and Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

Preferred embodiments of formula (III) include compounds of formula (III) wherein:

$R_1$ is methyl, $R_2$ is H and Z is H.

$R_1$ and $R_2$ are methyl and Z is H.

$R_1$ is methyl, $R_2$ is H, and Z is —$SCH_3$.

$R_1$ and $R_2$ are methyl, and Z is —$SCH_3$.

Such additional maytansines also include compounds represented by formula (IV-L), (IV-D), or (IV-D,L):

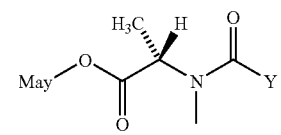

(IV-L)

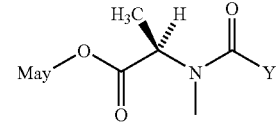

(IV-D)

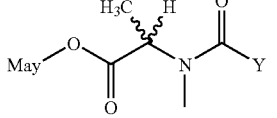

(IV-D, L)

wherein:

Y represents $(CR_7R_8)_l(CR_5R_6)_m(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical;

l, m and n are each independently an integer of from 1 to 5, and in addition n can be 0; and Z is H, SR or —COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocyclic radical; and May represents a maytansinoid which bears the side chain at C-3, C-14 hydroxymethyl, C-15 hydroxy or C-20 desmethyl.

Preferred embodiments of formulas (IV-L), (IV-D) and (IV-D,L) include compounds of formulas (IV-L), (IV-D) and (IV-D,L) wherein:

$R_1$ is methyl, $R_2$ is H, $R_5$, $R_6$, $R_7$, and $R_8$ are each H, l and m are each 1, n is 0, and Z is H.

$R_1$ and $R_2$ are methyl, $R_5$, $R_6$, $R_7$, $R_8$ are each H, l and m are 1, n is 0, and Z is H.

$R_1$ is methyl, $R_2$ is H, $R_5$, $R_6$, $R_7$, and $R_8$ are each H, l and m are each 1, n is 0, and Z is —$SCH_3$.

$R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (IV-L).

Such additional maytansines also include compounds represented by formula (V):

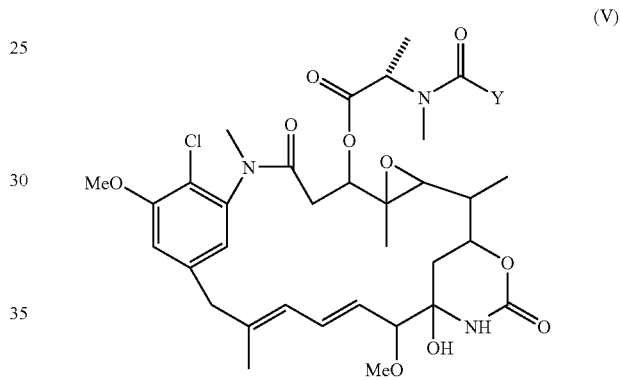

(V)

wherein:

Y represents $(CR_7R_8)_l(CR_5R_6)_m(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical;

l, m and n are each independently an integer of from 1 to 5, and in addition n can be 0; and Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

Preferred embodiments of formula (V) include compounds of formula (V) wherein:

$R_1$ is methyl, $R_2$ is H, R5, R6, R7, and R8 are each H; l and m are each 1; n is 0; and Z is H.

$R_1$ and $R_2$ are methyl; $R_5$, $R_6$, $R_7$, $R_8$ are each H, l and m are 1; n is 0; and Z is H.

$R_1$ is methyl, $R_2$ is H, $R_5$, $R_6$, $R_7$, and $R_8$ are each H, l and m are each 1, n is 0, and Z is —$SCH_3$.

$R_1$ and $R_2$ are methyl, $R_5$, $R_6$, $R_7$, $R_8$ are each H, l and m are 1, n is 0, and Z is —$SCH_3$.

Such additional maytansines further include compounds represented by formula (VI-L), (VI-D), or (VI-D,L):

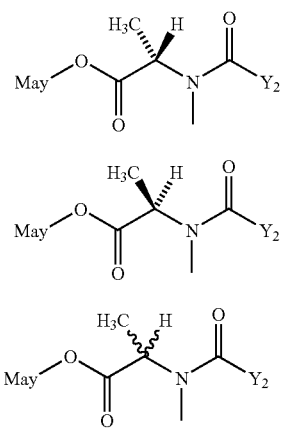

wherein:

$Y_2$ represents $(CR_7R_8)_l(CR_5R_6)_m(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

$Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical; and May is a maytansinoid.

Such additional maytansines also include compounds represented by formula (VII):

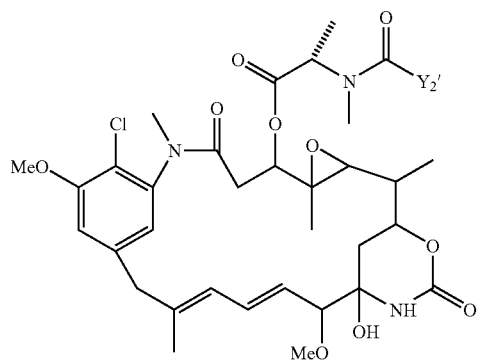

wherein:

$Y_2'$ represents $(CR_7R_8)_l(CR_9=CR_{10})_p(C\equiv C)A_qA_o(CR_5R_6)_mD_u$
$(CR_{11}=CR_{12})_r(C\equiv C)_sB_t(CR_3R_4)_nCR_1R_2SZ_2$, wherein:

$R_1$ and $R_2$ are each independently $CH_3$, $C_2H_5$, linear branched or alkyl or alkenyl having from 1 to 10 carbon atoms, cyclic alkyl or alkenyl having from 3 to 10 carbon atoms, phenyl, substituted phenyl or heterocyclic aromatic or heterocyclic radical, and in addition $R_2$ can be H;

A, B, and D each independently is cycloalkyl or cycloalkenyl having 3 to 10 carbon atoms, simple or substituted aryl, or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time; and $Z_2$ is SR or —COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocyclic radical.

Preferred embodiments of formula (VII) include compounds of formula (VII) wherein: $R_1$ is methyl and $R_2$ is H.

The above-mentioned maytansinoids can be conjugated to anti-CA6 antibody DS6, or a homologue or fragment thereof, wherein the antibody is linked to the maytansinoid using the thiol or disulfide functionality that is present on the acyl group of an acylated amino acid side chain found at C-3, C-14 hydroxymethyl, C-15 hydroxy or C-20 desmethyl of the maytansinoid, and wherein the acyl group of the acylated amino acid side chain has its thiol or disulfide functionality located at a carbon atom that has one or two substituents, said substituents being $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition one of the substituents can be H, and wherein the acyl group has a linear chain length of at least three carbon atoms between the carbonyl functionality and the sulfur atom.

A preferred conjugate of the present invention is the one that comprises the anti-anti-CA6 antibody DS6, or a homologue or fragment thereof, conjugated to a maytansinoid of formula (VIII):

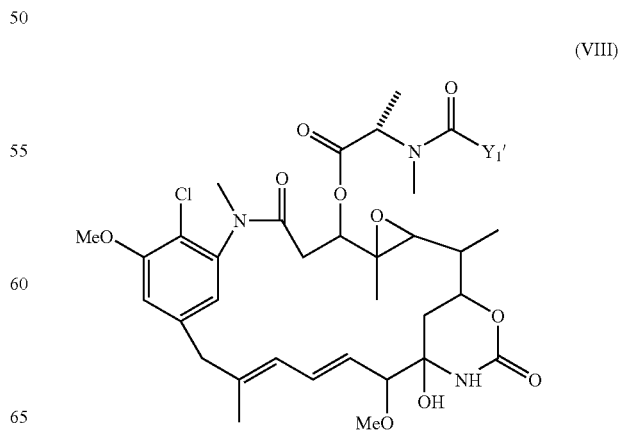

wherein:

$Y_1'$ represents $(CR_7R_8)_l(CR_9=CR_{10})_p(C\equiv C)A_qA_o(CR_5R_6)_mD_u$
$(CR_{11}=CR_{12})_r(C\equiv C)_sB_t(CR_3R_4)_nCR_1R_2S-$, wherein:

A, B, and D, each independently is cycloalkyl or cycloalkenyl having 3-10 carbon atoms, simple or substituted aryl, or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical; and l, m, n, o, p, q, r, s, t and u are each independently 0 or an integer of from 1 to 5, provided that at least two of l, m, n, o, p, q, r, s t, and u are non-not zero at any one time.

Preferably, $R_1$ is methyl and $R_2$ is H or $R_1$ and $R_2$ are methyl.

An even more preferred conjugate of the present invention is the one that comprises the anti-CA6 antibody DS6, or a homologue or fragment thereof, conjugated to a maytansinoid of formula (IX-L), (IX-D), or (IX-D,L):

(IX-L)

(IX-D)

(IX-D, L)

wherein:

$Y_1$ represents $(CR_7R_8)_l(CR_5R_6)_m(CR_3R_4)_nCR_1R_2S-$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0; and May represents a maytansinol which bears the side chain at C-3, C-14 hydroxymethyl, C-15 hydroxy or C-20 desmethyl.

Preferred embodiments of formulas (IX-L), (IX-D) and (IX-D,L) include compounds of formulas (IX-L), (IX-D) and (IX-D,L) wherein:

$R_1$ is methyl and $R_2$ is H or $R_1$ and $R_2$ are methyl, $R_1$ is methyl, $R_2$ is H, $R_5$, $R_6$, $R_7$ and $R_8$ are each H; l and m are each 1; n is 0, $R_1$ and $R_2$ are methyl; $R_5$, $R_6$, $R_7$ and $R_8$ are each H; l and m are 1; n is 0.

Preferably the cytotoxic agent is represented by formula (IX-L).

An further preferred conjugate of the present invention is the one that comprises the anti-CA6 antibody DS6, or a homologue or fragment thereof, conjugated to a maytansinoid of formula (X):

(X)

wherein the substituents are as defined for formula (IX) above.

Especially preferred are any of the above-described compounds, wherein $R_1$ is H, $R_2$ is methyl, $R_5$, $R_6$, $R_7$ and $R_8$ are each H, l and m are each 1, and n is 0.

Further especially preferred are any of the above-described compounds, wherein $R_1$ and $R_2$ are methyl, $R_5$, $R_6$, $R_7$, $R_8$ are each H, l and m are 1, and n is 0

Further, the L-aminoacyl stereoisomer is preferred.

Each of the maytansinoids taught in pending U.S. Pat. No. 7,276,497, filed May 20, 2004, may also be used in the cytotoxic conjugate of the present invention. The entire disclosure of U.S. Pat. No. 7,276,497 is incorporated herein by reference.

Disulfide-Containing Linking Groups

In order to link the maytansinoid to a cell binding agent, such as the DS6 antibody, the maytansinoid comprises a linking moiety. The linking moiety contains a chemical bond that allows for the release of fully active maytansinoids at a particular site. Suitable chemical bonds are well known in the art and include disulfide bonds, acid labile bonds, photolabile bonds, peptidase labile bonds and esterase labile bonds. Preferred are disulfide bonds.

The linking moiety also comprises a reactive chemical group. In a preferred embodiment, the reactive chemical group can be covalently bound to the maytansinoid via a disulfide bond linking moiety.

Particularly preferred reactive chemical groups are N-succinimidyl esters and N-sulfosuccinimidyl esters.

Particularly preferred maytansinoids comprising a linking moiety that contains a reactive chemical group are C-3 esters of maytansinol and its analogs where the linking moiety contains a disulfide bond and the chemical reactive group comprises a N-succinimidyl or N-sulfosuccinimidyl ester.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

While the synthesis of esters of maytansinol having a linking moiety is described in terms of disulfide bond-containing linking moieties, one of skill in the art will understand that linking moieties with other chemical bonds (as described above) can also be used with the present invention, as can other maytansinoids. Specific examples of other chemical bonds include acid labile bonds, photolabile bonds, peptidase labile bonds and esterase labile bonds. The disclosure of U.S. Pat. No. 5,208,020, incorporated herein, teaches the production of maytansinoids bearing such bonds.

The synthesis of maytansinoids and maytansinoid derivatives having a disulfide moiety that bears a reactive group is described in U.S. Pat. Nos. 6,441,163 and 6,333,410, and U.S. Pat. No. 7,368,565, each of which is herein incorporated by reference.

The reactive group-containing maytansinoids, such as DM1, are reacted with an antibody, such as the DS6 antibody, to produce cytotoxic conjugates. These conjugates may be purified by HPLC or by gel-filtration.

Several excellent schemes for producing such antibody-maytansinoid conjugates are provided in U.S. Pat. Nos. 6,333,410, 6,441,163, 7,368,565, and 6,716,821, each of which is incorporated herein in its entirety.

In general, a solution of an antibody in aqueous buffer may be incubated with a molar excess of maytansinoids having a disulfide moiety that bears a reactive group. The reaction mixture can be quenched by addition of excess amine (such as ethanolamine, taurine, etc.). The maytansinoid-antibody conjugate may then be purified by gel-filtration.

The number of maytansinoid molecules bound per antibody molecule can be determined by measuring spectrophotometrically the ratio of the absorbance at 252 nm and 280 nm. An average of 1-10 maytansinoid molecules/antibody molecule is preferred.

Conjugates of antibodies with maytansinoid drugs can be evaluated for their ability to suppress proliferation of various unwanted cell lines in vitro. For example, cell lines such as the human epidermoid carcinoma line A-431, the human small cell lung cancer cell line SW2, the human breast tumor line SKBR3 and the Burkitt's lymphoma line Namalwa can easily be used for the assessment of cytotoxicity of these compounds. Cells to be evaluated can be exposed to the compounds for 24 hours and the surviving fractions of cells measured in direct assays by known methods. $IC_{50}$ values can then be calculated from the results of the assays.

PEG-Containing Linking Groups

Maytansinoids may also be linked to cell binding agents using PEG linking groups, as set forth in U.S. Pat. No. 6,716,821. These PEG linking groups are soluble both in water and in non-aqueous solvents, and can be used to join one or more cytotoxic agents to a cell binding agent. Exemplary PEG linking groups include hetero-bifunctional PEG linkers that bind to cytotoxic agents and cell binding agents at opposite ends of the linkers through a functional sulfhydryl or disulfide group at one end, and an active ester at the other end.

As a general example of the synthesis of a cytotoxic conjugate using a PEG linking group, reference is again made to U.S. Pat. No. 6,716,821 for specific details. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group.

Taxanes

The cytotoxic agent used in the cytotoxic conjugates according to the present invention may also be a taxane or derivative thereof.

Taxanes are a family of compounds that includes paclitaxel (Taxol), a cytotoxic natural product, and docetaxel (Taxotere), a semi-synthetic derivative, two compounds that are widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell binding agents.

A preferred taxane for use in the preparation of cytotoxic conjugates is the taxane of formula (XI):

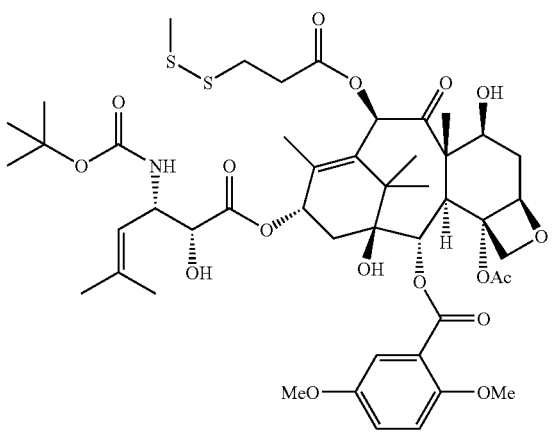

(XI)

Methods for synthesizing taxanes that may be used in the cytotoxic conjugates of the present invention, along with methods for conjugating the taxanes to cell binding agents such as antibodies, are described in detail in U.S. Pat. Nos. 5,416,064, 5,475,092, 6,340,701, 6,372,738, 6,436,931, 6,716,821, 6,596,757, 6,706,708 and 7,390,898, and in U.S. application Ser. No. 10/210,112, now abandoned.

CC-1065 Analogues

The cytotoxic agent used in the cytotoxic conjugates according to the present invention may also be CC-1065 or a derivative thereof.

CC-1065 is a potent anti-tumor antibiotic isolated from the culture broth of *Streptomyces zelensis*. CC-1065 is about 1000-fold more potent in vitro than are commonly used anticancer drugs, such as doxorubicin, methotrexate and vincristine (B. K. Bhuyan et al., *Cancer Res.*, 42, 3532-3537 (1982)). CC-1065 and its analogs are disclosed in U.S. Pat. Nos. 6,372,738, 6,340,701, 5,846,545 and 5,585,499.

The cytotoxic potency of CC-1065 has been correlated with its alkylating activity and its DNA-binding or DNA-intercalating activity. These two activities reside in separate parts of the molecule. Thus, the alkylating activity is contained in the cyclopropapyrroloindole (CPI) subunit and the DNA-binding activity resides in the two pyrroloindole subunits.

Although CC-1065 has certain attractive features as a cytotoxic agent, it has limitations in therapeutic use. Administration of CC-1065 to mice caused a delayed hepatotoxicity leading to mortality on day 50 after a single intravenous dose of 12.5 µg/kg {V. L. Reynolds et al., J. Antibiotics, XXIX, 319-334 (1986)}. This has spurred efforts to develop analogs that do not cause delayed toxicity, and the synthesis of simpler analogs modeled on CC-1065 has been described {M. A. Warpehoski et al., J. Med. Chem., 31, 590-603 (1988)}.

In another series of analogs, the CPI moiety was replaced by a cyclopropabenzindole (CBI) moiety {D. L. Boger et al., J. Org. Chem., 55, 5823-5833, (1990), D. L. Boger et al., Bio Org. Med. Chem. Lett., 1, 115-120 (1991)}. These compounds maintain the high in vitro potency of the parental drug, without causing delayed toxicity in mice. Like CC-1065, these compounds are alkylating agents that bind to the minor groove of DNA in a covalent manner to cause cell death. However, clinical evaluation of the most promising analogs, Adozelesin and Carzelesin, has led to disappointing results {B.F. Foster et al., Investigational New Drugs, 13, 321-326 (1996); I. Wolff et al., Clin. Cancer Res., 2, 1717-1723 (1996)}. These drugs display poor therapeutic effects because of their high systemic toxicity.

The therapeutic efficacy of CC-1065 analogs can be greatly improved by changing the in vivo distribution through targeted delivery to the tumor site, resulting in lower toxicity to non-targeted tissues, and thus, lower systemic toxicity. In order to achieve this goal, conjugates of analogs and derivatives of CC-1065 with cell-binding agents that specifically target tumor cells have been described {U.S. Pat. Nos. 5,475,092; 5,585,499; 5,846,545}. These conjugates typically display high target-specific cytotoxicity in vitro, and exceptional anti-tumor activity in human tumor xenograft models in mice {R. V. J. Chari et al., Cancer Res., 55, 4079-4084 (1995)}.

Methods for synthesizing CC-1065 analogs that may be used in the cytotoxic conjugates of the present invention, along with methods for conjugating the analogs to cell binding agents such as antibodies, are described in detail in U.S. Pat. Nos. 5,475,092, 5,846,545, 5,585,499, 6,534,660, 6,586,618, 6,756,379, and 7,329,760.

Other Drugs

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs are also suitable for the preparation of conjugates of the present invention. The drug molecules can also be linked to the antibody molecules through an intermediary carrier molecule such as serum albumin. Doxarubicin and Danorubicin compounds, as described, for example, in U.S. Pat. No. 6,630,579, may also be useful cytotoxic agents.

Therapeutic Composition

The present invention also provides a therapeutic composition comprising:

(a) an effective amount of one or more cytotoxic conjugate, and (b) a pharmaceutically acceptable carrier.

Similarly, the present invention provides a method for inhibiting the growth of selected cell populations comprising contacting target cells, or tissue containing target cells, with an effective amount of a cytotoxic conjugate, or therapeutic agent comprising a cytotoxic conjugate, either alone or in combination with other cytotoxic or therapeutic agents.

The present invention also comprises a method for treating a subject having cancer using the therapeutic composition of the present invention.

Cytotoxic conjugates can be evaluated for in vitro potency and specificity by methods previously described (see, e.g., R. V. J. Chari et al, Cancer Res. 55:4079-4084 (1995)). Anti-tumor activity can be evaluated in human tumor xenograft models in mice by methods also previously described (see, e.g., Liu et al, Proc. Natl. Acad. Sci. 93:8618-8623 (1996)).

Suitable pharmaceutically-acceptable carriers are well known and can be determined by those of ordinary skill in the art as the clinical situation warrants. As used herein, carriers include diluents and excipients.

Examples of suitable carriers, diluents and/or excipients include: (1) Dulbecco's phosphate buffered saline, pH ~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20.

The method for inhibiting the growth of selected cell populations can be practiced in vitro, in vivo, or ex vivo. As used herein, inhibiting growth means slowing the growth of a cell, decreasing cell viability, causing the death of a cell, lysing a cell and inducing cell death, whether over a short or long period of time.

Examples of in vitro uses include treatments of autologous bone marrow prior to their transplant into the same patient in order to kill diseased or malignant cells; treatments of bone marrow prior to its transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogeneic bone marrow or tissue prior to transplant in order to prevent graft versus host disease (GVHD). Treatment can be carried out as follows. Bone marrow is harvested from the patient or other individual and then incubated in medium containing serum to which is added the cytotoxic agent of the invention. Concentrations range from about 10 µM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic conjugate of the invention will be supplied as solutions that are tested for sterility and for endotoxin levels. Examples of suitable protocols of cytotoxic conjugate administration are as follows. Conjugates are given weekly for 4 weeks as an i.v. bolus each week. Bolus doses are given in 50 to 100 ml of normal saline to which 5 to 10 ml of human serum albumin can be added. Dosages will be 10 µg to 100 mg per administration, i.v. (range of 100 ng to 1 mg/kg per day). More preferably, dosages will range from 50 µg to 30 mg. Most preferably, dosages will range from 1 mg to 20 mg. After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, cervix and lymphatic organs, osteosarcoma, synovial carcinoma, a sarcoma or a carcinoma in which CA6 is expressed, and other cancers yet to be determined in which CA6 glycotope is expressed predominantly; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

Kit

The present invention also includes kits, e.g., comprising a described cytotoxic conjugate and instructions for the use of the cytotoxic conjugate for killing of particular cell types. The instructions may include directions for using the cytotoxic conjugates in vitro, in vivo or ex vivo.

Typically, the kit will have a compartment containing the cytotoxic conjugate. The cytotoxic conjugate may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the cytotoxic conjugate prior to administering to a patient, and tools that aid in administering the conjugate to a patient.

ADDITIONAL EMBODIMENTS

The present invention further provides for monoclonal antibodies, humanized antibodies and epitope-binding fragments thereof that are further labeled for use in research or diagnostic applications. In preferred embodiments, the label is a radiolabel, a fluorophore, a chromophore, an imaging agent or a metal ion.

A method for diagnosis is also provided in which said labeled antibodies or epitope-binding fragments thereof are administered to a subject suspected of having a cancer, and the distribution of the label within the body of the subject is measured or monitored.

EXAMPLES

The broad scope of this invention is best understood with reference to the following examples, which are not intended to limit the invention to specific embodiments.

Example 1

Identification of Antigen Positive and Negative Cell Lines by Flow Cytometry Binding Assays Flow cytometric analysis was used to localize the DS6 epitope, CA6, to the cell surface. Human cell lines were obtained from the American Type Culture Collection (ATCC) with the exception of OVCAR5 (Kearse et al., *Int. J. Cancer* 88(6):866-872 (2000)), OVCAR8 and IGROV1 cells (M. Seiden, Massachusetts General Hospital). All cells were grown in RPMI 1640 supplemented with 4 mM L-glutamine, 50 U/ml penicillin, 50 µg/ml streptomycin (Cambrex Bio Science, Rockland, Me.) and 10% v/v fetal bovine serum (Atlas Biologicals, Fort Collins, Colo.), referred hereafter as culture media. Cells were maintained in a 37° C., 5% $CO_2$ humidified incubator.

Cells ($1$-$2\times10^{-5}$ cells/well) were incubated, on ice for 3-4 h, with serially diluted concentrations of the DS6 antibody prepared in FACS buffer (2% goat serum, RPMI) into 96-well plates. The cells were spun down in a table top centrifuge at 1500 rpm for 5 min at 4° C. After removing the media, the wells were then refilled with 150 µl of FACS buffer. The wash step was then repeated. FITC-labeled goat anti-mouse IgG (Jackson Immunoresearch) was diluted 1:100 to FACS buffer and incubated with the cells for 1 h on ice. The plate was covered in foil to prevent photobleaching of the signal. After two washes, the cells were fixed with 1% formaldehyde and analyzed on a flow cytometer.

Figure 1:
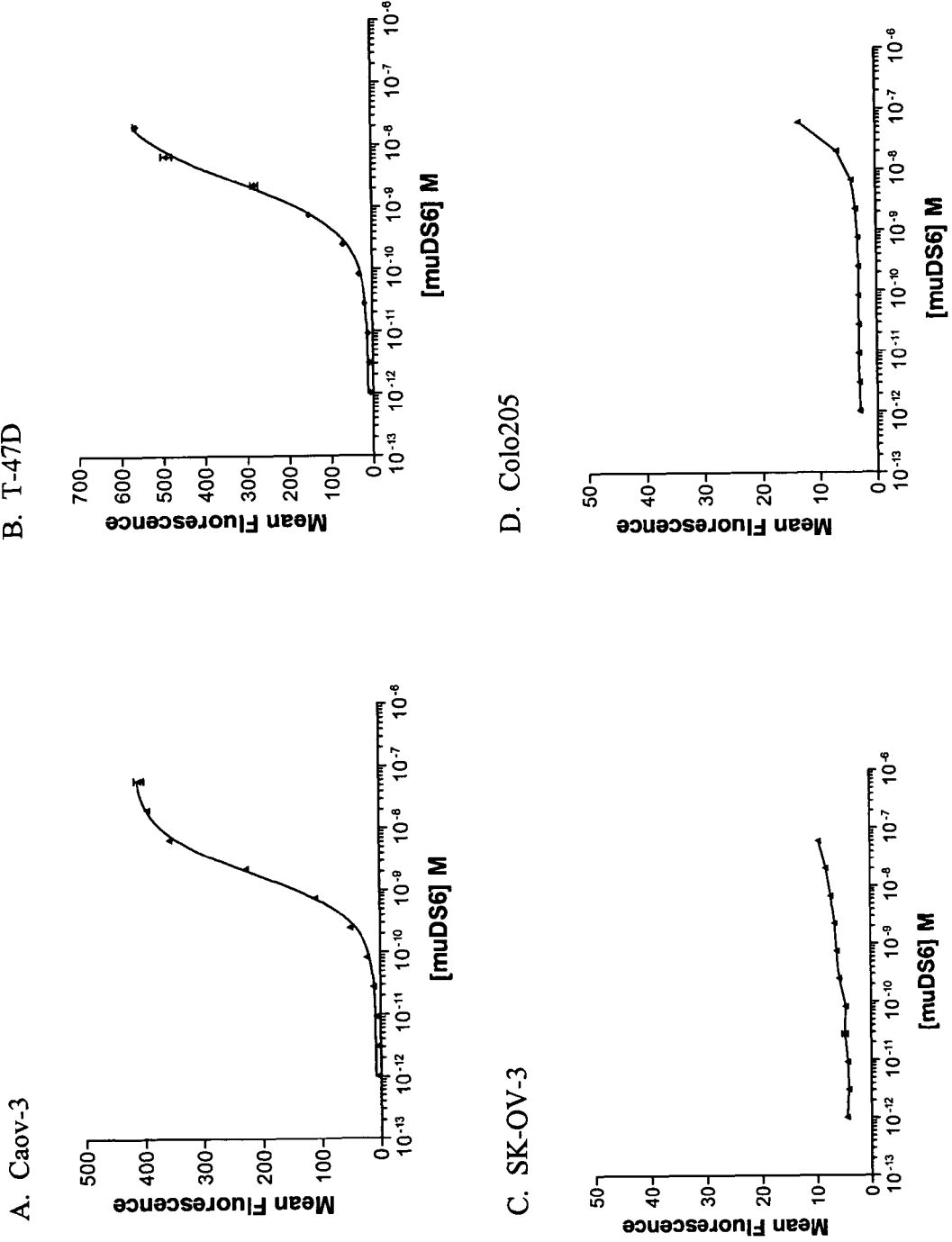
FIG. 1 shows the results of studies performed to determine the ability of the DS6 antibody to bind the surface of selected cancer cell lines. The fluorescence of cell lines incubated with the DS6 primary antibody and FITC conjugated anti-mouse IgG(H+L) secondary antibodies was measured by flow cytometry. The DS6 antibody bound Caov-3 (FIG. 1A) and T-47D (FIG. 1B) cells with an apparent Kd of 1.848 nM and 2.586 nM respectively. Antigen negative cell lines, SK-OV-3 (FIG. 1C) and Colo205 (FIG. 1D) demonstrated no antigen specific binding.

Predominantly, CA6 epitope was found in cell lines of ovarian, breast, cervical, and pancreatic origin (Table 3) as predicted from the tumor immunohistochemistry. However, some cell lines of other tumor types exhibited limited CA6 expression. The DS6 antibody binds with an apparent $K_D$ of 135.6 pM (in PC-3 cells, Table 3). The maximum mean fluorescence (Table 3) of the binding curves (FIG. 1) in the antigen positive cell lines are suggestive of the relative antigen density.

TABLE 3

| Cell Line | Tissue | Antigen | MMF* | Apparent Kd (M) | Cell Line | Tissue | Antigen | MMF* | Apparent Kd(M) |
|---|---|---|---|---|---|---|---|---|---|
| HL-60 | Blood | − | | | Caov-3 | Ovary | + | 465.20 | $5.478 \times 10^{-09}$ |
| Jurkat | Blood | − | | | Caov-4 | Ovary | + | 149.00 | $4.043 \times 10^{-09}$ |
| Namalwa | Blood | − | | | ES-2 | Ovary | − | | |
| U-937 | Blood | − | | | IGROV1 | Ovary | − | | |
| T98G | Brain | + | 35.94 | $1.775 \times 10^{-10}$ | OV-90 | Ovary | − | | |
| BT-20 | Breast | + | 232.20 | $9.142 \times 10^{-10}$ | OVCAR-3 | Ovary | − | | |
| BT-474 | Breast | − | | | OVCAR5 | Ovary | + | 97.10 | $1.473 \times 10^{-09}$ |
| BT-483 | Breast | + | 1911.00 | $1.366 \times 10^{-08}$ | OVCAR8 | Ovary | − | | |
| BT-549 | Breast | + | 71.39 | $1.046 \times 10^{-09}$ | PA-1 | Ovary | − | | |
| CAMA-1 | Breast | + | 12.46 | $2.330 \times 10^{-09}$ | SK-OV-3 | Ovary | − | | |
| MCF-7 | Breast | + | 81.41 | $2.890 \times 10^{-09}$ | SW 626 | Ovary | − | | |
| MDA-MB-157 | Breast | + | 8.635 | $1.972 \times 10^{-10}$ | TOV-112D | Ovary | − | | |
| MDA-MB-231 | Breast | + | 31.85 | $1.460 \times 10^{-09}$ | TOV-21G | Ovary | + | 87.79 | $3.067 \times 10^{-10}$ |
| MDA-MB-468 | Breast | + | 71.58 | $8.127 \times 10^{-10}$ | AsPC-1 | Pancreas | − | | |
| SK-BR-3 | Breast | − | | | BxPC-3 | Pancreas | + | 79.99 | $5.263 \times 10^{-09}$ |

TABLE 3-continued

| Cell Line | Tissue | Antigen | MMF* | Apparent Kd (M) | Cell Line | Tissue | Antigen | MMF* | Apparent Kd(M) |
|---|---|---|---|---|---|---|---|---|---|
| T-47D | Breast | + | 559.58 | $3.424 \times 10^{-09}$ | HPAC | Pancreas | + | 2228.00 | $2.348 \times 10^{-08}$ |
| ZR-75-1 | Breast | + | 811.67 | $4.299 \times 10^{-09}$ | HPAF-II | Pancreas | + | 266.50 | $2.811 \times 10^{-09}$ |
| HeLa | Cervix | + | 242.50 | $6.938 \times 10^{-10}$ | Hs766T | Pancreas | + | 182.90 | $2.319 \times 10^{-09}$ |
| KB | Cervix | + | 119.56 | $1.110 \times 10^{-09}$ | MIAPaCa2 | Pancreas | − | | |
| WISH | Cervix | + | 1133.55 | $2.380 \times 10^{-09}$ | MPanc96 | Pancreas | − | | |
| Colo205 | Colon | − | | | SU.86.86 | Pancreas | + | 36.86 | $1.043 \times 10^{-09}$ |
| DLD-1 | Colon | − | | | SW1990 | Pancreas | + | 36.17 | $3.679 \times 10^{-10}$ |
| HCT-8 | Colon | − | | | PC-3 | Prostate | + | 24.81 | $1.356 \times 10^{-10}$ |
| HT-29 | Colon | − | | | A375 | Skin | − | | |
| Caki-1 | Kidney | − | | | SKMEL28 | Skin | − | | |
| A549 | Lung | − | | | KLE | Uterus | − | | |
| SW2 | Lung | − | | | | | | | |

*average maximum relative mean fluorescence

Example 2

Characterization of DS6 Epitope

The properties of the DS6 antigen, CA6, were analyzed by immunoblotting the dot blots of CA6-positive cell lysates (Caov-3) that were digested with proteolytic (pronase and proteinase K) and/or glycolytic (neuraminidase and periodic acid) treatments. For positive controls, other antibodies recognizing a variety of epitope types were tested on lysates of antigen positive cell lines (Caov-3 and CM1; Colo205 and C242; SKMEL28 and $R_{24}$). CM1 is an antibody recognizing a protein epitope of the variable number tandem repeat domain (VNTR) of Muc-1 and thus, provides a control for a protein epitope. C242 binds to a novel colorectal cancer specific sialic acid-dependent glycotope on Muc-1 (CanAg) which provides a control for a glycotope on a protein. R24 binds to the GD3 ganglioside that is specific for melanoma and thus provides a control for a glycotope on a non-protein scaffold.

Caov-3, Colo205, and SKMEL28 cells were plated in 15 cm tissue culture plates. Culture media (30 mL/plate) was refreshed the day before lysis. A modified RIPA buffer (50 mM Tris-HCl pH 7.6, 150 mM NaCl, 5 mM EDTA, 1% NP40, 0.25% sodium deoxycholate), protease inhibitors (PMSF, Pepstatin A, Leupeptin, and Aprotinin), and PBS were pre-chilled on ice. After the culture media was aspirated from the plates, the cells were washed twice with 10 ml of chilled PBS. All of the subsequent steps were conducted on ice and/or in a 4° C. cold room. After the last wash of PBS was aspirated, the cells were lysed in 1-2 mL of lysis buffer (RIPA buffer with freshly added protease inhibitors to a final concentration of 1 mM PMSF, 1 μM Pepstatin A, 10 μg/ml Leupeptin, and 2 μg/ml Aprotinin). The lysates were scraped off of the plates using a cell lifter and triturated by pipetting the suspensions up and down (5-10 times) with an 18G needle. The lysates were rotated for 10 min and then centrifuged in a microcentrifuge at maximum (13 K rpm) for 10 min. The pellets were discarded and the supernatants were then assayed using a Bradford Protein assay kit (Biorad).

The lysates (2 μl) were pipetted directly onto dry 0.2 μm nitrocellulose membranes. The spots were allowed to air dry for approximately 30 min. The membrane was sectioned into pieces that each contained a single spot. Spots were incubated in the presence of pronase (1 mg/ml enzyme, 50 mM Tris pH 7.5, 5 mM $CaCl_2$), proteinase K (1 mg/ml enzyme, 50 mM Tris pH 7.5, 5 mM $CaCl_2$), neuraminidase (20 mU/ml enzyme, 50 mM sodium acetate pH 5, 5 mM $CaCl_2$, 100 μg/ml BSA) or periodic acid (20 mM, 0.5M sodium acetate pH 5) for 1 h at 37° C. Reagents were purchased from Roche (enzymes) and VWR (periodic acid). Membranes were washed (5 min) in T-TBS wash buffer (0.1% Tween 20, 1×TBS), blocked in blocking buffer (3% BSA, T-TBS) for 2 h at room temperature, and incubated overnight with 2 μg/ml of primary antibody (i.e. DS6, CM1, C242, R24) in blocking buffer at 4° C. The membranes were washed three times for 5 min in T-TBS and then incubated in HRP-conjugated goat anti-mouse (or human) IgG secondary antibody (Jackson Immunoresearch; 1:2000 dilution in blocking buffer) for 1 h at room temperature. The immunoblots were washed three times and developed using an ECL system (Amersham).

The immunoblots (FIG. 2) of the digested control lysates showed that the CM1 signal was destroyed by the proteolytic treatments while the signals of the glycolytic digests were unaffected as would be expected for an antibody recognizing a protein epitope. The C242 signal was destroyed by either the proteolytic or glycolytic treatments as would be expected for an antibody recognizing a glycotope found on a protein. The R24 signal, unaffected by the proteolytic treatments, was abolished with neuraminidase or periodate treatments as expected for an antibody recognizing a ganglioside. The DS6 immunoblot of the digested Caov-3 lysate dot blots showed signal loss upon treatment with either the proteolytic and glycolytic compounds. Thus, like C242, DS6 binds to a carbohydrate epitope on a proteinaceous core. Furthermore, the signal in the DS6 immunoblot was sensitive to neuraminidase treatment. Therefore, CA6, like CanAg, is a sialic acid-dependent glycotope.

Figure 3:
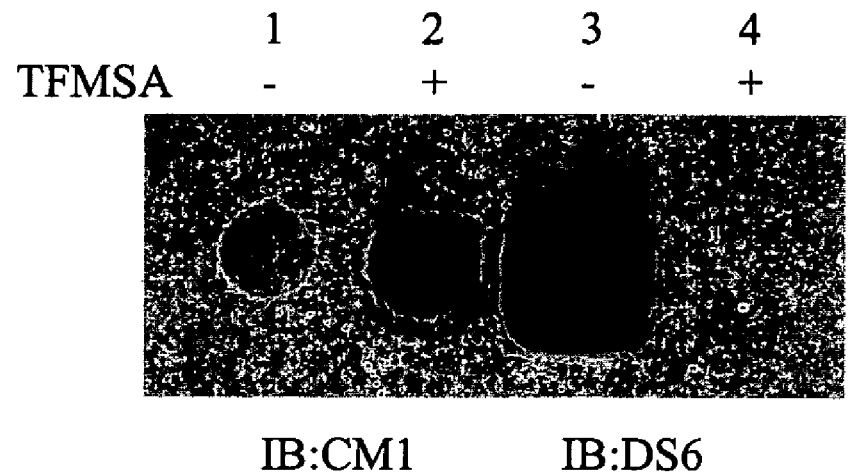
FIG. 3 shows the results of a dot blot analysis of DS6 antigen expression. Caov-3 cell lysates were individually spotted onto PVDF membranes and then incubated in the presence of trifluoromethanesulfonic acid (TFMSA). The membranes were then immunoblotted with the CM1 antibody (1 & 2) or the DS6 antibody (3 & 4).

In order to confirm the carbohydrate nature of CA6, Caov-3 lysate was spotted onto PVDF membrane and treated with the chemical deglycosylating agent, trifluoromethane sulfonic acid (TFMSA), under nitrogen at ambient temperature for 5 minutes. The blot was washed with T-TBS and immunoblotted with either CM1 or DS6 (FIG. 3). The DS6 signal was destroyed upon the acid treatment providing further evidence that CA6 is a glycotope. The enhancement of the CM1 signal upon TFSMA treatment indicates that the acid treatment did not affect the protein on the filter and suggests that the glycolytic treatment unmasked the protein epitope recognized by CM1.

Figure 4:
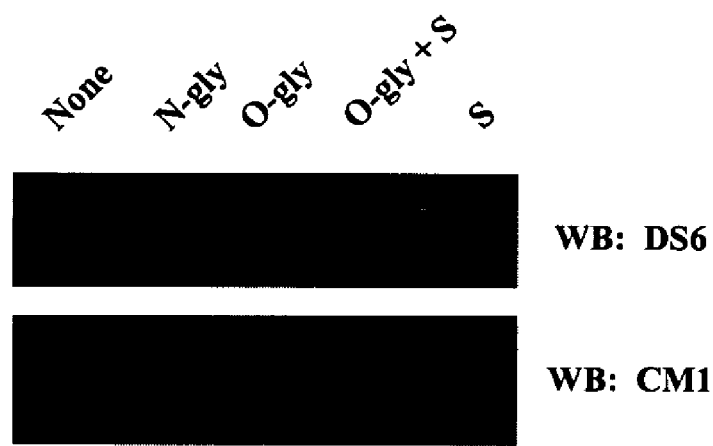
FIG. 4 shows the results of glycotope analysis of the DS6 antigen. Caov-3 lysates pretreated with N-glycanase ("N-gly"), O-glycanase ("O-gly"), and/or sialidase ("S") were spotted onto nitrocellulose and then immunoblotted with the DS6 antibody or the CM1 antibody (Muc-1 VNTR).

To further elucidate the structure of the carbohydrate on which CA6 resides, dot blots were digested with N-glycanase, O-glycanase, and/or sialidase (FIG. 4). Caov-3 cell lysates (100 μg, 30 μl) were incubated at 100° C. for 5 min with 2.5 μl of denaturation buffer (Glyko) containing SDS and β-mercaptoethanol. The denatured lysates were then digested with 1 μl of N-glycanase, O-glycanase, and/or Sialidase A (Glyko) at 37° C. for 1 h. The digested lysates were then spotted (2 µl) onto nitrocellulose and immunoblotted as described above.

N-glycanase had no apparent effect on the DS6 immunoblot signals. However, samples digested with sialidase produced no signal. Because O-glycanase cannot digest sialyated O-linked carbohydrates without pretreatment with sialidase, the DS6 signal of samples processed with O-glycanase alone would not be affected. N-glycanase, in contrast, does not require pretreatment with any glycosidic enzymes for activity. The fact that N-glycanase treatment does not affect the DS6 signal suggests that the CA6 epitope is most likely present on sialyated O-linked carbohydrate chains.

Example 3

Elucidation of the Antigen on which the CA6 Epitope is Found

To identify the antigen on which the CA6 sialoglycotope is found, DS6 immunoprecipitates were analyzed by SDS-PAGE and Western blotting. Cell lysate supernatants (1 mL/sample; 3-5 mg protein) were pre-cleared with Protein G beads (30 µl), equilibrated with 1 ml of RIPA buffer, for 1-2 h, with rotation, at 4° C. All of the subsequent steps were conducted on ice and/or in a 4° C. cold room. The pre-cleared beads were spun down briefly (2-3 s) in a microcentrifuge. The pre-cleared supernatants were transferred to fresh tubes and incubated overnight with 2 µg of DS6, with rotation. Fresh, equilibrated Protein G beads (30 µl) were added to the lysates and incubated for 1 h, with rotation. The bead-lysate suspensions were briefly spun down in a microcentrifuge and samples of the post-immunoprecipitation lysates were optionally taken. The beads were washed 5-10 times with 1 mL of RIPA buffer.

Immunoprecipitated DS6 samples were then digested with 30 µl neuraminidase (20 mU neuraminidase (Roche), 50 mM sodium acetate pH 5, 5 mM $CaCl_2$, 100 µg/ml BSA) or 30 µl periodic acid (20 mM periodic acid (VWR), 0.5M sodium acetate pH 5) for 1 h at 37° C. They were then resuspended in 30 µl of 2× sample loading buffer (containing β-mercaptoethanol). The beads were boiled for 5 min and the loading buffer supernatants were loaded onto 4-12% or 4-20% Tris-Glycine gels (Invitrogen). The gels were run in Laemmli electrophoresis running buffer at 125 V for 1.5 h. The gel samples were transferred, overnight at 20 mA, onto 0.2 µm nitrocellulose membranes (Invitrogen) using a Mini Trans-blot transfer apparatus (Biorad). Membranes were immunoblotted with DS6 as described above in Example 2.

Alternatively, the immunoprecipitated beads were first denatured and then enzymatically digested with N-glycanase, O-glycanase and/or sialidase A (Glyko). The beads were resuspended in 27 µl incubation buffer and 2 µl denaturation solution (Glyko) and incubated at 100° C. for 5 minutes. After cooling to room temperature, detergent solution (2 µl) was added and the samples were incubated with 1 µL of N-glycanase, O-glycanase, and/or Sialidase A at 37° C. for 4 h. After adding 5× sample loading buffer (7 µl), the samples were boiled for 5 min. The samples were subjected to SDS-PAGE and immunoblotted as described above.

DS6 immunoprecipitates a >250 kDa protein band that can be seen in antigen positive cell lysates (FIGS. 5A, B, and C). In some cell lines (i.e. T-47D), a doublet is observed. The >250 kDa band was abolished in Caov-3 immunoprecipitates that were treated with neuraminidase or periodic acid (FIGS. 5A and B) suggesting that the CA6 epitope resides on the >250 kDa band. The >250 kDa band was also shown to be insensitive to N-glycanase treatment of immunoprecipitates consistent with CA6 residing on an O-linked carbohydrate (FIG. 5F). Further supporting that the 250 kDa band is the CA6 antigen is the fact that DS6 immunoprecipitates no such band from DS6 antigen negative cells (FIGS. 5D and E).

Several lines of evidence suggested that the CA6 antigen was Muc1. Because of the high molecular weight and the sensitivity to O-linked carbohydrate-specific glycolytic enzymes, it seemed likely that the CA6 antigen was a mucin. Mucin overexpression is well characterized in tumors particularly of the breast and ovary, consistent with the major tumor reactivities of DS6. Furthermore, CA6, like CanAg (a sialoglycotope on Muc1), is not susceptible to perchloric acid precipitation suggesting the CA6 antigen is heavily O-glycosylated. The observation that in some DS6 expressing cell lines, DS6 immunoprecipitated a doublet of >250 kDa suggested that the CA6 was Muc1. A hallmark of Muc1 in humans is the presence of two distinct Muc1 alleles differing in number of tandem repeats resulting in the expression of two Muc1 proteins of different molecular weights.

To test whether CA6 is found on Muc1, DS6 immunoprecipitates from Caov-3 lysate were subjected to SDS-PAGE and immunoblotted with either DS6 or a Muc1 VNTR antibody, CM1. As can be seen in FIG. 6A, CM1 reacts strongly with the >250 kDa band immunoprecipitated by DS6. In FIG. 6B, DS6 and CM1 immunoprecipitates from HeLa cell lysate show the same >250 kDa doublet when immunoblotted with either DS6 or CM1. These results indicate that the CA6 epitope is indeed located on the Muc-1 protein. The DS6 doublet seen in HeLa (and T-47D) cells can be explained by the fact that Muc-1 expression is directed by distinct alleles having differing number of tandem repeats.

Although CM1 and DS6 bind to the same Muc-1 protein, they are distinct epitopes. Chemical deglycosylation of Caov-3 lysate dot blots by trifluoromethane sulfonic acid (TFMSA) abolished the DS6 signal (FIG. 3). However, this same treatment enhanced the CM1 signal. Deglycosylation may have revealed hidden epitopes for the CM1 antibody. Furthermore, a comparison of the flow cytometry binding results of DS6 and CM1 (Table 4) demonstrates that the CA6 epitope does not exist on every cell expressing Muc1. It is interesting to note that the CA6 epitope is not expressed on Colo205 (Table 3), a cell line known to express high levels of the Muc1 CanAg sialoglycotope.

TABLE 4

| | | DS6 | | CM1 | |
|---|---|---|---|---|---|
| | Cell Line | MMF* | Apparent Kd (M) | MMF* | Apparent Kd (M) |
| DS6 positive & CM1 positive | BT549 | 71.39 | $1.046 \times 10^{-09}$ | 187.90 | $6.056 \times 10^{-09}$ |
| | CaOV3 | 465.20 | $5.478 \times 10^{-09}$ | 1031.00 | $7.479 \times 10^{-09}$ |
| | HeLa | 242.50 | $6.938 \times 10^{-10}$ | 334.80 | $2.907 \times 10^{-09}$ |
| | KB | 119.56 | $1.110 \times 10^{-09}$ | 338.00 | $5.345 \times 10^{-09}$ |
| | MCF7 | 81.41 | $2.890 \times 10^{-09}$ | 1023.00 | $8.694 \times 10^{-09}$ |

TABLE 4-continued

|  | Cell Line | DS6 MMF* | DS6 Apparent Kd (M) | CM1 MMF* | CM1 Apparent Kd (M) |
|---|---|---|---|---|---|
| DS6 negative & CM1 positive | KLE | 27.48 | — | 561.70 | $8.156 \times 10^{-09}$ |
|  | OVCAR3 | 21.19 | — | 192.50 | $5.949 \times 10^{-09}$ |
|  | SKOV3 | 17.53 | — | 49.41 | $6.246 \times 10^{-09}$ |

*MMF = maximum mean relative fluorescence

Example 4

Quantitative Analysis of Shed CA6 Epitope

Because the CA6 epitope resides on Muc1, a molecule known to be shed into the blood stream in many cancer patients, a quantitative approach was undertaken in order to determine whether such levels would be prohibitive for DS6 antibody therapy. Binding of circulating antibody to antigen is thought to lead to rapid clearance of immune complexes from the blood. If a significant portion of the administered antibody dose is rapidly removed from circulation the amount reaching the tumor is likely to be diminished resulting in decreased anti-tumor activity of an antibody therapeutic. When the antibody is conjugated to a highly potent cytotoxic compound the rapid clearance of conjugate could potentially increase non-specific toxicity. Thus, in the case of antibody-small drug conjugates such as DS6-DM1, high levels of shed antigen might be expected to both reduce the anti-tumor effect and increase the dose-limiting toxicity.

Recent clinical trials of antibody therapeutics have yielded information as to the impact of shed antigen concentration on pharmacokinetics. For example, in clinical trials with trastuzumab (Herceptin), an antibody used for the treatment of her2/neu-expressing metastatic breast cancer, the pharmacokinetics of trastuzumab clearance was shown to be unaltered when the shed Her2/neu level was less than 500 ng/mL (Pegram et al., *J. Clin. Oncol.* 16(8):2659-71 (1998). Assuming a molecular weight of shed Her2/neu of 110,000 Daltons, a molar concentration shed Her2/neu below 4.5 nM appears to have little influence on the pharmacokinetics.

In another example, a clinical trial with cantuzumab mertansine (huC242-DM1) indicated that there was no correlation with pretreatment shed CanAg (C242 epitope) levels and pharmacokinetics of antibody clearance (Tolcher et al., *J. Clin. Oncol.* 21(2):211-22 (2003). The CanAg epitope, similar to the CA6 epitope recognized by DS6, is a unique tumor-specific O-linked sialoglycotope on Muc1. However, the heterogeneous nature of the CanAg epitope makes it difficult to quantify in molar terms. In the general population Muc1 alleles vary in length depending upon the number of tandem repeats in the variable number tandem repeat (VNTR) domain. Several sites for O-linked glycosylation occur in each tandem repeat. Adding to the complexity of CanAg expression is the cell-to-cell variation in inherent glycosyl transferase activity. Thus a wide range of CanAg epitopes per Muc1 molecule are possible even in a single patient. Moreover, the ratio of CanAg epitope per Muc1 molecule will be different across a population of patients. For this reason, shed CanAg in serum samples is measured by sandwich ELISA where shed Muc1 with CanAg epitope is captured by C242 and detected by a biotinylated C242/Streptavidin HRP system. The shed CanAg is quantified in standardized units (U) proportional to the number of epitopes per ml of serum rather than by a molar concentration of Muc1. By analogy, a similar situation occurs for the quantification of shed CA6 epitopes. In contrast, for trastuzumab there is only one epitope per shed her2/neu molecule vastly simplifying the quantification of shed antigen.

In order to relate CA6 shed epitope levels to those found in clinical trials with trastuzumab and cantuzumab mertansine, a method for obtaining molar concentrations of complex shed epitopes such as sialoglycotopes on Muc1 was developed. First, a simple sandwich ELISA assay for DS6 was established. A representation of the assay is shown in FIG. 7A. DS6 was used to capture Muc1 having CA6 epitope. Because each Muc1 molecule has multiple CA6 epitopes, biotinylated DS6 was also used as the tracer antibody. Biotinylated DS6 bound to captured CA6 was detected by Streptavidin-HRP using ABTS as the substrate. CA6 epitope was captured from ovarian cancer patient serum or from standards which come from a commercially available Muc1 test kit (CA15-3) used to monitor shed Muc1 in breast cancer patients. DS6 units/ml were arbitrarily set equal to CA15-3 standards units/ml.

In FIG. 7B is shown the results of the DS6 sandwich ELISA in which CA15-3 standards were used. The curve generated is very similar to that obtained with CA15-3 standards in the CA15-3 assay. In order to convert DS6 unit/ml to a molar concentration of CA6 a standard curve for biotinylated DS6 which converts signal to picograms of DS6 is required. Assuming a one-to-one stoichiometry between CA6 epitope and biotinylated DS6 antibody and a molecular weight of 160,000 Daltons for biotinylated DS6 the moles of CA6 captured per volume of sample added can be computed.

In FIGS. 8A and B are representations of two alternative means of generating a standard curve for biotinylated DS6. In FIG. 8A, Goat anti-mouse IgG polyclonal antibody is used to capture biotinylated DS6 which is in turn detected in a manner identical to that used in the sandwich ELISA assay shown in FIG. 7. In the method shown in FIG. 8B biotinylated DS6 is plated directly onto the ELISA plate and detected as in FIG. 8A. As seen in FIG. 8C the biotinylated DS6 standard curves generated by each method are in good agreement.

In Table 5 the analysis of ovarian cancer patient serum samples for various shed antigens is shown. CA125 ELISA is generally used to monitor the treatment of ovarian cancer patients by measuring shed CA125 units/ml. The CA125 status was provided with the serum samples. CA15-3 ELISA is generally used to monitor the treatment of breast cancer patients by measuring the units/ml of shed Muc1 using capture and detections antibodies recognizing epitopes distinct from that recognized by DS6. In Table 5, CA15-3 is measured in ovarian cancer patients serum samples.

TABLE 5

| Serum No. | CA125[1] (U/ml) | CA15-3[1] (U/ml) | DS6[2] (U/ml) | DS6[3] (pM) | DS6[4] (pM) |
|---|---|---|---|---|---|
| 4 | 72.80 | 117.72 | 29.79 | 52.13 | 188.94 |
| 5 | 3651.90 | 98.19 | 567.02 | 654.44 | >2560.00 |
| 6 | 930.50 | 87.08 | 504.15 | 667.56 | 2505.00 |
| 7 | 76.00 | 72.70 | 135.65 | 246.94 | 778.25 |
| 8 | 32.50 | 18.44 | 39.96 | 65.19 | 239.88 |
| 9 | 551.70 | 292.39 | >975.61 | 1512.31 | >2560.00 |
| 10 | 90.00 | 42.40 | 49.48 | 85.19 | 305.88 |
| 11 | 200.50 | 60.58 | 92.32 | 152.38 | 526.75 |
| 12 | 283.00 | 35.67 | 83.65 | 135.81 | 485.06 |
| 13 | 197.50 | 20.61 | 35.92 | 61.06 | 216.25 |
| 14 | 100.60 | 6.13 | 12.39 | 23.19 | 88.06 |
| 15 | 34.60 | 59.18 | 199.85 | 286.63 | 1228.56 |
| 17 | 196.40 | 56.75 | 66.53 | 130.44 | 405.88 |
| 18 | 16.90 | 30.45 | 34.43 | 60.81 | 223.69 |
| 19 | 22.00 | 263.93 | 118.98 | 191.69 | 728.94 |
| 22 | 110.70 | 21.44 | 16.46 | 29.94 | 111.38 |

[1]determined by commercial ELISA kit
[2]determined by commercial CA15-3 standards (1 CA15-3 U = 1 DS6 U)
[3]goat anti-mouse IgG & biotin-DS6 standard curve
[4]biotin-DS6 standard curve For the CA15-3 values reported in Table 5, a commercially available CA15-3 Enzyme Immuno Assay kit from CanAg Diagnostics was used. For the DS6 units/ml a standard curve was generated using the CA15-3 standards (from the CA15-3 Enzyme Immuno Assay kit from CanAg Diagnostics) in the DS6 sandwich ELISA. DS6 units/ml were arbitrarily set equal to CA15-3 units/ml. In the last two columns picomolar (pM) shed CA6 was calculated using the biotinylated DS6 standard curves shown in FIG. 8C.

For the quantitative analysis of CanAg levels, CanAg serum levels were those reported for patients participating in a cantuzumab mertansine clinical trial prior to treatment (Tolcher et al., *J. Clin. Oncol.* 21(2):211-22 (2003). An ELISA assay analogous to the one described for DS6 was used to make a CanAg standard curve using CanAg standards. C242 was used to capture the CanAg standards. Detection of captured CanAg was achieved using biotinylated C242 tracer followed by development with streptavidin-HRP using ABTS as substrate. A biotinylated-C242 standard curve was constructed as done for biotinylated DS6 allowing for the conversion of units/ml to a molar concentration of circulating CanAg epitopes. In Table 6 CanAg levels from cantuzumab mertansine clinical trial patients are reported along with the corresponding calculated molar concentrations of circulating CanAg.

TABLE 6

| CanAg[1] (U/ml) | CanAg[2] (pM) | CanAg[3] (pM) |
|---|---|---|
| 31240 | 19185.7 | 34592.8 |
| 8687 | 3535 | 9619.3 |
| 7456 | 4579 | 8256.2 |
| 3686 | 2263.7 | 4081.6 |
| 1447 | 888.7 | 1602.3 |
| 1262 | 775 | 1397.4 |
| 718 | 441 | 795.1 |
| 547 | 335.9 | 605.7 |
| 394 | 242 | 436.3 |
| 381 | 234 | 421.9 |
| 329 | 202.1 | 364.3 |
| 322 | 197.8 | 356.6 |
| 306 | 187 | 338.8 |
| 284 | 174.4 | 314.5 |
| 247 | 151.7 | 273.5 |
| 242 | 148.6 | 268 |
| 229 | 140.6 | 253.6 |
| 227 | 139.4 | 251.4 |
| 184 | 113 | 203.7 |
| 120 | 73.7 | 132.9 |
| 107 | 65.7 | 118.5 |
| 100 | 61.4 | 110.7 |
| 81 | 49.7 | 89.7 |
| 81 | 49.7 | 89.7 |
| 67 | 41.1 | 74.2 |
| 53 | 32.5 | 58.7 |
| 45 | 27.6 | 49.8 |
| 43 | 26.4 | 47.6 |
| 39 | 24 | 43.2 |
| 36 | 22.1 | 39.9 |
| 24 | 14.7 | 26.6 |
| 18 | 11.1 | 19.9 |
| 17 | 10.4 | 18.8 |
| <10 | 6.1 | 11.3 |
| <10 | 6.1 | 11.3 |
| <10 | 6.1 | 11.3 |
| <10 | 6.1 | 11.3 |

[1]pretreatment levels of circulating CanAg measured by sandwich ELISA
[2]goat anti-mouse IgG & biotin-C242 standard curve
[3]biotin-C242 standard curve A comparison of the pM levels of shed CA6 in ovarian cancer patients with those calculated for shed CanAg in CanAg-positive cancer patients shows that in general shed CA6 levels are similar to shed CanAg levels. Furthermore, only 2 out of 16 ovarian cancer patients serum samples potentially have CA6 levels greater than 4.5 nM, (serum samples 5 and 9 for which the signal was out of the range of the standard curve), the level above which altered herceptin pharmacokinetics was observed in clinical trials with Her2/neu-positive breast cancer patients. CanAg levels above 4.5 nM were only seen in 3 out of 37 clinical trial patients. In this clinical trial there was no correlation with shed CanAg levels and more rapid clearance of cantuzumab mertansine. However, the patient with the highest CanAg level (31240 U/ml) was only sampled for 8 hours post-transfusion. These results indicate that certain epitopes of Muc1, such as CA6 and CanAg, while shed in cancer patients, are not shed at levels prohibitive for antibody therapeutic treatment.

Example 6

Cloning Murine DS6 Antibody Variable Regions

Murine monoclonal antibodies such as DS6 have limited utility in a clinical setting because they are recognized as foreign by the human immune system. Patients quickly develop human anti-mouse antibodies (HAMA) resulting in rapid clearance of murine antibodies. For this reason, the variable region of murine DS6 (muDS6) was resurfaced to produce humanized DS6 (huDS6) antibodies.

The murine DS6 antibody variable regions were cloned by RT-PCR. Total RNA was purified from a confluent T175 flask of DS6 hybridoma cells using the Qiagen RNeasy miniprep kit. RNA concentrations were determined by UV spectrophotometry and RT reactions were done with 4-5 μg total RNA using the Gibco Superscript II kit and random hexamer primers.

PCR reactions were performed with degenerate primers based on those described in Wang Z et al., *J Immunol Methods.* January 13; 233(1-2):167-77 (2000). The RT reaction mix was used directly for degenerate PCR reactions. The 3' light chain primer, HindKL, (TATAGAGCTCAAGCTTGGATGGTGGGAA-GATGGATACAGTTGGTGC)

(SEQ ID NO:25)

and 3' heavy chain primer, BamIgG1, (GGAGGATCCATAGACAGATGGGGGT-GTCGTTTTGGC) (SEQ ID NO:26)

were used, and for the 5' end PCR primers were Sac1MK (GGGAGCTCGAYATTGTGMTSACMCARWCTMCA) (SEQ ID NO:27) for the light chain and an equal mix of EcoR1MH1 (CTTCCGGAATTCSARGTNMAGCTGSAGSAGTC) (SEQ ID NO:28) and EcoR1MH2 (CTTCCGGAATTC-SARGTNMAGCTGSAGSAGTCWGG) (SEQ ID NO:29) for the heavy chain (mixed bases: H=A+T+C, S=G+C, Y=C+T, K=G+T, M=A+C, R=A+G, W=A+T, V=A+C+G, N=A+T+G+C).

PCR reactions were standard except they were supplemented with 10% DMSO (50 μl reaction mixes contained final concentrations of 1× reaction buffer (ROCHE), 2 mM each dNTP, 1 mM each primer, 2 μl RT reaction, 5 μl DMSO, and 0.5 μl Taq (ROCHE)). The PCR reactions were performed on an MJ research thermocycler using a program adapted from Wang Z et al., (*J Immunol Methods.* January 13; 233(1-2):167-77 (2000)): 1) 94° C., 3 min; 2) 94° C., 15 sec; 3) 45° C., 1 min; 4) 72° C., 2 min; 5) cycle back to step #2 29 times; 6) finish with a final extension step at 72° C. for 10 min. The PCR products were cloned into pBluescript II SK+ (Stratagene) using restriction enzymes created by the PCR primers. Seqwright sequencing services sequenced the heavy and light chain clones.

In order to confirm the 5' end cDNA sequences, additional PCR and cloning was done. The DS6 light chain and heavy chain cDNA sequences, determined from the degenerate PCR clones, were plugged into the NCBI's Blast search website and murine antibody sequences with signal sequence submitted were saved. PCR primers were designed from these signal peptides using conserved stretches among the related DNA sequences. EcoRI restriction sites were added to the leader sequence primers (Table 7) and these were used in RT-PCR reactions as described above.

Several individual light and heavy chain clones were sequenced to identify and avoid possible polymerase generated sequence errors. Only a single sequence was obtained for both the light chain and heavy chain RT-PCR clones. These sequences were sufficient to design primers that could amplify the murine DS6 light and heavy chain sequences extending into the signal sequence. The subsequent clones from these follow-up PCR reactions confirmed the 5' end sequences of the variable region that had been altered by the original degenerate primers. The cumulative results from the various cDNA clones provided the final murine DS6 light and heavy chain sequences presented in FIG. 9. Using Kabat and AbM definitions, the three light chain and heavy chain CDRs were identified (FIGS. 9 and 10). A search of the NCBI IgBlast database indicates that the muDS6 antibody light chain variable region most likely derives from the murine IgVκ ap4 germline gene while the heavy chain variable region most likely derives from the murine IgVh J558.41 germline gene (FIG. 11).

Example 7

Determination of the Variable Region Surface Residues of DS6 Antibody

The antibody resurfacing techniques described by Pedersen et al. (1994) and Roguska et al. (1996) begin by predicting the surface residues of the murine antibody variable sequences. A surface residue is defined as an amino acid that has at least 30% of its total surface area accessible to a water molecule. In the absence of a solved structure to find the surface residues for muDS6, we aligned the ten antibodies with the most homologous sequences in the set of 127 antibody structure files (FIG. 12). The solvent accessibility for each Kabat position was averaged for these aligned sequences (FIGS. 13A and B).

Surface positions with average accessibilities of between 25% and 35% were subjected to a second round of analysis by comparing a subset of antibodies containing two identical residues flanking on either side (FIGS. 13A and B). After the second round analysis, the 21 predicted surface residues for the muDS6 heavy chain were increased to 23, adding Tyr3 and Lys23 to the list of residues with predicted surface accessibility greater than 30%. In most of our resurfaced antibodies the Kabat definition of the heavy chain CDR1 is used, but for DS6 the AbM definition was inadvertently used during the calculations so the heavy chain residue T28 was not defined as a framework surface residue as it might otherwise have been. The number of light chain surface positions was reduced from 16 to 15 because the predicted surface accessibility of Ala80 was reduced from 30.5% to 27.8% in the second round analy-

TABLE 7

DS6 Signal Sequence Degenerate Primers

| Name | Sequence | |
|---|---|---|
| Heavy Chain - DS6HClead | ttttgaattcaataactacaggtgtccact | - SEQ ID NO: 30 |
| Light Chain - KTILClead | ttttgagctccagattttcagcttcctgct | - SEQ ID NO: 31 | sis. Together, the muDS6 heavy and light chain variable sequences have 38 predicted surface accessible framework residues.

Example 8

Human Antibody Selection

The surface positions of the murine DS6 variable region were compared to the corresponding positions in human antibody sequences in the Kabat database (Johnson G, Wu T T. *Nucleic Acids Res. January* 1; 29(1):205-6 (2001)). The antibody database management software SR (Searle, 1998) was used to extract and align the surface residues from natural heavy and light chain human antibody pairs. The human antibody variable region surface with the most identical surface residues, with special consideration given to positions that come within 5 Å of a CDR, was chosen to replace the murine DS6 antibody variable region surface residues.

Example 9

Expression Vector for Chimeric and Humanized Antibodies

Figure 14:
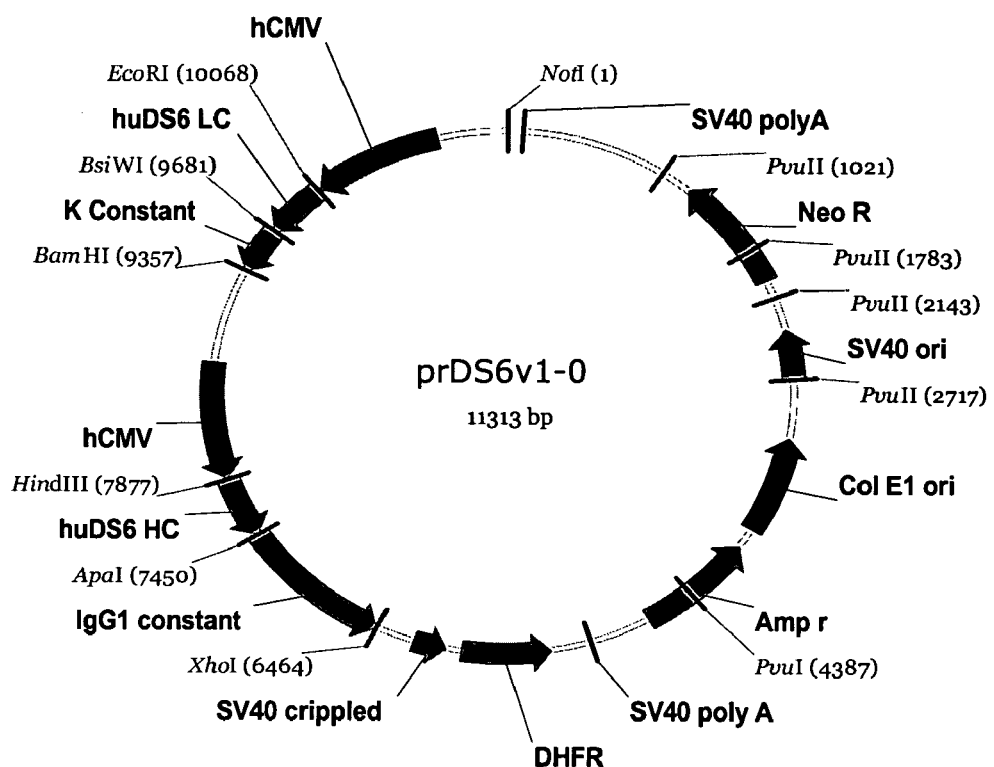
FIG. 14 shows the prDS6 v1-0 mammalian expression plasmid map. This plasmid was used to build and express the recombinant chimeric and humanized DS6 antibodies.

The light and heavy chain paired sequences were cloned into a single mammalian expression vector. The PCR primers for the human variable sequences created restriction sites that allowed the human signal sequence to be added in the pBluescriptII cloning vector. The variable sequences could then be cloned into the mammalian expression plasmid with EcoRI and BsiWI or HindIII and ApaI for the light chain or heavy chain respectively (FIG. 14). The light chain variable sequences were cloned in-frame onto the human IgKappa constant region and the heavy chain variable sequences were cloned into the human IgGamma1 constant region sequence. In the final expression plasmids, human CMV promoters drive the expression of both the light and heavy chain cDNA sequences.

Example 10

Identification of Residues that may Negatively Affect DS6 Activity

In most of the humanizations to date a molecular model of the subject antibody has been built to identify residues proximal to a CDR as potential problem residues. With an expanding number of resurfaced antibodies to work from, historical experience is at least as effective at predicting problems as building a model, so no molecular model was built for DS6. Instead, the murine DS6 surface residues were compared with those of previously resurfaced antibodies and residues with low to high risk for affecting the antibody's binding activity were identified.

Similar sets of residues are repeatedly identified as being within 5 Å of a CDR in both the available solved antibody structures and the molecular models from previous humanizations. Using this data, Table 1 gives the murine DS6 residues that are likely proximal to and possibly within 5 Å of a CDR. Many of these positions have also been changed in previous humanizations, but only heavy chain position 74 has ever resulted in a loss of binding activity. The murine residue was retained in this position in both huC242 and huB4 in order to conserve the binding activity of the murine antibody. On the other hand, this same position was changed to the corresponding human residue in humanized 6.2G5C6 without loss of activity (6.2G5C6 is the anti-IGF1-R antibody often referred to simply as anti-C6). While any of the residues in Table 1 could present a problem in the humanized antibody, the heavy chain residue P73 will be of particular concern due to previous experiences in this position.

Example 11

Selection of the Most Homologous Human Surface

Candidate human antibody surfaces for resurfacing muDS6 were pulled from the Kabat antibody sequence database using SR software. This software provides an interface to search only specified residue positions against the antibody database. To preserve the natural pairs, the surface residues of both the light and heavy chains were compared together. The most homologous human surfaces from the Kabat database were aligned in order of rank of sequence identity. The top 3 surfaces as aligned by the SR Kabat database software are given in Table 2. The surfaces were then compared to identify which human surfaces would require the least changes to the residues identified in Table 1. The anti-Rh(D) antibody, 28E4 (Boucher et al, 1997), requires the least number of surface residue changes (11 total) and only 3 of these residues are included in the list of potential problem residues. Since the 28E4 antibody provides the most homologous human surface, it is the best candidate to resurface muDS6.

Example 12

Construction of the DNA Sequences for Humanized DS6 Antibodies

The 11 surface residue changes for DS6 were made using PCR mutagenesis. PCR mutagenesis was performed on the murine DS6 variable region cDNA clones to build the resurfaced, human DS6 gene. Humanization primer sets were designed to make the amino acid changes required for resurfaced DS6, shown below in Table 8.

TABLE 8

| Primer Name | Primer Sequence | |
|---|---|---|
| DS6HCapa | cgatgggcccttggtggaggctgcagagacagtgaccaga | SEQ ID NO: 32 |
| DS6LCBsi | ttttcgtacgtttcagctccagcttggt | SEQ ID NO: 33 |
| DS6HC5end | caggtgtacactcccaggcttatctccagcagtct | SEQ ID NO: 34 |
| huC6HCApa | cgatgggcccttggtggaggcggcagagacagtgaccaga | SEQ ID NO: 35 |
| ds61c5et | caggtgtacactccgagattgttctcacccagtctccagcaacc atgtctgcatct | SEQ ID NO: 36 |

TABLE 8-continued

| Primer Name | Primer Sequence | | |
|---|---|---|---|
| ds6LCr18 | ggcactgcaggttatggtgaccctctccctggaga | SEQ ID NO: | 37 |
| ds61cs77f | caatcagcagcatggaggctgaaga | SEQ ID NO: | 38 |
| ds61cs77r | gcctccatgctgctgattgtgaga | SEQ ID NO: | 39 |
| DS6HCvvkp | caggtgtacactcccaggctcagctcgtgcagtctggggctgag gtggtgaagcccggggcctcagt | SEQ ID NO: | 40 |
| DS6HCt | ttgactgcagacacatcctccagcaca | SEQ ID NO: | 41 |
| ds6hcQT | gtgtctgcagtcaatgtggccttgccctggaacttctgat | SEQ ID NO: | 42 |
| huDS6HCapa | cgatgggcccttggtggaggcggcagagacagtgacaaga | SEQ ID NO: | 43 |

PCR reactions were standard except they were supplemented with 10% DMSO (50 µl reaction mixes contained final concentrations of 1× reaction buffer (ROCHE), 2 mM each dNTP, 1 mM each primer, 100 ng template, 5 µl DMSO, and 0.5 µl Taq (ROCHE)). They were run on an MJ Research thermocycler with the following program: 1) 94° C., 1 min; 2) 94° C., 15 sec; 3) 55° C., 1 min; 4) 72° C., 1 min; 5) cycle back to step #2 29 times; 6) finish with a final extension step at 72° C. for 4 min. The PCR products were digested with their corresponding restriction enzymes and cloned into the pBluescript cloning vectors. Clones were sequenced to confirm the amino acid changes.

Since changing heavy chain residue P73 has caused problems in the past, two versions of the heavy chain were built, one with the human 28E4 T73 and one retaining the murine P73. The other 10 surface residue were changed from murine to the human 28E4 residue in both versions of humanized DS6 (Table 2). Sticking with the usual naming method, the most human is version 1.0 since it has all 11 human surface residues. The heavy chain version retaining the murine P73 is named version 1.2 in case further versions are required so version 1.1 is reserved for a version containing the maximum number of murine residues. The amino acid sequences of the two humanized versions are shown aligned with the murine DS6 amino acid sequence in FIGS. 15A and B. Both of the humanized DS6 antibody genes were cloned into the antibody expression plasmid (FIG. 14) for transient and stable transfections. The cDNA and amino acid sequences of the humanized versions 1.01 and 1.21 are light chain variable region are the same and shown in FIG. 16. The heavy chain cDNA and amino acid sequences of the humanized versions 1.01 and 1.21 are shown in FIGS. 17A and B.

Example 13

Expression and Purification of huDS6 in CHO Cells and Affinity Measurements

To determine whether the humanized DS6 versions retained the binding affinity of muDS6 it was necessary to express and purify the antibodies. CHO cells were stably transfected with a chimeric version of DS6 (chDS6) having the human constant region and the murine variable region, or with huDS6v1.01 or huDS6v1.21.

CHODG44 cells ($4.32 \times 10^6$ cells/plate) were seeded in 15 cm plates in non-selective media (Alpha MEM+nucleotides (Gibco), supplemented with 4 mM L-glutamine, 50 U/ml penicillin, 50 µg/ml streptomycin, and 10% v/v FBS) and placed in a 37° C., 5% $CO_2$ humidified incubator. The following day, the cells were transfected with the chDS6 expression plasmid using a modified version of the Qiagen recommended protocol for Polyfect Transfection. The non-selective media was aspirated from the cells. The plates were washed with 7 ml of pre-warmed (37° C.) PBS and replenished with 20 ml of non-selective media. The plasmid DNA (11 µg) was diluted into 800 µl of Hybridoma SFM (Gibco). Then, 70 µl of Polyfect (Qiagen) was added to the DNA/SFM mixture. The Polyfect mixture was then gently vortexed for several seconds and incubated for 10 min at ambient temperature. Non-selective media (2.7 ml) was added to the mixture. This final mixture was incubated with the plated cells for 24 h.

The transfection mixture/media was removed from the plates and the cells were then trypsinized and counted. The cells were then plated in selective media (Alpha MEM-nucleotides, supplemented with 4 mM L-glutamine, 50 U/ml penicillin, 50 µg/ml streptomycin, 10% v/v FBS, 1.25 mg/ml G418) in 96 well plates (250 µl/well) at various densities (1800, 600, 200, and 67 cells/well). The cells were incubated for 2-3 weeks, supplementing media if necessary. Wells were screened for antibody production levels using a quantitative ELISA. An Immulon 2HB 96 well plate was coated with goat anti-human IgG F(ab)$_2$ antibody (Jackson Immunoresearch; 1 µg/well in 100 µl 50 mM sodium carbonate buffer pH 9.6) and incubated for 1.5 h at ambient temperature, with rocking. All subsequent steps were conducted at ambient temperature. The wells were washed twice with T-TBS (0.1% Tween-20, TBS) and blocked with 200 µl of blocking buffer (1% BSA, T-TBS) for 1 h. The wells were washed twice with T-TBS. In a separate plate, the antibody standard, EM164 (100 ng/ml), and culture supernatants were serially diluted (1:2 or 1:3) in blocking buffer. These dilutions (100 µl) were transferred to the ELISA plate and incubated for 1 h. The wells were washed 3 times with T-TBS and incubated with 100 µl of goat anti-human IgG Fc-AP (Jackson ImmunoResearch) diluted 1:3000 in blocking buffer for 45 min. After 5 washes with T-TBS, the wells were developed using 100 µl of PNPP development reagent (10 mg/ml PNPP (p-Nitrophenyl Phosphate, Disodium Salt; Pierce), 0.1 M diethanolamine pH 10.3 buffer) for 25 min. The absorbance at 405 µm was measured in an ELISA plate reader. Absorbance readings (of the culture supernatant) in the linear portion of the standard curve were used to determine the antibody levels.

The highest producing clones, identified by the ELISA, were then subcloned, expanded, and frozen cell stocks were prepared.

For expression of huDS6v1.01 and huDS6v1.21, DG44 CHO cells (Dr. Lawrence Chasin, Columbia University, NY) were cultured in Alpha MEM with ribonucleosides and deoxyribonucleosides (Gibco catalog #12571, Grand Island, N.Y.). The medium was supplemented with 10% fetal bovine serum (HyClone catalog # SH30071.03, Logan, Utah), 1% gentamicin (Mediatech catalog# 30-005-CR, Herndon, Va.), and 2 mM L-glutamine (L-glut) (BioWhittaker catalog#17-605E, Walkersville, Md.). This formulation was termed CHO Complete Medium.

DG44 CHO cells ($5\times10^6$) were transfected with 50 μg of huDS6 plasmid DNA. Prior to transfection, cells were removed from flasks with trypsin (Gibco catalog # 15090-046, Grand Island, N.Y.) and washed two times with unsupplemented Alpha MEM lacking ribonucleosides and deoxyribonucleosides (Gibco catalog #12561, Grand Island, N.Y.). This was termed Wash Medium. Cells were mixed with plasmid DNA in 0.4 cm gap electrode cuvettes (BioRad catalog # 1652088, Hercules, Pa.). They were placed on ice for two minutes, and then pulsed at 1,000 μF and 260 volts in a BioRad electroporation apparatus. Following electroporation, cells were incubated on ice for two minutes. The cells were then plated in five 24 well plates (Costar catalog #3524) in CHO Complete Medium and were maintained in a 37° C. incubator with 5% $CO_2$. After 48 hours, the medium was removed from the wells. Wells were rinsed once with Wash Medium and fed with Alpha MEM without ribonucleosides and deoxyribonucleosides (Gibco catalog #12561, Grand Island, N.Y.) supplemented with 1% gentamicin, 2 mM L-glut, 10% dialyzed fetal bovine serum (Gibco catalog # 26400-044, Grand Island, N.Y.), and 1.25 mg/mL geneticin (G418) (Gibco catalog # 11811, Grand Island, N.Y.). This complete formulation was termed Selection Medium. Clones were incubated in Selection Medium for approximately two weeks at which time they were screened for antibody production by Quantitative ELISA. The highest producing clones were then subcloned, expanded, and frozen cell stocks were prepared.

To produce sufficient amount of antibody to purify, cells were expanded onto 15 cm plates (~$1\times10^6$ cells/plate) with 30 ml of selective media supplemented with Ultra Low IgG FBS (Gibco) and incubated for 1 week. Culture supernatants were collected into 250 ml conical tubes, spun down in a tabletop centrifuge (2000 rpm, 5 min, 4° C.), and then sterile-filtered through a 0.2 μm filter apparatus.

For purification of DS6, pellets of NaOH were added to the filtered culture supernatants to a final pH of 8.0. A Hi Trap rProtein A column (Amersham) was equilibrated with 20-50 column volumes of binding buffer. The supernatant was loaded onto the column using a peristaltic pump. Then, the column was washed with 50 column volumes of binding buffer. The bound antibody was eluted off of the column using elution buffer (100 mM acetic acid, 50 mM NaCl, pH 3) into tubes set in a fraction collector. The eluted antibody was neutralized using neutralization buffer (2 M $K_2HPO_4$, pH 10.0) and dialyzed overnight in PBS. The dialyzed antibody was filtered through a 0.2 μm syringe filter. The absorbance at 280 nm was measured to determine the final protein concentration.

Figure 18:
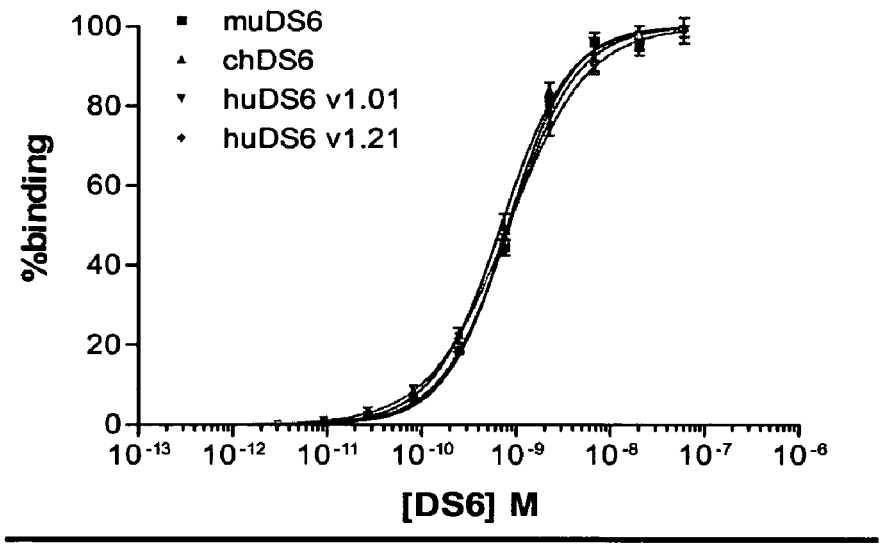
FIG. 18 shows flow cytometry binding curves of murine DS6 (muDS6) chimeric DS6 (chDS6), and human DS6 version 1.01 (huDS6 v1.01) and version huDS6 version 1.21 (huDS6 v1.21) from an assay performed on KB cells. The avidities of the murine, chimeric, and human v1.01 and v1.21 DS6 antibodies (muDS6=0.82 nM, chDS6=0.69 nM, huDS6v1.01=0.82 nM and huDS6v1.21=0.85 nM) are comparable, indicating that resurfacing has not diminished the avidity.
Figure 19:
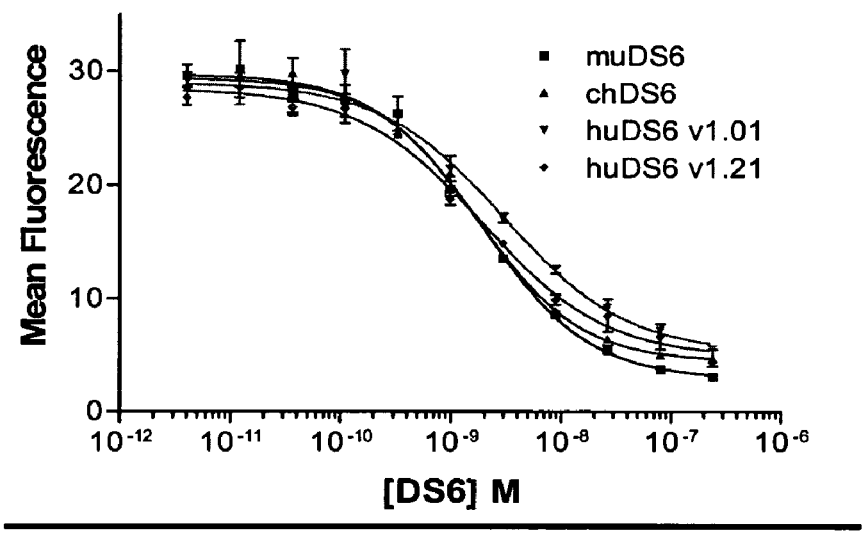
FIG. 19 shows the results of a competition binding assay of muDS6, chDS6, huDS6 v1.01 and huDS6 v1.21 antibodies with biotinylated muDS6. Varying concentrations of naked muDS6, chDS6, huDS6v1.01 and huDS6v1.21 were combined with 2 nM of biotin-muDS6 and the streptavidin-DTAF secondary. The IC50's (muDS6=1.9 nM, chDS6=1.7 nM, huDS6v1.01=3.0 nM, and huDS6v1.21=1.9 nM) of all antibodies are similar indicating that humanization has not reduced the avidity.

The affinity of the purified huIgG was compared with muDS6 by flow cytometry. In the first set of experiments direct binding to a CA6-expressing cell line, KB, was measured. As shown in FIG. 18 the muDS6, chDS6, huDS6v1.01 and huDS6 v1.21 show very similar affinities with apparent Kds of 0.82 nM, 0.69 nM, 0.82 and 0.85 nM, respectively, suggesting that resurfacing has not disrupted the CDRs. To confirm that the huDS6 versions retain the affinity of muDS6, competitive binding experiments were conducted. The advantage of this format is that the same detection system is used for both murine and human antibodies; that is biotin-muDS6/streptavidin-DTAF. The results of the competition binding assay comparing the ability of muDS6, chDS6, huDS6v1.01 and huDS6v1.21 to compete with biotin-DS6 is shown in FIG. 19. The apparent $EC_{50}$ are 1.9 nM, 1.7 nM, 3.0 and 1.9 nM for muDS6, chDS6, huDS6 v1.01, and huDS6 v1.21, respectively. These results indicate that resurfacing of muDS6 to produce a humanized DS6 causes little reduction in binding affinity.

Example 14

Preparation of muDS6-DM1 Cytotoxic Conjugate

Figure 20:
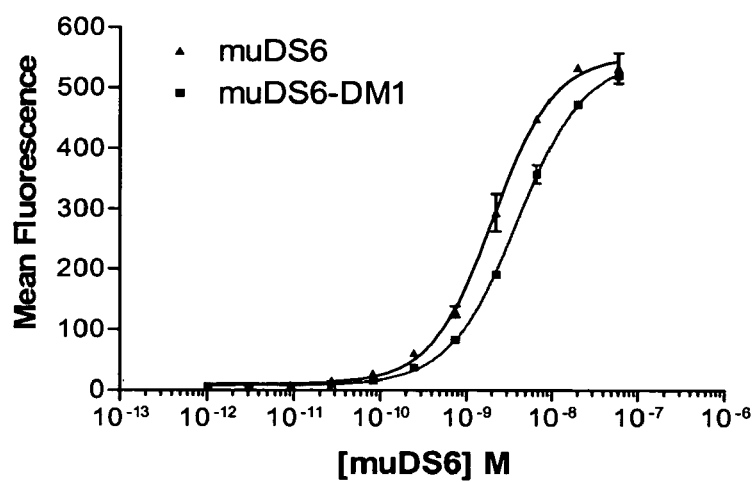
FIG. 20 shows the results of a determination of the binding affinity of un-conjugated DS6 antibody versus a DS6 antibody-DM1 conjugate. The results demonstrated that DM1 conjugation does not adversely affect the binding affinity of the antibody. The apparent Kd of the DS6 antibody-DM1 conjugate (3.902 nM) ("DS6-DM1") was slightly greater than the naked antibody (2.020 nM) ("DS6").

The muDS6 antibody (8 mg/ml) was modified using 8-fold molar excess of N-succinimidyl-4-(2-pyridyldithio)pentanoate (SPP) to introduce dithiopyridyl groups. The reaction was carried out in 95% v/v Buffer A (50 mM KPi, 50 mM NaCl, 2 mM EDTA, pH 6.5) and 5% v/v DMA for 2 h at room temperature. The slightly turgid reaction mixture was gel-filtered through a NAP or Sephadex G25 column (equilibrated in Buffer A). The degree of modification was determined by measuring the absorbance of the antibody at 280 nm and the DTT released 2-mercaptopyridine (Spy) at 280 and 343 nm. Modified muDS6 was then conjugated at 2.5 mg Ab/mL using a 1.7-fold molar excess of $N^{2'}$-deacetyl-$N$-$^{2'}$(3-mercapto-1-oxopropyl)-maytansine (L-DM1) over SPy. The reaction was carried out in Buffer A (97% v/v) with DMA (3% v/v). The reaction was incubated at room temperature overnight for ~20 h. The opaque reaction mixture was centrifuged (1162×g, 10 min) and the supernatant was then gel-filtered through a NAP-25 or S300 (Tandem 3, 3×26/10 desalting columns, G25 medium) column equilibrated in Buffer B (1×PBS pH 6.5). The pellet was discarded. The conjugate was sterile-filtered using a 0.22 μm Millex-GV filter and was dialyzed in Buffer B with a Slide-A-Lyzer. The number of DM1 molecules linked per molecule of muDS6 was determined by measuring the absorbance at both 252 nm and 280 nm of the filtered material. The DM1/Ab ratio was found to be 4.36 and the step yield of conjugated MUDS6 was 55%. The conjugated antibody concentration was 1.32 mg/mL. The purified conjugate was biochemically characterized by size exclusion chromography (SEC) and found to be 92% monomer. Analysis of DM1 in the purified conjugated indicated that 99% was covalently bound to antibody. In FIG. 20, flow cytometric binding of the muDS6-DM1 conjugate and unmodified muDS6 to Caov-3 cells shows that conjugation of muDS6 results in only a slight loss of affinity.

Example 15

In Vitro Cytotoxicity of muDS6-DM1

As a naked antibody, muDS6 has shown no proliferative or growth inhibitive activity in cell cultures (FIG. 21) However, when muDS6 is incubated with cells in the presence of a DM1 conjugate to Goat anti-mouse IgG heavy and light chain, muDS6 is very effective at targeting and delivering this conjugate to the cell resulting in indirect cytotoxicity (FIG. 21). To further test the inherent activity of naked muDS6, a complement-dependent cytotoxicity (CDC) assay using muDS6 was conducted. HPAC and ZR-75-1 cells (25000 cells/well) were plated in 96 well plates, in the presence of 5% human or rabbit serum and various dilutions of muDS6, in 200 μl of RHBP media (RPMI-1640, 0.1% BSA, 20 mM HEPES (pH 7.2-7.4), 100 U/ml penicillin and 100 ug/ml streptomycin). The cells were incubated for 2 h at 37° C. Then Alamar Blue (10% of final concentration) reagent (Biosource) was added to the supernatant. The cells were incubated for 5-24 hrs before measuring fluorescence. Murine DS6 had no effect in a complement-dependent cytotoxicity (CDC) assay (FIG. 22) This suggests that the therapeutic application of muDS6 would require the conjugation of a toxic effector molecule.

The cytotoxicity of maytansinoid conjugated muDS6 antibody was examined using 2 different assay formats in various DS6 positive cell lines. Clonogenic assays were conducted where cells (1000-2500 cells/well) were plated on 6-well plates in 2 ml of conjugate diluted in culture media. The cells were continuously exposed to the conjugate at several concentrations, generally between $3 \times 10^{-11}$ M to $3 \times 10^{-9}$ M, and were incubated in a 37° C., 6% $CO_2$ humidified chamber for 5-9 days. The wells were washed with PBS and the colonies were stained with a 1% w/v crystal violet/10% v/v formaldehyde/PBS solution. Unbound stain was then washed thoroughly from the wells with distilled water, and the plates were allowed to dry. The colonies were counted using a Leica StereoZoom 4 dissecting microscope.

Plating efficiency (PE) was calculated as the number of colonies/number of cells plated. Surviving fraction was calculated as PE of treated cells/PE of non-treated cells. The $IC_{50}$ concentration was determined by graphing the surviving fraction of cells vs. the molar concentration of the conjugate. In a clonogenic assay (FIG. 23), muDS6-DM1 was effective in killing Caov-3 cells with an estimated $IC_{50}$ of 800 pM. Antigen negative cells, A375, were only slightly affected by the conjugate at a concentration of $3 \times 10^{-9}$ M, the highest concentration of muDS6-DM1 tested, demonstrating that the cell killing activity of the conjugate is directed specifically toward antigen-expressing cells. However, despite apparent sensitivity to maytansine, many of the other DS6 positive cell lines were not particularly sensitive to the immunoconjugate. All of the cervical cell lines (HeLa, KB, and WISH) were sensitive to the conjugate whereas only a select number of the ovarian and breast cell lines showed any cytotoxic affects. None of the pancreatic cell lines appeared to have been affected.

In the MTT assay, cells were seeded in 96-well plates at a density of 1000-5000 cells/well. The cells were plated with serial dilutions of either naked muDS6 or muDS6-DM1 immunoconjugate in 200 µl of culture media. The samples were run in triplicate. The cells and antibody/conjugate mixtures were then incubated for 2-7 d, at which time cell viability was assessed by an MTT ([3(4,5-dimethylthiazol-2-yl)-2, 5-diphenyl tetrazolium bromide)] assay. MTT (50 µg/well) was added to the culture supernatant and allowed to incubate for 3-4 h at 37° C. The media was removed and the MTT formazan was solubilized in DMSO (175 µl/well). The absorbance at 540-545 nm was measured. In a MTT cell viability assay (FIG. 24C), the immunoconjugate was able to effectively kill Caov-3 cells with an estimated $IC_{50}$ of 1.61 nM. The wells with the highest concentrations of conjugate contained no viable cells as compared to naked antibody which had no effect (FIGS. 21 and 24).

The results of the MTT assays on the other cell lines were slightly different (FIGS. 24A, B, and D-I). In many cases, although some cytotoxicity was seen, the conjugate was unable to completely kill the entire cell population (with the exception of WISH cells). BT-20, OVCAR5, and HPAC cells were particularly resistant: in the highest conjugate concentration (32 nM) wells, over 50% of the cells were still viable.

Example 16

In Vivo Conjugate Anti-Tumor Activity

To demonstrate the in vivo activity of the muDS6-DM1 conjugate, human tumor xenografts were established in SCID mice. A subcutaneous model of the human cervical carcinoma cell-line, KB, was developed. KB cells were grown in vitro, collected, and $5 \times 10^6$ cells in a 100 µL of serum free medium were injected under the right shoulder of each mouse and allowed to grow for 6 days to an average tumor volume of $144 \pm 125$ mm$^3$ at which time drug treatment was initiated. Mice were given either PBS, conjugate at 150 µg/kg DM1, or conjugate at 225 µg/kg DM1 (2 mice per group) intravenously every day for 5 days. Toxic responses were monitored daily during the treatment. Tumor volumes (FIG. 25A) and corresponding body weights (FIG. 25B) were monitored throughout the study.

The KB tumors treated with PBS control grew rapidly with a doubling time of about 4 days. In contrast, both groups of mice treated with conjugate exhibit complete tumor regression 14 days and 18 days after treatment initiation for the 225 µg/kg and 150 µg/kg dose groups, respectively. At the 150 µg/kg dose the tumor delay was approximately 70 days. Treatment at 225 µg/kg resulted in cures as there was no evidence of tumor recurrence at the termination of the study on day 120. As seen in FIG. 25B the mice in the 150 µg/kg group showed no weight loss indicating that the dose was well tolerated. At the higher dose the mice experience only a temporary 3% reduction in body weight. During the 5-day treatment course, mice exhibited no visible signs of toxicity. Taken together, this study demonstrates that muDS6-DM1 treatment can cure mice of KB xenograft tumors at a non-toxic dose.

muDS6-DM1 activity was further tested on a panel of subcutaneous xenograft models (see FIG. 26). The tumor cell-lines used to make xenografts displayed a range of in vitro maytansine sensitivities and CA6 epitope densities (Table 9 below). OVCAR5 cells and TOV-21G are ovarian tumor cell lines; HPAC is a pancreatic tumor cell line; HeLa is a cervical tumor cell line. OVCAR5 and TOV-21G cells have low surface CA6 expression; HeLa cells have an intermediate level of surface CA6 expression; HPAC cells have a high CA6 density of surface expression. TOV-21G and HPAC cells are maytansine sensitive; OVCAR5 and HeLa cells are 2-7-fold less maytansine sensitive.

TABLE 9

| Cell Line | MMF* | Apparent Kd (M) | Clonogenic Assay Maytansine $IC_{50}$ (M) | Clonogenic Assay Conjugate $IC_{50}$ (M) | MTT Assay Conjugate $EC_{50}$ (M) |
|---|---|---|---|---|---|
| BT-20 | 232.20 | $9.14 \times 10^{-10}$ | $3.50 \times 10^{-10}$ | $>3.00 \times 10^{-09}$ | $1.44 \times 10^{-08}$ |
| BT-483 | 1911.00 | $1.37 \times 10^{-08}$ | $1.50 \times 10^{-10}$ | $1.00 \times 10^{-10}$ | N/A |
| Caov-3 | 465.20 | $5.48 \times 10^{-09}$ | $3.20 \times 10^{-11}$ | $8.00 \times 10^{-10}$ | $1.61 \times 10^{-09}$ |
| Caov-4 | 149.00 | $4.04 \times 10^{-09}$ | $6.00 \times 10^{-10}$ | $>3.00 \times 10^{-09}$ | N/A |
| HeLa | 242.50 | $6.94 \times 10^{-10}$ | $1.00 \times 10^{-10}$ | $1.80 \times 10^{-09}$ | N/A |
| HPAC | 2228.00 | $2.35 \times 10^{-08}$ | $5.50 \times 10^{-11}$ | $1.80 \times 10^{-09}$ | $1.84 \times 10^{-09}$ |
| HPAF-II | 266.50 | $2.81 \times 10^{-09}$ | $6.00 \times 10^{-10}$ | $>3.00 \times 10^{-09}$ | $1.00 \times 10^{-08}$ |
| Hs766T | 182.90 | $2.32 \times 10^{-09}$ | $>3.00 \times 10^{-09}$ | $>3.00 \times 10^{-09}$ | $>3.20 \times 10^{-08}$ |

TABLE 9-continued

| Cell Line | MMF* | Apparent Kd (M) | Clonogenic Assay Maytansine IC$_{50}$ (M) | Clonogenic Assay Conjugate IC$_{50}$ (M) | MTT Assay Conjugate EC$_{50}$ (M) |
|---|---|---|---|---|---|
| KB | 119.56 | $1.11 \times 10^{-10}$ | $3.00 \times 10^{-11}$ | $1.40 \times 10^{-09}$ | $3.01 \times 10^{-09}$ |
| OVCAR5 | 97.10 | $1.47 \times 10^{-09}$ | $3.20 \times 10^{-10}$ | $>3.00 \times 10^{-09}$ | $8.46 \times 10^{-07}$ |
| T-47D | 559.58 | $3.42 \times 10^{-09}$ | $1.20 \times 10^{-10}$ | $>3.00 \times 10^{-09}$ | N/A |
| TOV-21G | 87.79 | $3.07 \times 10^{-09}$ | $4.80 \times 10^{-11}$ | $2.00 \times 10^{-09}$ | $6.88 \times 10^{-09}$ |
| WISH | 1133.55 | $2.38 \times 10^{-09}$ | $9.00 \times 10^{-11}$ | $4.60 \times 10^{-10}$ | $6.69 \times 10^{-10}$ |
| ZR-75-1 | 811.67 | $4.30 \times 10^{-09}$ | $1.00 \times 10^{-10}$ | N/A | $9.45 \times 10^{-10}$ |

*average maximum relative mean fluorescence

The 4 cell-lines were grown in vitro, collected, and $1 \times 10^7$ cells in a 100 µL of serum free medium were injected under the right shoulder of each mouse (6 mice per model) and allowed to grow for 6 days to an average tumor volume of 57.6±6.7 and 90.2±13.4 mm$^3$ for the test and control groups respectively of OVCAR5, 147.1±29.6 and 176.2±18.9 mm$^3$ for the test and control groups respectively of HPAC, 194.3±37.2 and 201.7±71.7 mm$^3$ for the test and control groups respectively of HeLa, and 96.6±22.8 and 155.6±13.4 mm$^3$ for the test and control groups respectively of TOV-21G, at which time drug treatment was initiated. For each model three control mice were treated with two weekly doses of PBS and three test mice were treated with two weekly doses of conjugate (600 µg/kg DM1) intravenously. Toxic responses were monitored daily during the treatment and tumor volumes and body weights were monitored throughout the study. The conjugate efficacy for the various models is shown graphically in FIGS. 26A, C, E, and G and the corresponding body weights are plotted in FIGS. 26B, D, F, and H. OVCAR5, TOV-21G, and HPAC cell-lines form aggressive tumors as can be seen in the PBS controls for each model. The HeLa model had about a 3 week lag period before beginning exponential growth. In all models, DS6-DM1 conjugate treatment resulted in a complete tumor regression in all mice. For the TOV-21G, HPAC, and HeLa models the mice remain tumor-free at day 61. In the OVCAR5 model tumors recurred at about day 45 after tumor inoculation. Thus, muDS6-DM1 treatment in this model results in a tumor growth delay of approximately 34 days. The growth delay is significant as OVCAR5 cells are less maytansine-sensitive and have low CA6 epitope expression. In models where either the CA6 epitope density is higher or the model has greater maytansine sensitivity, the tumor regression is more robust. It is important to note that only 2 doses were administered. Clearly the dosing schedule used in this study was not toxic to the mice as no weight loss was observed. It is likely that cures could be achieved with additional or higher conjugate doses.

Human ovarian cancer is largely a disease of the peritoneum. OVCAR5 cells grow aggressively as an intraperitoneal (IP) model in SCID mice forming tumor nodules and producing ascites in a manner similar to human disease. To demonstrate activity in an IP model, muDS6-DM1 was used to treat mice bearing OVCAR5 IP tumors (FIG. 27). OVCAR5 cells were grown in vitro, harvested and $1 \times 10^7$ cells in 100 µL of serum free medium were injected intraperitoneally. Tumors were allowed to grow for 6 days at which time treatment was initiated. Mice were treated weekly for 2 weeks with either PBS or DS6-DM1 conjugate at a dose of 600 µg/kg DM1 and monitored for weight loss resulting from peritoneal disease. By day 28, the PBS group of mice had lost greater than 20% body weight and were euthanized. The treated group was sacrificed at day 45 after exceeding 20% body weight loss. This study demonstrates that muDS6-DM1 is able to delay tumor growth in the aggressive OVCAR5 IP model despite the fact that OVCAR5 cells are less sensitive to maytansine and have few CA6 epitopes per cell. Because the dosing schedule used elicited no visible signs of toxicity, it is likely that additional and higher doses could be used to achieve further tumor growth delay or cures.

Example 17

Synthesis and Characterization of DS6-SPP-MM1-202 Taxoid Cytotoxic Conjugate muDS6 was modified with the N-sulfosuccinimidyl 4-nitro-2-pyridyl-pentanoate (SSNPP) linker. To 50 mg of muDS6 Ab in 90% Buffer A, 10% DMA was added 10 equivalents of SSNPP in DMA. The final concentration of Ab was 8 mg/ml. The reaction was stirred for 4 hours at room temperature, then purified by G25 chromatography. The extent of antibody modification was measured spectophotometrically using the absorbance at 280 nm (antibody) and 325 (linker) and found to have 3.82 linkers/antibody. Recovery of the antibody was 43.3 mg giving an 87% yield. Conjugation of muDS6-nitroSPP was conjugated with Taxoid MM1-202 (1812 P.16). Conjugation was carried out on a 42 mg scale in 90% Buffer A, 10% DM1. The taxoid was added in 4 aliquots of 0.43 eq/Linker (each aliquot) over a period of about 20 hours. By this time the reaction had turned noticeably cloudy. After G25 purification the resulting conjugate, recovered in about 64% yield had about 4.3 taxoids/Ab and about 1 equivalent of unreacted linker left. To quench unreacted linker, 1 equivalent of cysteine/unreacted linker was added to the conjugate with stirring overnight. A definite yellowish tinge was noticeable upon cysteine addition indicating release of thiopyridine. The reaction solution was then dialyzed in Buffer B/0.01% Tween 20 followed by further dialysis in Buffer B alone over several days. The final conjugate had 2.86 drugs/antibody. The antibody recovery was 14.7 mg, giving a 35% yield overall. Conjugate was further biochemically characterized by SEC and found to have 89% monomer, 10.5% dimer and 0.5% higher molecular weight aggregate.

The results of a flow cytometry analysis comparing the binding of muDS6-SPP-MM1-202 taxoid versus muDS6 antibody on HeLa cells is shown in FIG. 28. The results indicate that muDS6 retains binding activity when conjugated to a taxane.

Example 18

In Vitro and In Vivo Activity of Humanized DS6 Conjugate

A huDS6v1.01-SPDB-DM4 conjugate was constructed. This conjugate is similar to the muDS6-SPP-DM1 conjugate described in Example 14 except that the linker/maytansine drug part of the conjugate differs in the structure around the disulfide bond; the muDS6-SPP-DM1 conjugate has one methyl group hindrance on the disulfide carbon on the antibody side of the linker while the SPDB-DM4 conjugate has two methyl group hindrance on the disulfide carbon on the maytansine side of the linker.

The huDS6v1.01 antibody (8 mg/ml) was modified using 8-fold molar excess of N-succinimidyl-4-(2-pyridyldithio) butanoate (SPDB) to introduce dithiopyridyl groups. The reaction was carried out in 95% v/v Buffer A (50 mM KPi, 50 mM NaCl, 2 mM EDTA, pH 6.5) and 5% v/v ethanol for 1.5 h at room temperature. The reaction mixture was gel-filtered through a 15 ml Sephadex G25 column (equilibrated in Buffer A). The degree of modification was determined by measuring the absorbance of the antibody at 280 nm and the DTT released 2-mercaptopyridine (Spy) at 280 and 343 nm. Modified DS6 was then conjugated at 1.8 mg Ab/mL using a 1.7-fold molar excess of $N^{2'}$-deacetyl-N-$^{2'}$(4-methyl-4-mercapto-1-oxopentyl)-maytansine (L-DM4) over SPy. The reaction was carried out in Buffer A (97% v/v) with DMA (3% v/v). The reaction was incubated at room temperature overnight for ~20 h. In contrast to the conjugation of muDS6, the reaction mixture was clear and immediately underwent gel-filtration through a NAP15 ml G25 column equilibrated in Citrate buffer (20 mM citrate, 135 mM NaCl, pH 5.5). The conjugate was sterile-filtered using a 0.22 µm Millex-GV filter. The number of DM4 molecules linked per molecule of DS6 was determined by measuring the absorbance at both 252 nm and 280 nm of the filtered material. The DM4/Ab ratio was found to be 3.2 and the step yield of conjugated DS6 was 69%. The conjugated antibody concentration was 1.51 mg/mL. The purified conjugate was biochemically characterized by size exclusion chromotography (SEC) and found to be 92.5% monomer. Analysis of DM4 in the purified conjugated indicated that >99% was covalently bound to antibody.

In FIG. 29A, flow cytometric binding of the huDS6v1.01-DM4 conjugate and unmodified DS6 to KB cells shows that conjugation of huDS6v1.01 results in essentially no loss of affinity. The binding was conducted essentially as described for FIG. 20 except that KB cells were used rather than CaOv-3 cells. In vitro cytotoxicity of huDS6v1.01 was tested essentially as described in FIG. 24G. huDS6v1.01 killed WISH cells with an $IC_{50}$ of $4.4 \times 10^{-10}$ M whereas unconjugated huDS6v1.01 showed no cytotoxic activity.

The in vivo activity of huDS6v1.01-DM4 was tested on the HPAC pancreatic model. HPAC cells were inoculated on day 0, and immunoconjugate treatments were given on day 13. PBS control animals were euthanized once tumor volumes exceeded 1000 mm³. The conjugate was given at a dose of either 200 µg/kg or 600 µg/kg DM4, corresponding to an antibody concentration 15 mg/kg and 45 mg/kg, respectively. Tumor volume (FIG. 30A) and body weight (FIG. 30B) of the mice were monitored during the course of the study. The huDS6v1.01-DM4 showed potent anti-tumor activity at 200 µg/kg DM4 with all mice achieving complete tumor regression. The control B4-DM4 conjugate recognizing an antigen not expressed on HPAC xenografts had essentially no activity at 200 µg/kg. The lack of body weight loss (FIG. 30B) of the mice indicates that the treatment with 200 µg/kg conjugate is below the maximum tolerated dose. This result demonstrates that a humanized version of DS6 is able to mediate targeted delivery of a maytansinoid drug resulting in potent anti-tumor activity.

What is claimed is:

1. An antibody or fragment thereof comprising at least one heavy chain variable region and at least one light chain variable region, wherein said heavy chain variable region comprises the amino acid sequence selected from the group consisting of SEQ ID NO:10 and SEQ ID NO:11, and wherein said light chain variable region comprises three complementary determining regions comprising the amino acid sequences of SEQ ID NOS:4-6.

2. The antibody or fragment thereof of claim 1, wherein said heavy chain variable region consists of the amino acid sequence of SEQ ID NO:10 or SEQ ID NO:11, and wherein said light chain variable region comprises three complementary determining regions comprising the amino acid sequences of SEQ ID NOS:4-6.

3. The antibody or fragment thereof of claim 1, wherein said light chain variable region comprises the amino acid sequence of SEQ ID NO:8.

4. The antibody or fragment thereof of claim 1, wherein said heavy chain variable region comprises the amino acid sequence of SEQ ID NO:10 or SEQ ID NO:11, and wherein said light chain variable region consists of the amino acid sequence of SEQ ID NO:8.

5. A humanized antibody or fragment thereof, produced by a method of resurfacing comprising:

(a) generating position alignments from relative accessibility distributions from x-ray crystallographic structures of a pool of rodent and human antibody heavy and light chain variable regions to yield a set of heavy and light chain variable region framework surface exposed positions, wherein the alignment positions for all rodent and human variable regions are at least about 98% identical;

(b) defining for a rodent antibody or epitope-binding fragment thereof a set of heavy and light chain variable region framework surface exposed amino acid residues using said set of heavy and light chain variable region framework surface exposed positions generated in said step (a);

(c) identifying from human antibody amino acid sequences a set of heavy and light chain variable region framework surface exposed amino acid residues that is most closely identical to said set of rodent surface exposed amino acid residues defined in said step (b);

(d) substituting, in the variable region framework amino acid sequence of said rodent antibody or epitope-binding fragment thereof, said set of heavy and light chain variable region framework surface exposed amino acid residues defined in said step (b) with said set of heavy and light chain variable region framework surface exposed amino acid residues identified in said step (c);

(e) constructing three-dimensional models of said variable region of said rodent antibody or epitope-binding fragment thereof and of said variable region of said rodent antibody or epitope-binding fragment thereof resulting from the substituting specified in said step (d);

(f) comparing said three-dimensional models constructed in said step (e), and identifying any amino acid residues from said sets identified in said steps (b) or (c), that are within 5 Å of any atom of any residue of the complementarity determining regions of said rodent antibody or epitope-binding fragment thereof;

(g) changing any residues identified in said step (f) from the human to the original rodent amino acid residue to thereby define a humanizing set of surface exposed amino acid residues;

(h) replacing the set of rodent antibody variable region framework surface exposed amino acid residues defined in said step (b) with the humanizing set of variable region framework surface exposed amino acid residues defined in said step (g); and (i) producing said humanized rodent antibody or epitope-binding fragment thereof that binds to the CA6 glycotope, wherein said light chain variable region comprises the amino acid sequence of SEQ ID NO:8 and wherein said heavy chain variable region comprises an amino acid sequence selected from the group consisting of SEQ ID NO:10 and SEQ ID NO:11.

6. The humanized antibody or fragment thereof of claim 5, wherein said humanized rodent antibody or said fragment thereof specifically binds muc 1.

7. The humanized antibody or fragment thereof of claim 6, wherein said fragment is selected from the group consisting of a Fab fragment, a Fab' fragment, a F(ab')₂ fragment, a Fd fragment, a single-chain Fvs (scFv) fragment, a single-chain antibody and a disulfide-linked Fvs (sdFv).

8. The humanized antibody or fragment thereof of claim 5 or 6, wherein said surface exposed amino acid residues are those residues whose solvent accessibility is above 30%.

9. The humanized antibody or fragment thereof of claim 5, wherein said antibody or fragment thereof is a conjugate.

10. The humanized antibody or fragment thereof of claim 5, consisting of a light chain variable region having the amino acid sequence of SEQ ID NO:8.

11. The humanized antibody or fragment thereof of claim 5, consisting of a heavy chain variable region having an amino acid sequence selected from the group consisting of SEQ ID NO:10 and SEQ ID NO:11.

12. A humanized antibody or a fragment thereof that specifically binds to muc 1, comprising at least one heavy chain variable region and at least one light chain variable region, wherein said heavy chain variable region comprises three complementarity-determining regions comprising the amino acid sequences of SEQ ID NOS: 1-3, and wherein said light chain variable region comprises the amino acid sequence of SEQ ID NO:8, wherein said antibody or fragment thereof is a conjugate.

13. A humanized antibody or a fragment thereof that specifically binds to muc 1, comprising at least one heavy chain variable region and at least one light chain variable region, wherein said light chain variable region comprises three complementarity-determining regions comprising the amino acid sequences of SEQ ID NOS: 4-6, and wherein said heavy chain variable region comprises the amino acid sequence selected from the group consisting of SEQ ID NO:10 and SEQ ID NO:11.

14. A humanized antibody or a fragment thereof, comprising at least one heavy chain variable region and at least one light chain variable region, wherein said heavy chain variable region comprises three complementarity-determining regions comprising the amino acid sequences of SEQ ID NOS: 20-22, and wherein said light chain variable region comprises three complementarity-determining regions comprising the amino acid sequences of SEQ ID NOS: 4-6.

15. The humanized antibody or a fragment thereof of claim 14, wherein said fragment consists essentially of at least one heavy chain variable region, wherein said heavy chain variable region has three complementarity-determining regions consisting of the amino acid sequences of SEQ ID NOS: 20-22.

16. The antibody or fragment thereof of claim 1, 3, 4 or 14, which is produced in bacteria.

17. The antibody or fragment thereof of claim 3, 4 or 14, which is produced in CHO cells.

18. A composition comprising the antibody or fragment thereof of claim 1, 3, 4 or 14, conjugated to a detectable label.

19. The antibody or fragment thereof of claim 1, 3, 4 or 14, wherein said antibody or fragment thereof specifically binds to the CA6 glycotope in a Western blot.

20. The antibody or fragment thereof of claim 1, 3, 4 or 14, wherein said antibody or fragment thereof specifically binds to the CA6 glycotope in an ELISA.

21. The antibody or fragment thereof of claim 1, 3, 4 or 14, wherein said antibody or fragment thereof is a conjugate.

* * * * *

UNITED STATES PATENT AND TRADEMARK OFFICE
CERTIFICATE OF CORRECTION

Page 1 of 1

PATENT NO. : 7,834,155 B2
APPLICATION NO. : 11/213046
DATED : November 16, 2010
INVENTOR(S) : Gillian Payne, Philip Chun and Daniel J. Tavares It is certified that error appears in the above-identified patent and that said Letters Patent is hereby corrected as shown below:

Column 23, Line 12, delete "s, and t are" and insert -- s, t and u are --.

Column 26, Line 4, delete "$(CR_7R_8)_i(CR_9=CR_{10})_p(C{\equiv}C)A_qA_o(CR_5R_6)_mD_u$" and insert
-- $(CR_7R_8)_i(CR_9=CR_{10})_p(C{\equiv}C)_qA_o(CR_5R_6)_mD_u$ --.

Column 27, Line 4, delete "$(CR_7R_8)_i(CR_9=CR_{10})_p(C{\equiv}C)A_qA_o(CR_5R_6)_mD_u$" and insert
-- $(CR_7R_8)_i(CR_9=CR_{10})_p(C{\equiv}C)_qA_o(CR_5R_6)_mD_u$ --.

Column 28, Line 31, delete "$R_1$ is H, $R_2$ is methyl," and insert -- $R_1$ is methyl, $R_2$ is H, --.

Column 59, SEQ ID NO 10, Line 1, delete "Gln Ala Gln Leu Gln Val Ser Gly Ala Glu Val
Val Lys Pro Gly Ala", and insert -- Gln Ala Gln Leu Val Gln Ser Gly Ala Glu Val Val
Lys Pro Gly Ala --.

Column 61, SEQ ID NO 11, Line 1, delete "Gln Ala Gln Leu Gln Val Ser Gly Ala Glu Val
Val Lys Pro Gly Ala", and insert -- Gln Ala Gln Leu Val Gln Ser Gly Ala Glu Val Val
Lys Pro Gly Ala --.

Column 71, SEQ ID NO 40, Line 1, delete "caggtgtaca ctcccaggct cagctccagg tgtctggggc
tgaggtggtg aagcccgggg", and insert -- caggtgtaca ctcccaggct cagctcgtgc agtctggggc
tgaggtggtg aagcccgggg --.

Signed and Sealed this

Thirteenth Day of March, 2012

David J. Kappos
*Director of the United States Patent and Trademark Office*